US009278959B2

(12) United States Patent
DiMagno

(10) Patent No.: US 9,278,959 B2
(45) Date of Patent: Mar. 8, 2016

(54) PROCESSES AND REAGENTS FOR MAKING DIARYLIODONIUM SALTS

(71) Applicant: NUtech Ventures, Lincoln, NE (US)

(72) Inventor: Stephen DiMagno, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 0 days.

(21) Appl. No.: 13/905,668

(22) Filed: May 30, 2013

(65) Prior Publication Data
US 2013/0324718 A1 Dec. 5, 2013

Related U.S. Application Data

(60) Provisional application No. 61/655,860, filed on Jun. 5, 2012.

(51) Int. Cl.
C07C 69/96 (2006.01)
C07D 413/12 (2006.01)
C07C 68/06 (2006.01)
C07C 253/30 (2006.01)
C07C 269/00 (2006.01)
C07C 41/01 (2006.01)
C07C 217/26 (2006.01)
C07D 277/30 (2006.01)
C07D 213/57 (2006.01)
C07C 41/30 (2006.01)
C07C 71/00 (2006.01)
C07C 51/41 (2006.01)
C07C 269/06 (2006.01)

(52) U.S. Cl.
CPC .............. *C07D 413/12* (2013.01); *C07C 41/01* (2013.01); *C07C 41/30* (2013.01); *C07C 51/412* (2013.01); *C07C 68/06* (2013.01); *C07C 71/00* (2013.01); *C07C 217/26* (2013.01); *C07C 253/30* (2013.01); *C07C 269/00* (2013.01); *C07C 269/06* (2013.01); *C07D 213/57* (2013.01); *C07D 277/30* (2013.01); *C07C 69/96* (2013.01)

(58) Field of Classification Search
CPC .............................. C07C 69/96; C07C 51/412
See application file for complete search history.

(56) References Cited

U.S. PATENT DOCUMENTS

2011/0190505 A1 8/2011 DiMagno
2011/0313170 A1 12/2011 DiMagno
2012/0004417 A1 1/2012 DiMagno

FOREIGN PATENT DOCUMENTS

WO WO 2014/066772 5/2014

OTHER PUBLICATIONS

International Search Report and Written Opinion in International Application No. PCT/US2013/043348, mailed Sep. 6, 2013, 13 pages.
Al-Qahtani and Pike, "Palladium(II)-mediated $^{11}$C-carbonylative coupling of diaryliodonium salts with organostannanes—a new, mild and rapid synthesis of aryl [$^{11}$C]ketones," *J Chem Soc, Perkin Trans.* 1, 2000, 1033-1036.
Cerioni and Uccheddu, "Solution structure of bis(acetoxy)iodoarenes as observed by $^{17}$O NMR spectroscopy," *Tetrahedron Lett.*, Jan. 12, 2004, 45(3):505-507.
Ciufolini et al., "Oxidative Amidation of Phenols through the Use of Hypervalent Iodine Reagents: Development and Applications," *Synthesis*, 2007, 3759-3772.
Crivello, Polym. Prepr. (Am. Chem. Soc., Div. Polym. Chem.) 2006, 47, 208-209.
Crivello, "A new visible light sensitive photoinitiator system for the cationic polymerization of epoxides," J. Polym. Sci., Part A: Polym. Chem., 2009, 47, 866-875.
Kang et al., "Palladium-catalyzed coupling and carbonylative coupling of silyloxy compounds with hypervalent iodonium salts," *Tetrahedron Lett.*, Mar. 17, 1997, 38(11):1947-1950.
Kang et al., "Palladium-Catalyzed Cross-Coupling of Organoboron Compounds with Iodonium Salts and Iodanes," J. Org. Chem., 1996, 61(14):4720-4724.
Kazmierczak and Skulski, "A simple, two-step conversion of various iodo arenes to (diacetoxyiodo) arenes with chromium(VI) oxide as the oxidant," *Synthesis*, Dec. 1998, 1721-1723.
Moore and Hanson, "Hypervalent iodine-promoted phenolic oxidations: Generation of a highly versatile o-quinone template," Chemtracts 2002, 15:74-80.
Moriarty and Prakash, "Oxidation of phenolic compounds with organohypervalent iodine reagents," *Org. React. (N. Y.)*, 2001, 57:327-415.
Ochiai et al., "Boron-Iodine (III) Exchange Reaction: Direct Synthesis of Diaryliodonium Tetraarylborates from (Diacetoxyiodo)arenes by the Reaction with Alkali Metal Tetraarylborates in Acetic Acid," *Tetrahedron Lett.*, 1996, 37:8421-8424.
Okuyama et al, "Solvolysis of Cyclohexenyliodonium Salt, a New Precursor for the Vinyl Cation: Remarkable Nucleofugality of the Phenyliodonio Group and Evidence for Internal Return from an Intimate Ion-Molecule Pair," *J. Am. Chem. Soc.*, 1995, 117:3360-7.
Ryan and Stang, "Direct α-Arylation of Ketones: The Reaction of Cyclic Ketone Enolates with Diphenyliodonium Triflate," Tetrahedron Lett. 1997, 38, 5061-5064.
Toba, "The Design of Photoinitiator Systems," *J. Photopolym. Sci. Technol.*, 2003, 16(1):115-118.
Ye et al., "Straight forward Synthesis of Hypervalent Iodine (III) Reagents Mediated by Selectfluor," *Organic Lett.*, 2005 7(18):3961-3964.
Zhang et al., "Diels-Alder Reaction and Double Phenylation in Reaction of Thiophenes with Diphenyliodonium Triflate," Heterocycles 2004, 64:199-206.
Zhdankin et al., "Chemistry of Polyvalent Iodine," *Chem Rev.*, 2008, 108:5299-5358.
Zhdankin et al., "Recent Developments in the Chemistry of Polyvalent Iodine Compounds," *Chem. Rev.*, 2002, 102:2523-2584.
International Preliminary Report on Patentability in International Application No. PCT/US2013/043348, mailed Dec. 18, 2014, 9 pages.
Extended European Search Report in International Application No. PCT/US2013/043348, mailed Dec. 23, 2015, 13 pages.

*Primary Examiner* — Andrew D Kosar
*Assistant Examiner* — John S Kenyon
(74) *Attorney, Agent, or Firm* — Fish & Richardson P.C.

(57) ABSTRACT

This invention relates to processes and reagents for making diaryliodonium salts, which are useful for the preparation of fluorinated and radiofluorinated aromatic compounds.

28 Claims, No Drawings

PROCESSES AND REAGENTS FOR MAKING DIARYLIODONIUM SALTS

CROSS-REFERENCE TO RELATED APPLICATIONS

This application claims priority to U.S. Provisional Application No. 61/655,860, filed Jun. 5, 2012, which is incorporated by reference in its entirety.

TECHNICAL FIELD

This invention relates to processes and reagents for making diaryliodonium salts, which are useful for the preparation of fluorinated and radiofluorinated aromatic compounds.

BACKGROUND

Diaryliodonium salts are useful as arylating agents for a large variety of organic and inorganic nucleophiles. They have also been applied in metal-catalyzed cross-coupling reactions (Ryan, J. H. and P. J. Stang, Tetrahedron Lett. 1997, 38, 5061-5064; Zhang, B.-X., et al., Heterocycles 2004, 64, 199-206; Kang, S.-K., et al., J. Org. Chem. 1996, 61, 4720-4724; Al-Qahtani, M. H. and V. W. Pike, Perkin 12000, 1033-1036; Kang, S.-K., et al., Tetrahedron Lett. 1997, 38, 1947-1950) due to the excellent leaving-group ability of the aryl iodide moiety (Okuyama, T., et al, J. Am. Chem. Soc. 1995, 117, 3360-7). Other than these applications, diaryliodonium salts were found to play a role as oxidants for dearomatization of phenols (Moriarty, R. M. and O. Prakash, Org. React. (N.Y.) 2001, 57, 327-415; Moore, J. D. and P. R. Hanson, Chemtracts 2002, 15, 74-80; Ciufolini, M. A., et al., Synthesis 2007, 3759-3772) and as cationic photoinitiators in photochemistry (Toba, Y., J. Photopolym. Sci. Technol. 2003, 16, 115-118; Crivello, J. V., J. Polym. Sci., Part A: Polym. Chem. 2009, 47, 866-875; Crivello, J. V., Polym. Prepr. (Am. Chem. Soc., Div. Polym. Chem.) 2006, 47, 208-209).

Diaryliodonium salts are also useful for the synthesis of aryl fluorides, for example, in the preparation of $^{18}$F labeled radiotracers. Aryl fluorides are structural moieties in natural products as well as a number of therapeutically important compounds, including pharmaceuticals and positron emission tomography (PET) tracers. Diaryliodonium salts are particularly useful for the nucleophilic fluorination of electron-rich arenes, a class of compounds that is inaccessible using conventional nucleophilic fluorination methods.

For at least these reasons, there is a need to develop new routes in diaryliodonium salts, particularly those having a broad range of functional groups. This application addresses this need and others.

SUMMARY

The present application provides, inter alia, a process for making a compound of Formula I:

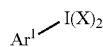

comprising treating a compound of Formula II:

Ar$^1$—I    II with a tetravalent silicon moiety having at least one X group bound to Si; and (1-chloromethyl-4-fluoro-1,4-diazoniabicyclo[2.2.2]octane)bis(tetrafluoroborate) (SelectFluor™), (1-fluoro-4-methyl-1,4-diazoniabicyclo[2.2.2]octane)bis(tetrafluoroborate) (SelectFluor II™), or optionally substituted N-fluoropyridinium tetrafluoroborate;
wherein:
each X is, independently, a ligand that is a conjugate base of an acid HX, wherein HX has a pKa of less than or equal to 12; and
Ar$^1$ is optionally substituted aryl or heteroaryl, wherein Ar$^1$ does not have unprotected protic groups.

The present application further provides a process of converting the compound of Formula I to a compound of Formula III:

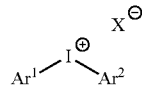

wherein Ar$^2$ is an optionally substituted aryl or heteroaryl.

The compound of Formula I can be isolated and then used to prepare the compound of Formula III or the two steps can be carried out in an efficient one-pot synthesis.

This process allows the preparation of iodine (III) precursors of Formula I without the use of acidic conditions or the use of reagents that must be prepared in acidic media as in other synthetic procedures. Acidic conditions are not compatible with substrates featuring acid sensitive moieties or heteroatoms that are prone to protonation or oxidation. Hence, the current process allows the synthesis of a broad range of diaryliodonium salts, which were previously inaccessible. For example, the process has been shown to be applicable to both electron-rich and electron-deficient arenes and is tolerant of molecules featuring acid sensitive moieties and protected L-amino acid groups. Further, this process is also more economical in that less than 2 equivalents of the oxidation agent may be utilized to achieve the oxidation, unlike other processes which use a high excess of the oxidation agent.

The present application also provides certain new compounds of Formulas I, II, III, V, VI, or VII.

DETAILED DESCRIPTION

The present application provides, inter alia, a process for making a compound of Formula I:

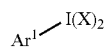

comprising treating a compound of Formula II:

Ar$^1$—I    II with a tetravalent silicon moiety having at least one X group bound to Si; and (1-chloromethyl-4-fluoro-1,4-diazoniabicyclo[2.2.2]octane)bis(tetrafluoroborate), (1-fluoro-4-methyl-1,4-diazoniabicyclo[2.2.2]octane)bis(tetrafluoroborate), or optionally substituted N-fluoropyridinium tetrafluoroborate;
wherein:
each X is, independently, a ligand that is a conjugate base of an acid HX, wherein HX has a pKa of less than or equal to 12; and
Ar$^1$ is optionally substituted aryl or heteroaryl.

In some embodiments, Ar$^1$ does not have any iodo groups (e.g., Ar$^1$—I has only the single iodo group).

In some embodiments, $Ar^1$ is optionally substituted aryl or heteroaryl, wherein $Ar^1$ does not have unprotected protic groups. As used herein, "protic groups" means groups having a hydrogen atom directly attached to an oxygen, nitrogen or sulfur atom (non-limiting examples of these groups include alcohols, primary and secondary amines, carbamates, ureas, amides, sulfonic acids, thiols, hydrazines, hydrazides, and semicarbazides).

As described above, the current process allows the synthesis of a broad range of diaryliodonium salts, including both electron-rich and electron-deficient arenes and is tolerant of molecules featuring acid sensitive moieties and protected L-amino acid groups.

Without wishing to be bound by any theory, the process is believed to operate by the process shown in the example below. It is thought that the highly activated I(III) intermediate aryl-IF+, formed from two-electron oxidation of an aryl iodide by F-TEDA-$BF_4$, is sufficiently Lewis acidic to remove a fluoride from $BF_4$— to form the aryl-$IF_2$ trifluoroborane complex. Aryl-$IF_2$ reacts subsequently with TMS-X to give 1a and TMSF, while boron trifluoride is coordinated by the free amine of reduced Selectfluor to form the zwitterionic adduct, which is able to exchange fluoride with excess TMS-X (e.g., TMSOAc). The aryl-$IF_2$ compound undergoes a fast ligand exchange process with X—. The premixed TMSOAc therefore converted aryl-$IF_2$ to corresponding ArI$(OAc)_2$ immediately upon formation of $ArIF_2$.

bamyl, di($C_{1-6}$ alkyl)carbamyl, carboxy, amino, $C_{1-6}$ alkylamino, di-$C_{1-6}$ alkylamino, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; wherein said $C_{1-6}$ alkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl are each optionally substituted by one or more groups selected from halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, hydroxy, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, amino, $C_{1-6}$ alkylamino, di-$C_{1-6}$ alkylamino, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, di($C_{1-6}$ alkyl)aminocarbonylamino, and $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl.

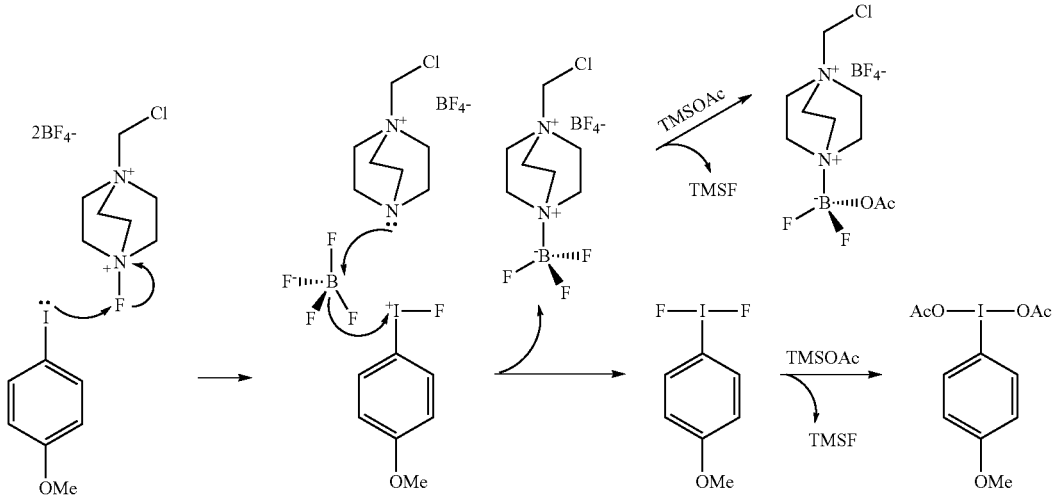

In some embodiments, the process is carried out in the absence of added acid (e.g., protic acid).

In some embodiments, the process utilizes (1-chloromethyl-4-fluoro-1,4-diazoniabicyclo[2.2.2]octane)bis(tetrafluoroborate).

In some embodiments, the process utilizes (1-fluoro-4-methyl-1,4-diazoniabicyclo[2.2.2]octane)bis(tetrafluoroborate).

In some embodiments, the process utilizes N-fluoropyridinium tetrafluoroborate, wherein the pyridine ring is optionally substituted by 1, 2, 3, 4, or 5 groups independently selected from halo, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, hydroxy, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, carbamyl, $C_{1-6}$ alkylcar- In some embodiments, the process utilizes N-fluoropyridinium tetrafluoroborate, wherein the pyridine ring is optionally substituted by 1, 2, 3, 4, or 5 groups independently selected halo groups.

In some embodiments, the process utilizes N-fluoropyridinium tetrafluoroborate, wherein the pyridine ring is optionally substituted by 1, 2, 3, 4, or 5 groups independently selected halo groups.

In some embodiments, the process utilizes N-fluoro-2,3,4,5,6-pentachloropyridinium tetrafluoroborate.

In some embodiments, the process utilizes less than 2 equivalents of (1-chloromethyl-4-fluoro-1,4-diazoniabicyclo[2.2.2]octane)bis(tetrafluoroborate), (1-fluoro-4-methyl-1,4-diazoniabicyclo[2.2.2]octane)bis(tetrafluoroborate), or optionally substituted N-fluoropyridinium tetrafluoroborate for 1 equivalent of the compound of Formula II. In some embodiments, the process utilizes less than 1.5 equivalents of (1-chloromethyl-4-fluoro-1,4-diazoniabicyclo[2.2.2]octane) bis(tetrafluoroborate), (1-fluoro-4-methyl-1,4-diazoniabicyclo[2.2.2]octane)bis(tetrafluoroborate), or optionally substituted N-fluoropyridinium tetrafluoroborate for 1 equivalent of the compound of Formula II.

In some embodiments, each X is, independently, a ligand that is a conjugate base of an acid HX, wherein HX has a pKa of less than or equal to 5.

In some embodiments, X can be chosen from halide, aryl carboxylate, alkyl carboxylate, phosphate, phosphonate, phosphonite, azide, thiocyanate, cyanate, phenoxide, triflate, thiolates, and stabilized enolates.

In some embodiments, X is $O(C=O)CH_3$.

In some embodiments, the tetravalent silicon moiety is $(R^1)_3Si-X$, $(R^1)_2Si-(X)_2$, $R^1Si-(X)_3$, and $Si(X)_4$; wherein each $R^1$ is, independently, $C_{1-12}$ alkyl or aryl.

In some embodiments, the tetravalent silicon moiety is $(R^1)_3Si-X$, wherein each $R^1$ is, independently, $C_{1-12}$ alkyl or aryl.

In some embodiments, each $R^1$ is, independently, $C_{1-12}$ alkyl.

In some embodiments, each $R^1$ is, independently, $C_{1-4}$ alkyl.

In some embodiments, each $R^1$ is independently, methyl.

In some embodiments, $(R^1)_3Si-X$ is $(CH_3)_3Si-X$.

In some embodiments, $(R^1)_3Si-X$ is $(CH_3)_3Si-O(C=O)CH_3$.

At various points, the process utilizes protecting groups. Appropriate protecting groups for various functional groups include, but are not limited to the protecting groups delineated in Wuts and Greene, Protective Groups in Organic Synthesis, 4th ed., John Wiley & Sons: New Jersey, which is incorporated herein by reference in its entirety. For example, protecting groups for amines include, but are not limited to, t-butoxycarbonyl (BOC), benzyloxycarbonyl (Cbz), 2,2,2-trichloroethoxycarbonyl (Troc), 2-(4-trifluoromethylphenylsulfonyl)ethoxycarbonyl (Tsc), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP).

Carboxylic acids can be protected as their alkyl, allyl, or benzyl esters, among other groups.

Alcohols can be protected as esters, such as acetyl, benzoyl, or pivaloyl, or as ethers. Examples of ether protecting groups for alcohols include, but are not limited to alkyl, allyl, benzyl, methoxymethyl (MOM), t-butoxymethyl, tetrahydropyranyl (THP), p-methoxybenzyle (PMB), trityl, and methoxyethoxymethyl (MEM).

In some embodiments, the protecting groups are acid labile protecting groups.

In some embodiments, the protecting groups are base labile protecting groups.

In some embodiments, the protecting group are acid labile protecting groups, which can be easily be removed at the end of all synthetic steps under acidic deprotection conditions.

In some embodiments, the process utilizes 2 equivalents or more of the tetravalent silicon moiety for 1 equivalent of the compound of Formula II. As used herein, the equivalents are per X group bound to the Si atom of the tetravalent silicon moiety (e.g., when 2X groups are bound to the Si atom, then only 1 equivalent or more of the tetravalent silicon moiety is needed for 1 equivalent of the compound of Formula II). In some embodiments, the process utilizes 2.5 equivalents to 3 equivalents of the tetravalent silicon moiety for 1 equivalent of the compound of Formula II. In some embodiments, the process utilizes 2 equivalents or more of $(R^1)_3Si-X$ for 1 equivalent of the compound of Formula II. In some embodiments, the process utilizes 2.5 equivalents to 3 equivalents of $(R^1)_3Si-X$ for 1 equivalent of the compound of Formula II.

In some embodiments, the processes comprises treating a compound of Formula II with $(CH_3)_3Si-O(C=O)CH_3$; and (1-chloromethyl-4-fluoro-1,4-diazoniabicyclo[2.2.2]octane) bis(tetrafluoroborate). In some embodiments, the processes comprises treating a compound of Formula II with 2.5 equivalents to 3 equivalents of $(CH_3)_3Si-O(C=O)CH_3$; and less than 1.5 equivalents of (1-chloromethyl-4-fluoro-1,4-diazoniabicyclo[2.2.2]octane)bis(tetrafluoroborate).

In some embodiments:

$Ar^1$ is aryl or heteroaryl, which is optionally substituted by one or more groups independently selected from halo, cyano, nitro, $C_{1-16}$ alkyl, $C_{1-6}$ haloalkyl, $C_{2-16}$ alkenyl, $C_{2-16}$ alkynyl, $C_{1-6}$ alkoxy, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-14}$ heteroaryl, $C_{1-14}$ heteroaryl-$C_{1-4}$-alkyl, $-S(=O)R^a$, $-S(=O)_2R^a$, $-S(=O)_2NR^gR^h$, $-C(=O)R^b$, $-C(=O)NR^gR^h$, $-OC(=O)R^a$, $-OC(=O)NR^gR^h$, $-NR^kC(=O)R^a$, $-NR^kC(=O)OR^b$, $NR^kC(=O)NR^gNR^h$, $-NR^kS(=O)_2R^a$, $-NR^kS(=O)_2NR^gR^h$, $C(=NR^i)NR^gR^h$, $NR^kC(=NR^i)NR^gR^h$, $-OC^c$, $-SR^d$, $-S(=O)_2OR^e$, $-C(=O)OR^f$, and $-NR^gR^h$; wherein said $C_{1-6}$ alkyl, $C_{1-6}$ haloalkyl, $C_{2-6}$ alkenyl, $C_{2-6}$ alkynyl, $C_{1-6}$ alkoxy, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-14}$ heteroaryl, and $C_{1-14}$ heteroaryl-$C_{1-4}$-alkyl are each optionally substituted by one or more independently selected $R^2$ groups;

each $R^i$ is independently selected from H, $C_{1-6}$ alkyl, CN, $C_{1-6}$ alkoxy, or $C(O)C_{1-6}$ alkyl;

each $R^a$ is independently selected from H, $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^c$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^d$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^e$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^f$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^k$, $R^g$ and $R^h$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

or alternatively, $R^k$ and $R^a$, taken together with the atoms to which they are attached, form a heterocycloalkyl or heteroaryl ring, which is optionally substituted by one or more $R^2$ groups;

or alternatively, $R^k$ and $R^b$, taken together with the atoms to which they are attached, form a heterocycloalkyl or heteroaryl ring, which is optionally substituted by one or more $R^2$ groups;

or alternatively, $R^k$ and $R^g$, taken together with the atoms to which they are attached, form a heterocycloalkyl or heteroaryl ring, which is optionally substituted by one or more $R^2$ groups;

or alternatively, $R^g$ and $R^h$, taken together with the nitrogen atom to which they are attached, form a heterocycloalkyl or heteroaryl ring, which is optionally substituted by one or more $R^4$ groups;

each $R^2$ is independently selected from halo, cyano, nitro, $C_{1-6}$ alkyl, $C_{1-6}$ haloalkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{7-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —S(=O)$R^{a1}$, —S(=O)$_2R^{a1}$, —S(=O)$_2NR^{g1}R^{h1}$, —C(=O)$R^{b1}$, —C(=O)NR$^{g1}R^{h1}$, —OC(=O)$R^{a1}$, —OC(=O)NR$^{g1}R^{h1}$, —NR$^{k1}$C(=O)$R^{a1}$, —NR$^{k1}$C(=O)OR$^{b1}$, —NR$^{k1}$C(=O)NR$^{g1}NR^{h1}$, —NR$^{k1}$S(=O)$_2R^{a1}$, —NR$^{k1}$S(=O)$_2NR^{g1}R^{h1}$, C(=NR$^i$)NR$^{g1}R^{h1}$, NR$^{k1}$C(=NR$^j$)NR$^{g1}R^{h1}$, —OR$^{c1}$, —SR$^{d1}$, —S(=O)$_2OR^{e1}$, —C(=O)OR$^{f1}$, and —NR$^{g1}R^{h1}$; wherein said $C_{1-6}$ alkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{a1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{c1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{d1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{e1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{f1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{k1}$, $R^{g1}$ and $R^{h2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

or alternatively, $R^{k1}$ and $R^{a1}$, taken together with the atoms to which they are attached, form a heterocycloalkyl or heteroaryl ring, which is optionally substituted by one or more $R^3$ groups;

or alternatively, $R^{k1}$ and $R^{b1}$, taken together with the atoms to which they are attached, form a heterocycloalkyl or heteroaryl ring, which is optionally substituted by one or more $R^3$ groups;

or alternatively, $R^{k1}$ and $R^{g1}$, taken together with the atoms to which they are attached, form a heterocycloalkyl or heteroaryl ring, which is optionally substituted by one or more $R^3$ groups;

or alternatively, $R^{g1}$ and $R^{h1}$, taken together with the nitrogen atom to which they are attached, form a heterocycloalkyl or heteroaryl ring, which is optionally substituted by one or more $R^3$ groups;

each $R^3$ is independently selected from halo, cyano, nitro, $C_{1-6}$ alkyl, $C_{1-6}$ haloalkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —S(=O)$R^{a2}$, —S(=O)$_2R^{a2}$, —S(=O)$_2$NR$^{g2}$R$^{h2}$, —C(=O)$R^{b2}$, —C(=O)NR$^{g2}$R$^{h2}$, —OC(=O)$R^{a2}$, —OC(=O)NR$^{g2}$R$^{h2}$, —NR$^{k2}$C(=O)$R^{a2}$, —NR$^{k2}$C(=O)OR$^{b2}$, —NR$^{k2}$C(=O)NR$^{g2}$NR$^{h2}$, —NR$^{k2}$S(=O)$_2R^{a2}$, —NR$^{k2}$S(=O)$_2$NR$^{g2}$R$^{h2}$, C(=NR$^i$)NR$^{g2}$R$^{h2}$, NR$^{k2}$C(=NR$^i$)NR$^{g2}$R$^{h2}$, —OR$^{c2}$, —SR$^{d2}$, —S(=O)$_2$OR$^{e2}$, —C(=O)OR$^{f2}$, and —NR$^{g2}$R$^{h2}$; wherein said $C_{1-6}$ alkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{a2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{c2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{d2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{e2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{f2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{k2}$, $R^{g2}$ and $R^{h2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

or alternatively, $R^{k2}$ and $R^{a2}$, taken together with the atoms to which they are attached, form a heterocycloalkyl or heteroaryl ring, which is optionally substituted by one or more $R^4$ groups;

or alternatively, $R^{k2}$ and $R^{b2}$, taken together with the atoms to which they are attached, form a heterocycloalkyl or heteroaryl ring, which is optionally substituted by one or more $R^4$ groups;

or alternatively, $R^{k2}$ and $R^{g2}$, taken together with the atoms to which they are attached, form a heterocycloalkyl or heteroaryl ring, which is optionally substituted by one or more $R^4$ groups;

or alternatively, $R^{g2}$ and $R^{h2}$, taken together with the nitrogen atom to which they are attached, form a heterocycloalkyl or heteroaryl ring, which is optionally substituted by one or more $R^4$ groups;

each $R^4$ is independently selected from halo, cyano, nitro, $C_{1-6}$ alkyl, $C_{1-6}$ haloalkyl, $C_{1-6}$ alkyl-$NR^{4a}$—$C_{1-6}$ alkylene, $C_{1-6}$ alkyl-O—$C_{1-6}$ alkylene, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, hydroxy, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, amino, $C_{1-6}$ alkylamino, di-$C_{1-6}$ alkylamino, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; wherein said $C_{1-6}$ alkyl, $C_{1-6}$ haloalkyl, $C_{2-6}$ alkenyl, $C_{2-6}$ alkynyl, $C_{1-6}$ alkoxy, alkylene, $C_{1-6}$ alkyl-O—$C_{1-6}$ alkylene, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more groups selected from halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, hydroxy, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, amino, $C_{1-6}$ alkylamino, di-$C_{1-6}$ alkylamino, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, alkyl) aminocarbonylamino, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ $C_{1-10}$ heteroaryl and $C_{1-10}$ heteroaryl-$C_{1-4}$ alkyl; and each $R^{4a}$ is independently selected from H and $C_{1-6}$ alkyl.

In one embodiments of the aformentioned embodiment, it is provided that each hydrogen atom in which is directly attached to a nitrogen atom, sulfur atom, or oxygen atom in any of the aforementioned groups (e.g., heteroaryl, heterocycloalkyl, $C_{1-6}$ alkyl-$NR^{4a}$—$C_{1-6}$ alkylene, hydroxy, carbamyl, carboxy, amino, $C_{1-6}$ alkylamino, $C_{1-6}$ alkylsulfonylamino, aminosulfonyl, $C_{1-6}$ alkylaminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino) is replaced by a protecting group.

Starting materials of Formula II can be obtained by reacting the aryl or heteroaryl substrate with a N-iodosuccinamide (NIS) in an appropriate solvent such as dry acetonitrile to give a compound of Formula II. Protecting groups can added if necessary as described in Wuts and Greene, Protective Groups in Organic Synthesis, 4th ed., John Wiley & Sons: New Jersey, which is incorporated herein by reference in its entirety. For example, amine groups can be protected by reacting di-tert-butyl dicarbonate (BOC anhydride in the presence of a tertiary amine (e.g, 4-dimethylpyridine and triethylamine) to form a BOC (tert-butylcarbonyl) protected amine In some embodiments, the present application provides a process of converting the compound of Formula I to a compound of Formula III:

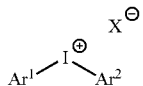

III wherein $Ar^2$ is an optionally substituted aryl or heteroaryl.

In some embodiments, the conversion of the compound of Formula I to a compound of Formula III is done in the same pot as the reaction of the compound of Formula II to form the compound of Formula I.

In some embodiments, the converting comprises reacting the compound of Formula I with a compound of Formula IV:

IV wherein $M^1$ is a borate, stannane, silane, or zinc moiety.

In some embodiments, $M^1$ is $Sn(R^x)_3$, $Si(R^y)_3$, $B(OR^z)_2$, or $B(X^2)_3M^2$; wherein:

each $R^x$ is, independently, $C_{1-6}$ alkyl;

each $R^y$ is, independently, $C_{1-6}$ alkyl;

each $R^z$ is, independently, OH or $C_{1-6}$ alkoxy; or two $R^z$ groups, taken together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups;

each $X^2$ is, independently, halo; and $M^2$ is a counterion.

In some embodiments, the zinc moiety is an zinc halide (Zn-halo). In some embodiments, the arylzinc halide is zinc chloride.

In some embodiments, the compound of Formula IV is $Ar^2BF_3M^2$.

In some embodiments, the compound of Formula IV is $Ar^2BF_3K$.

In some embodiments, the process is carried out in the presence of a catalyst.

In some embodiments, the catalyst is trimethylsilyl trifluoroacetate.

The use of $Ar^2BF_3M^2$ is preferred over the other reagents. Compared to organostannanes, organoboranes are relatively straightforward to handle and are quite reactive toward I(III) compounds. However, organoboranes themselves are limited by the inherent characteristics of the in situ hydroboration reaction used to create them. They also suffer from high sensitivity to air and poor functional-group compatibility in some cases. In contrast, aryltrifluoroborates are stable, crystalline compounds that have been shown to overcome these limitations. Organotrifluoroborates can be easily prepared from inexpensive materials. They are stable to air and moisture, features that allow shipping and storage of these reagents for long periods of time without noticeable degradation. Their versatility and stability has made them excellent reagents in many organic reactions. Further, trifluoroborates have the ability to resist chemical oxidation. This feature offers aryltrifluoroborates a unique opportunity to preserve the carbon-boron bond during the oxidation of remote functionality within the same molecule. Organoboron compounds are generally incompatible with oxidants, which readily cleave the labile carbon-boron bond. Organotrifluoroborates can be utilized to overcome this limitation in an important way; since the organometallic reagent needs to be stable to excess Selectfluor reagent that is present in one-pot synthetic approach. The oxidative strength of Selectfluor reagent is well tolerated by aryltrifluoroborates; they are unffected by residual Selectfluor.

In one embodiment (a), $Ar^1$ and $Ar^2$ are each, independently, aryl or heteroaryl, which is optionally substituted by one or more groups independently selected from halo, cyano, nitro, $C_{1-16}$ alkyl, $C_{1-6}$ haloalkyl, $C_{2-16}$ alkenyl, $C_{2-16}$ alkynyl, $C_{1-6}$ alkoxy, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-14}$ heteroaryl, $C_{1-14}$ heteroaryl-$C_{1-4}$-alkyl, —S(=O)$R^a$, —S(=O)$_2R^a$, —S(=O)$_2$NR$^g$R$^h$, —C(=O)NR$^g$R$^h$, —OC(=O)$R^a$, —OC(=O)NR$^g$R$^h$, —NR$^k$C(=O)$R^a$, —NR$^k$C(=O)OR$^b$, —NR$^k$C(=O)NR$^g$NR$^h$, —NR$^k$S(=O)$_2R^a$, —NR$^k$S(=O)$_2$NR$^g$R$^h$, C(=NR$^i$)NR$^g$R$^h$, NR$^k$C(=NR$^i$)NR$^g$R$^h$, —OC$^c$, —SR$^d$, —S(=O)$_2$OR$^e$, —C(=O)OR$^f$, and —NR$^g$R$^h$; wherein said $C_{1-6}$ alkyl, $C_{1-6}$ haloalkyl, $C_{2-6}$ alkenyl, $C_{2-6}$ alkynyl, $C_{1-6}$ alkoxy, $C_{3-14}$ cycloalkyl, $C_{3-14}$ cycloalkyl-$C_{1-4}$-alkyl, $C_{2-14}$ heterocycloalkyl, $C_{2-14}$ heterocycloalkyl-$C_{1-4}$-alkyl, $C_{6-14}$ aryl, $C_{6-14}$ aryl-$C_{1-4}$-alkyl, $C_{1-14}$ heteroaryl, and $C_{1-14}$ heteroaryl-$C_{1-4}$-alkyl are each optionally substituted by one or more independently selected $R^2$ groups;

each R' is independently selected from H, $C_{1-6}$ alkyl, CN, $C_{1-6}$ alkoxy, or C(O)$C_{1-6}$ alkyl;

each $R^a$ is independently selected from H, $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^c$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^d$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^e$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^f$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

each $R^k$, $R^g$ and $R^h$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, aryl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^2$ groups;

or alternatively, $R^k$ and $R^a$, taken together with the atoms to which they are attached, form a heterocycloalkyl or heteroaryl ring, which is optionally substituted by one or more $R^2$ groups;

or alternatively, $R^k$ and $R^b$, taken together with the atoms to which they are attached, form a heterocycloalkyl or heteroaryl ring, which is optionally substituted by one or more $R^2$ groups;

or alternatively, $R^k$ and $R^g$, taken together with the atoms to which they are attached, form a heterocycloalkyl or heteroaryl ring, which is optionally substituted by one or more $R^2$ groups;

or alternatively, $R^g$ and $R^h$, taken together with the nitrogen atom to which they are attached, form a heterocycloalkyl or heteroaryl ring, which is optionally substituted by one or more $R^4$ groups;

each $R^2$ is independently selected from halo, cyano, nitro, $C_{1-6}$ alkyl, $C_{1-6}$ haloalkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —S(=O)$R^{a1}$, —S(=O)$_2R^{a1}$, —S(=O)$_2$NR$^{g1}$R$^{h1}$, C(=O)$R^{b1}$, —C(=O)NR$^{g1}$R$^{h1}$, —OC(=O)$R^{a1}$, —OC(=O)NR$^{g1}$R$^{h1}$, NR$^{k1}$S(=O)$_2$NR$^{g1}$R$^{h1}$, C(=NR$^i$)NR$^{g1}$R$^{h1}$, NR$^{k1}$C(=NR$^i$)NR$^{g1}$R$^{h1}$, —OR$^{c1}$, —SR$^{d1}$, —S(=O)$_2$OR$^{e1}$, —C(=O)OR$^{f1}$, and —NR$^{g1}$R$^{h1}$; wherein said $C_{1-6}$ alkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$- alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{a1}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{c1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{d1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{e1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{f1}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

each $R^{k1}$, $R^{g1}$ and $R^{h2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^3$ groups;

or alternatively, $R^{k1}$ and $R^{a1}$, taken together with the atoms to which they are attached, form a heterocycloalkyl or heteroaryl ring, which is optionally substituted by one or more $R^3$ groups;

or alternatively, $R^{k1}$ and $R^{b1}$, taken together with the atoms to which they are attached, form a heterocycloalkyl or heteroaryl ring, which is optionally substituted by one or more $R^3$ groups;

or alternatively, $R^{k1}$ and $R^{g1}$, taken together with the atoms to which they are attached, form a heterocycloalkyl or heteroaryl ring, which is optionally substituted by one or more $R^3$ groups;

or alternatively, $R^{g1}$ and $R^{h1}$, taken together with the nitrogen atom to which they are attached, form a heterocycloalkyl or heteroaryl ring, which is optionally substituted by one or more $R^3$ groups;

each $R^3$ is independently selected from halo, cyano, nitro, $C_{1-6}$ alkyl, $C_{1-6}$ haloalkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —S(=O)$R^{a2}$, —S(=O)$_2R^{a2}$, —S(=O)$_2NR^{g2}R^{h2}$, —C(=O)$R^{b2}$, —C(=O)$NR^{g2}R^{h2}$, —OC(=O)$R^{a2}$, —OC(=O)$NR^{g2}R^{h2}$, —$NR^{k2}$C(=O)$R^{a2}$, —$NR^{k2}$C(=O)$OR^{b2}$, —$NR^{k2}$C(=O)$NR^{g2}NR^{h2}$, —$NR^{k2}$S(=O)$_2R^{a2}$, —$NR^{k2}$S(=O)$_2NR^{g2}R^{h2}$, C(=NR$^i$)$NR^{g2}R^{h2}$, $NR^{k2}$C(=NR$^i$)$NR^{g2}R^{h2}$, —$OR^{e2}$, —$SR^{d2}$, —S(=O)$_2OR^{e2}$, —C(=O)$OR^{f2}$, and —$NR^{g2}R^{h2}$; wherein said $C_{1-6}$ alkyl, $C_{1-6}$ haloalkyl, $C_{2-6}$ alkenyl, $C_{2-6}$ alkynyl, $C_{1-6}$ alkoxy, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{a2}$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{b2}$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{c2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{d2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{e2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{f2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

each $R^{k2}$, $R^{g2}$ and $R^{h2}$ is independently selected from a protecting group, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, wherein said $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more independently selected $R^4$ groups;

or alternatively, $R^{k2}$ and $R^{a2}$, taken together with the atoms to which they are attached, form a heterocycloalkyl or heteroaryl ring, which is optionally substituted by one or more $R^4$ groups;

or alternatively, $R^{k2}$ and $R^{b2}$, taken together with the atoms to which they are attached, form a heterocycloalkyl or heteroaryl ring, which is optionally substituted by one or more $R^4$ groups;

or alternatively, $R^{k2}$ and $R^{g2}$, taken together with the atoms to which they are attached, form a heterocycloalkyl or heteroaryl ring, which is optionally substituted by one or more $R^4$ groups;

or alternatively, $R^{g2}$ and $R^{h2}$, taken together with the nitrogen atom to which they are attached, form a heterocycloalkyl or heteroaryl ring, which is optionally substituted by one or more $R^4$ groups;

each $R^4$ is independently selected from halo, cyano, nitro, $C_{1-6}$ alkyl, $C_{1-6}$ haloalkyl, $C_{1-6}$ alkyl-$NR^{4a}$—$C_{1-6}$ alkylene, $C_{1-6}$ alkyl-O—$C_{1-6}$ alkylene, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, hydroxy, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, amino, $C_{1-6}$ alkylamino, di-$C_{1-6}$ alkylamino, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; wherein said $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ alkyl-$NR^{4a}$—$C_{1-6}$ alkylene, $C_{1-6}$ alkyl-O—$C_{1-6}$ alkylene, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by one or more groups selected from halo, cyano, nitro, $C_{1-6}$ alkyl, $C_{1-6}$ haloalkyl, $C_{2-6}$ alkenyl, $C_{2-6}$ alkynyl, $C_{1-6}$ alkoxy, hydroxy, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, amino, $C_{1-6}$ alkylamino, di-$C_{1-6}$ alkylamino, $C_{1-6}$ alkylcarbonyl, $C_{1-6}$ alkoxycarbonyl, $C_{1-6}$ alkylcarbonyloxy, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, di($C_{1-6}$ alkyl)aminocarbonylamino, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl and $C_{1-10}$ heteroaryl-$C_{1-4}$ alkyl; and each $R^{4a}$ is independently selected from H and $C_{1-6}$ alkyl;

provided that each hydrogen atom in which is directly attached to a nitrogen atom, sulfur atom, or oxygen atom in any of the aforementioned groups (e.g., heteroaryl, heterocycloalkyl, $C_{1-6}$ alkyl-$NR^{4a}$—$C_{1-6}$ alkylene, hydroxy, carbamyl, carboxy, amino, $C_{1-6}$ alkylamino, $C_{1-6}$ alkylsulfonylamino, aminosulfonyl, $C_{1-6}$ alkylaminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino) is replaced by a protecting group.

In some embodiments, optionally substituted means substituted one or more groups independently selected from halo, cyano, nitro, alkyl, haloalkyl, alkenyl, alkynyl, cycloalkyl, cycloalkylalkyl, heterocycloalkyl, heterocycloalkylalkyl, aryl, arylalkyl, heteroaryl, heteroarylalkyl, hydroxy, alkoxy, haloalkoxy, thio, alkylthio, alkylsulfinyl, alkylsulfonyl, carbamyl, alkylcarbamyl, carbamyl, carboxy, amino, alkylamino, di. alkylamino, alkylcarbonyl, alkoxycarbonyl, H-carbonyloxy, H-carbonylamino, H-sulfonylamino, aminosulfonyl, alkylaminosulfonyl, di(alkyl)aminosulfonyl, aminosulfonylamino, alkylaminosulfonylamino, di(alkyl)aminosulfonylamino, aminocarbonylamino, alkylaminocarbonylamino, dialkyl)aminocarbonylamino, hydrazine, hydrazines, hydrazides, and semicarbazides; wherein each group can be further optionally substituted by one or more groups independently selected from the aforementioned groups. In some embodiments, multiple layers of substitution are permitted.

In some embodiments, $Ar^1$ and $Ar^2$ do not comprise an iodo group.

In some embodiments, $Ar^1$ is defined as in embodiment (a).

In some embodiments, $Ar^2$ is defined as in embodiment (a).

In some embodiments, $Ar^2$ is aryl substituted by 1, 2, 3, 4, or 5 $C_{1-6}$ alkoxy groups.

In some embodiments, $Ar^2$ is aryl substituted by 1, 2, 3, 4, or 5 methoxy groups.

In some embodiments, $Ar^2$ is aryl substituted by 1 or 2 $C_{1-6}$ alkoxy groups.

In some embodiments, $Ar^2$ is aryl substituted by 1 or 2 methoxy groups.

In some embodiments, $Ar^2$ is aryl substituted by $1C_{1-6}$ alkoxy group.

In some embodiments, $Ar^2$ is aryl substituted by 1 methoxy group.

In some embodiments, $Ar^2$ is phenyl substituted by 1, 2, 3, 4, or 5 $C_{1-6}$ alkoxy groups.

In some embodiments, $Ar^2$ is phenyl substituted by 1, 2, 3, 4, or 5 methoxy groups.

In some embodiments, $Ar^2$ is phenyl substituted by 1 or 2 $C_{1-6}$ alkoxy groups.

In some embodiments, $Ar^2$ is phenyl substituted by 1 or 2 methoxy groups.

In some embodiments, $Ar^2$ is phenyl substituted by 1 $C_{1-6}$ alkoxy group.

In some embodiments, $Ar^2$ is phenyl substituted by 1 methoxy group.

In some embodiments, $Ar^2$ is p-methoxyphenyl.

In some embodiments, $Ar^2$ is 3,4-dimethoxyphenyl.

In some embodiments, $Ar^2$ is Formula (I):

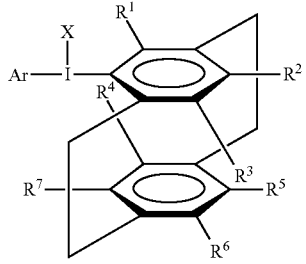

or Formula (4):

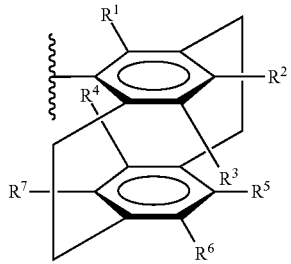

wherein:

$R^1$ is hydrogen or a substituent having a Hammett $\sigma_p$ value of less than zero; and $R^2$, $R^3$, $R^4$, $R^5$, $R^6$, and $R^7$ are independently selected from the group consisting of: H, $CF_3$, $OCF_3$, CN, hydroxyl, amino, aminoalkyl, $(CH_2)_nN(CH_2)_m$, $-SR^8$, $-SOR^8$, halo, $SO_2R^8$, $(CH_2)_nOR^8$, $C(=O)NR^8R^9$, $SO_2NR^8R^9$, $NR^8SO_2R^9$, $COOR^8$, $NR^8C(=O)R^9$, $NR^8C(=O)NR^9$, $SO_2R^8$, $(CH_2)_nC(=O)NR^8R^9$, $(CH_2)_nSO_2NR^8R^9$, $(CH_2)_nNR^8SO_2R^9$, $(CH_2)_nCOOR^8$, $(CH_2)_nNR^8C(=O)R^9$, $(CH_2)_nNR^8C(=O)NR^9$, alkoxy, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, substituted or unsubstituted heteroaryl, and $(L)_p$-Z, or one or more of $R^2$ and $R^3$, $R^4$ and $R^7$, and $R^5$ and $R^6$ come together to form a fused cycloalkyl, heterocycloalkyl, aryl, or heteroaryl ring system;

each m, n, and p are independently an integer from 0 to 10;

each $R^8$ and $R^9$ are independently chosen from H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, and substituted or unsubstituted heteroaryl;

L is a linker; and

Z is a solid support.

The aryl rings on the cyclophane moiety can be substituted or unsubstituted. In some embodiments, $R^1$ is selected from the group consisting of: $-(C_1-C_{10})$alkyl, $-(C_1-C_{10})$haloalkyl, $(C_2-C_{10})$alkenyl, $(C_2-C_{10})$alkynyl, $-O-(C_1-C_{10})$alkyl, $-C(O)-O-(C_1-C_{10})$alkyl, aryl, and heteroaryl. For example, $R^1$ can be $-O-(C_1-C_{10})$alkyl (e.g., $OCH_3$). In some embodiments, $R^2$ is $-O-(C_1-C_{10})$alkyl (e.g., $OCH_3$). For example, a compound of Formula (1) can be chosen from:

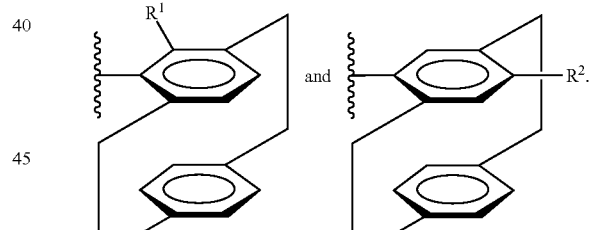

In some embodiments, one or more of $R^2$-$R^7$ is $(L)_p$-Z. L and Z can be covalently or noncovalently bound to one another.

In some embodiments, $Ar^2$ is any of the cyclophanes in US 2011/0190505, which is incorporated herein by reference in its entirety.

In some embodiments, $Ar^1$ is defined as in embodiment (a); and $Ar^2$ is one of the specific embodiments above.

In some embodiments, the present application provides a compound of Formula I or III as defined herein, wherein $Ar^1$ comprises at least one acid-labile protecting group or acid-sensitive group. In some embodiments, "acid-labile" or "acid-sensitive" means not stable to or protonated by 1 N hydrochloric acid.

In some embodiments, the process further comprises subjecting the compound of Formula III to ion-exchange in order to form a compound of Formula V:

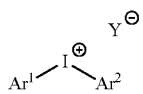

wherein Y is a counterion that is different than X.

In some embodiments, Y is a weakly coordinating anion (i.e., an anion that coordinates only weakly with iodine). For example, Y can be the conjugate base of a strong acid, for example, any anion for which the pKa of the conjugate acid (H—Y) is less than about 1. For example, Y can be triflate, mesylate, nonaflate, hexaflate, toluene sulfonate (tosylate), nitrophenyl sulfonate (nosylate), bromophenyl sulfonate (brosylate), perfluoroalkyl sulfonate (e.g., perfluoro $C_{2-10}$ alkyl sulfonate), tetraphenylborate, hexafluorophosphate, trifluoroacetate, perfluoroalkylcarboxylate, tetrafluoroborate, perchlorate, hexafluorostibate, hexachlorostibate, chloride, bromide, or iodide. In some embodiments, a slightly more basic leaving group such as acetate or benzoate may be used.

In some embodiments, the ion-exchange comprises treating the compound of Formula III with an aqueous solution of hexafluorophosphate ion, wherein Y is $PF_6-$.

In some embodiments, the ion-exchange comprises treating the compound of Formula III with an aqueous solution of sodium hexafluorophosphate ion, wherein Y is $PF_6-$.

The present application further provides a process of forming a compound of Formula III:

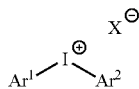

comprising:
(a) treating a compound of Formula II:

Ar¹—I  II with more than 2 equivalents of $(R^1)_3Si—X$; and less than 2 equivalents of (1-chloromethyl-4-fluoro-1,4-diazoniabicyclo[2.2.2]octane)bis(tetrafluoroborate) or (1-fluoro-4-methyl-1,4-diazoniabicyclo[2.2.2]octane)bis(tetrafluoroborate) in the absence of added acid to form a compound of Formula I:

and
(b) reacting the compound of Formula I with $Ar^2BF_4M^2$ in the presence of a catalyst to form a compound of Formula III: wherein:
each X is, independently, a ligand, wherein HX, the conjugate acid of X, has a $pK_a$ of less than or equal to 5;
$Ar^1$ is optionally substituted aryl or heteroaryl, wherein $Ar^1$ does not have unprotected protic groups;
$Ar^2$ is an optionally substituted aryl or heteroaryl;
each $R^1$ is, independently, $C_{1-4}$ alkyl; and
$M^2$ is a cation.

In some embodiments, the process utilizes (1-chloromethyl-4-fluoro-1,4-diazoniabicyclo[2.2.2]octane)bis(tetrafluoroborate); and $(R^1)_3Si—X$ is $(CH_3)_3Si—O(C=O)CH_3$.

In some embodiments, steps (a) and (b) are carried out in a single pot.

In some embodiments, the present application provides compounds of Formula II and processes utilizing compounds of Formula II (e.g., a process of making a compound of Formula I, III, V, VI, or VII), wherein the compounds of Formula II are selected from any of the following:

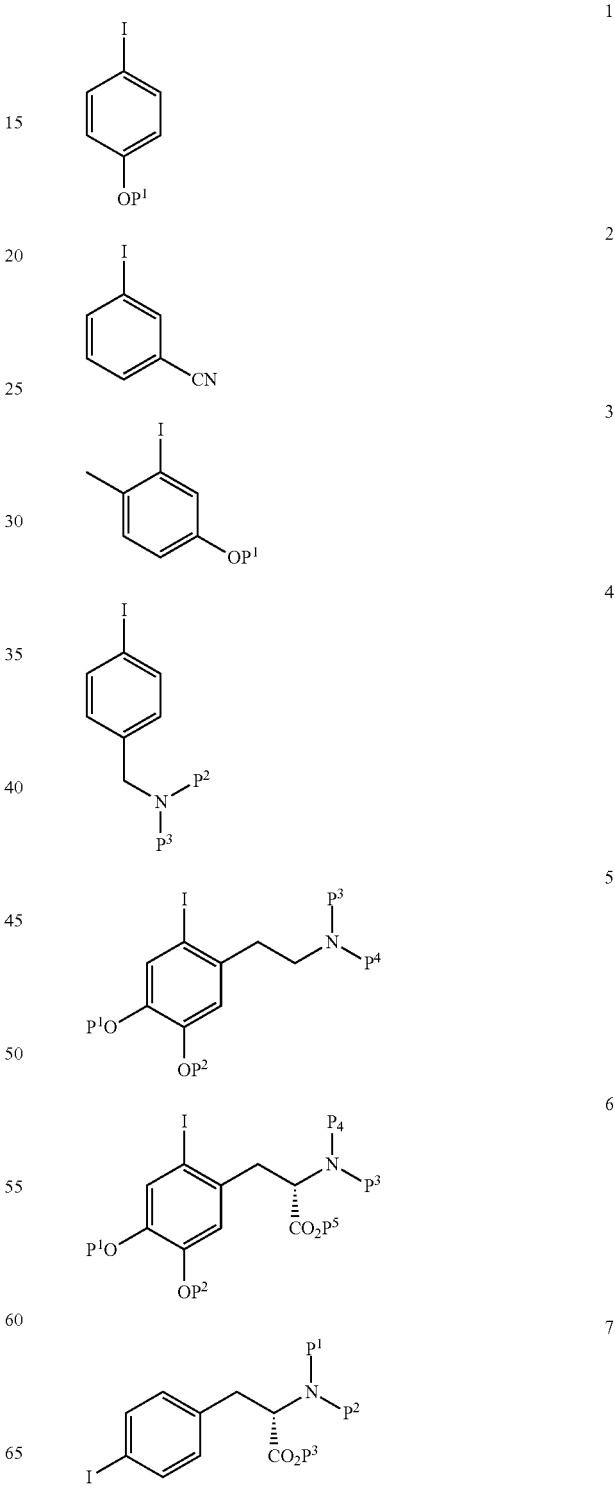

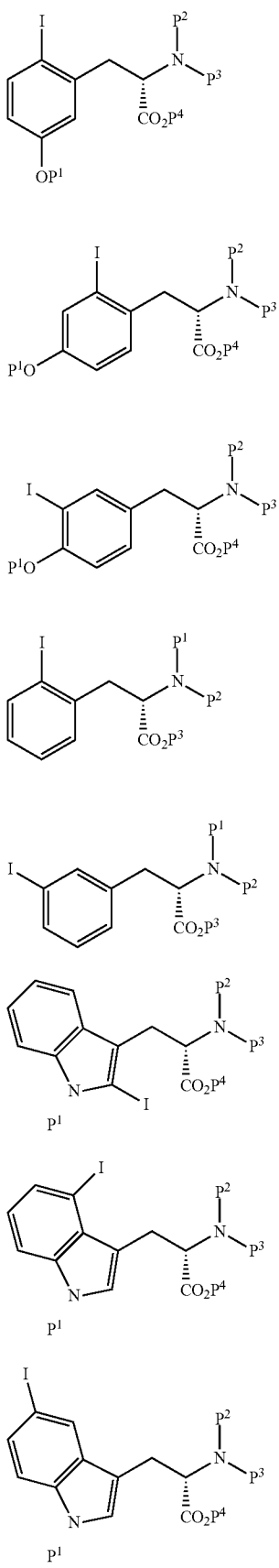
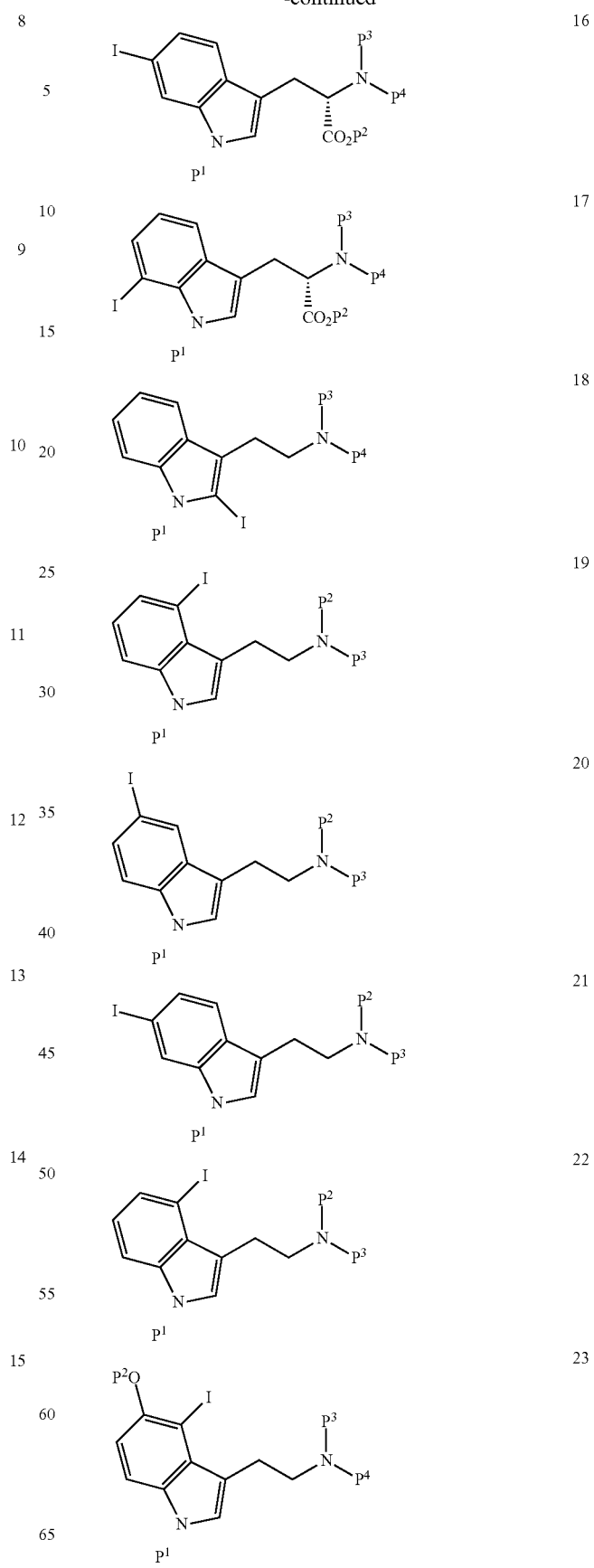

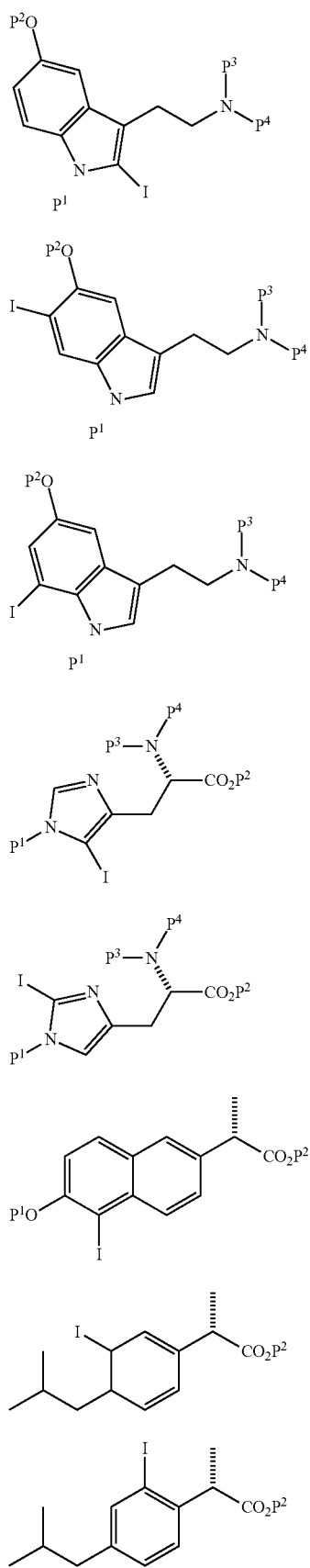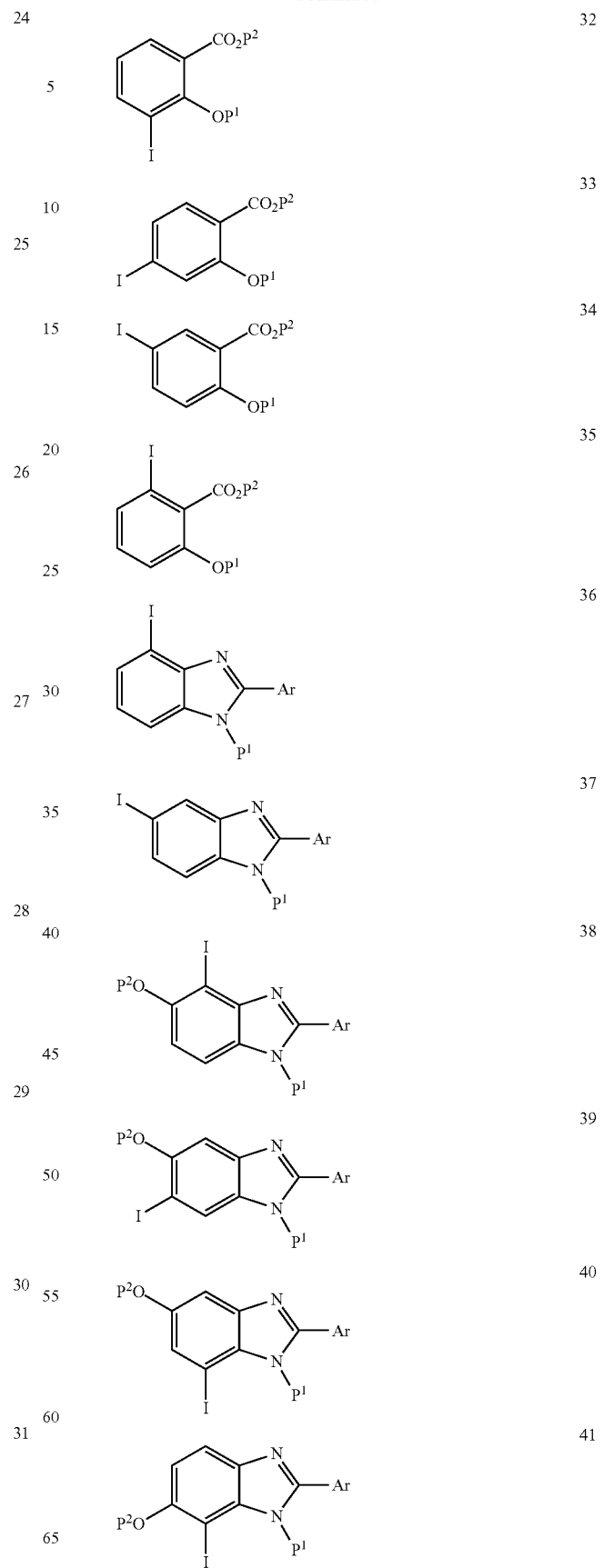

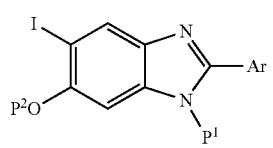
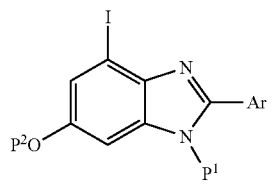
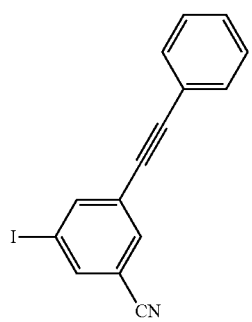
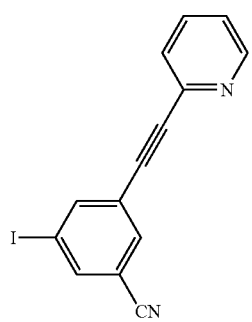
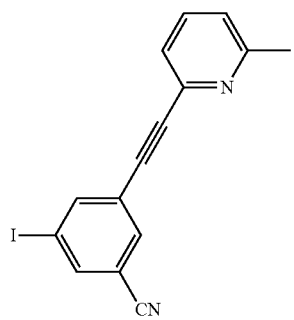
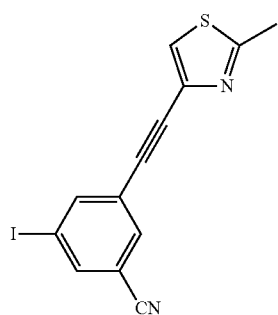
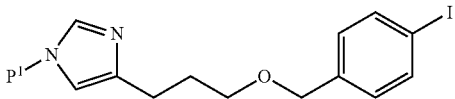
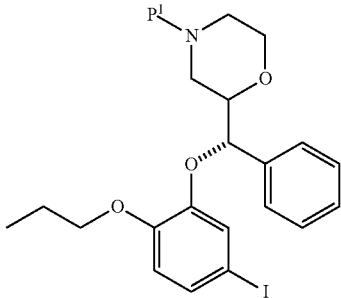
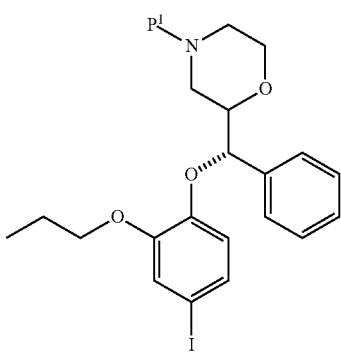
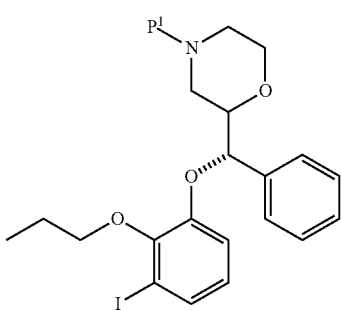
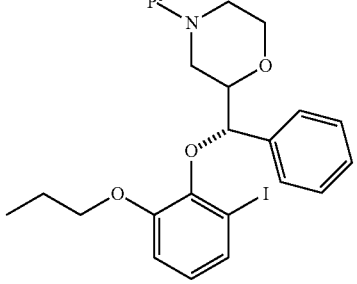
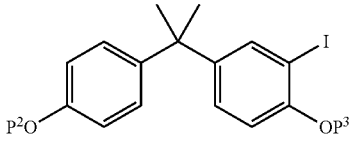

54
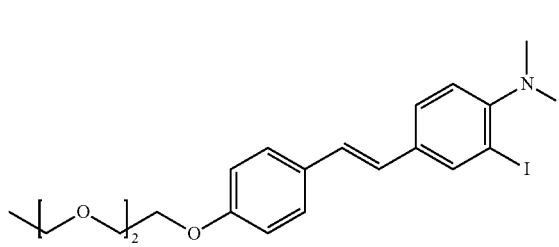
55
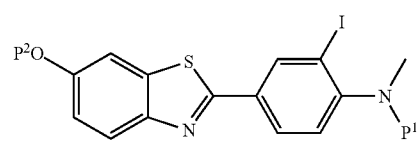
56
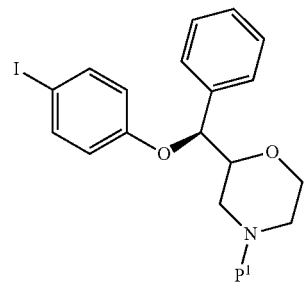
57
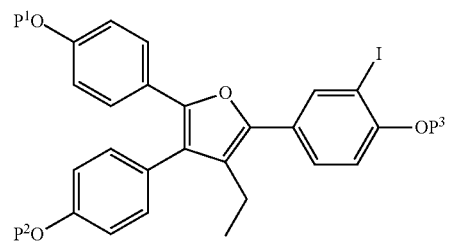
58
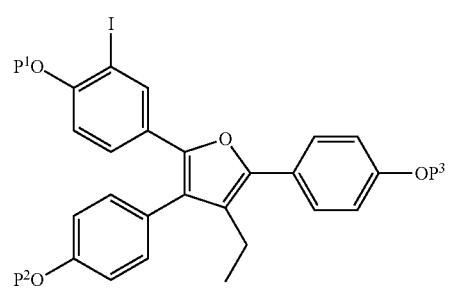
59
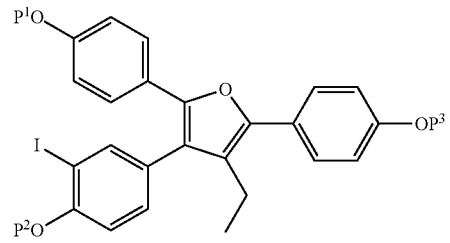
60
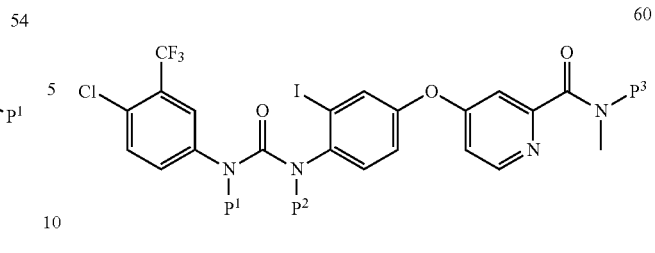
61
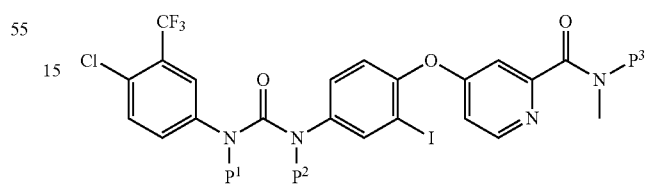
62
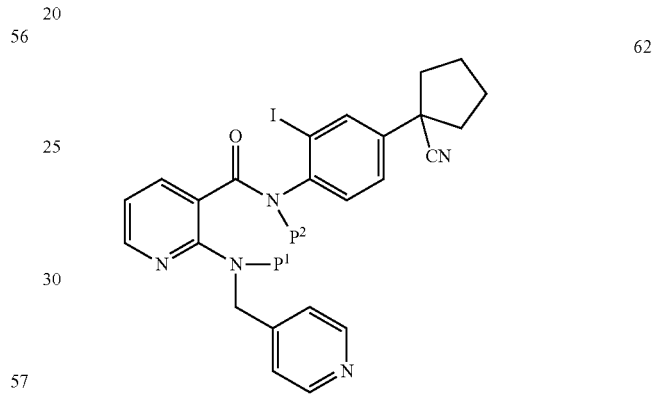
63
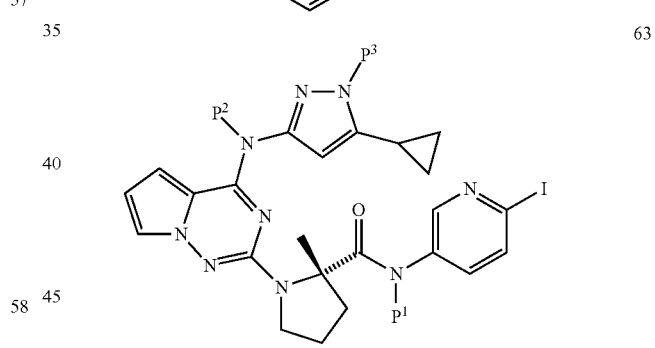
64
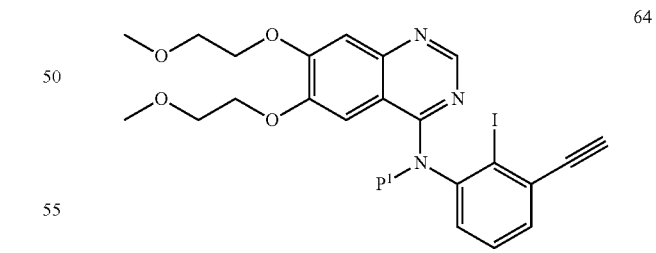
65
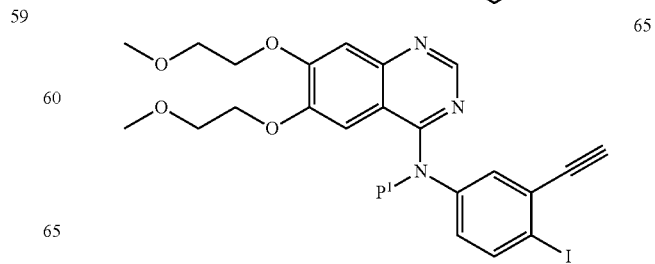

66
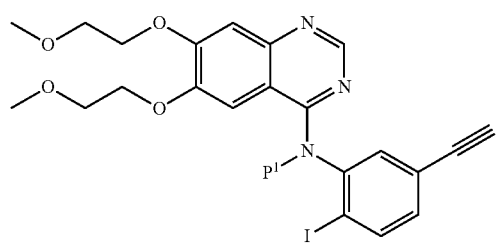
67
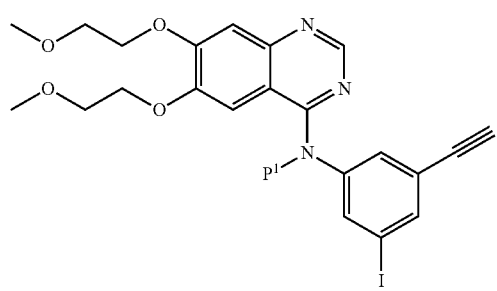
68
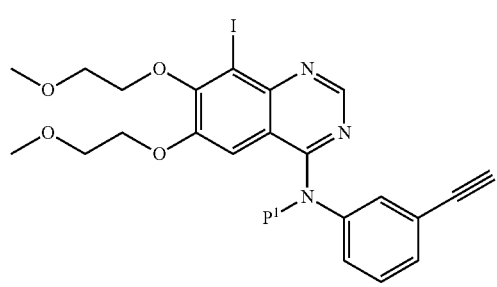
69
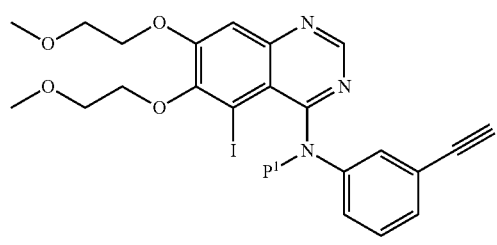
70
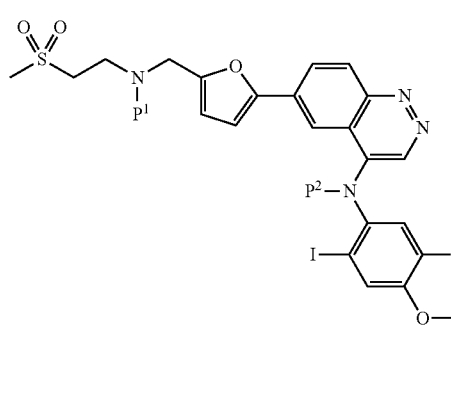
71
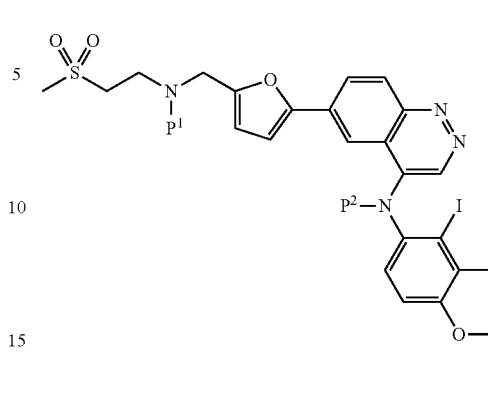
72
73
74
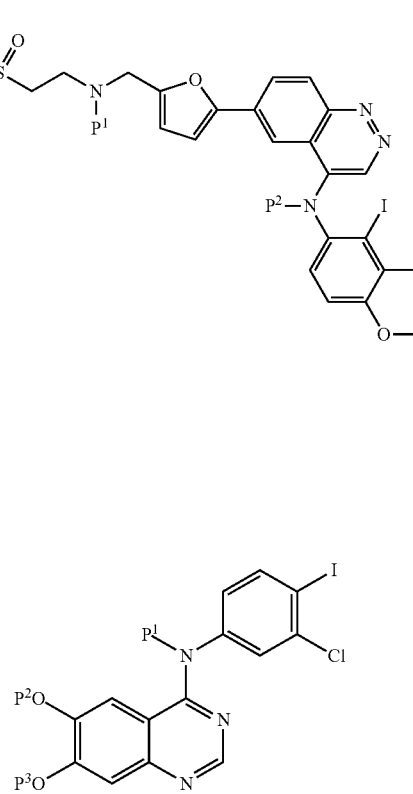
75
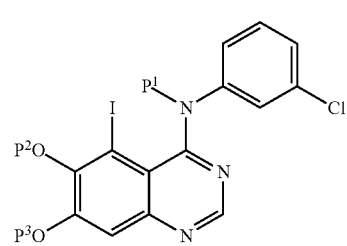

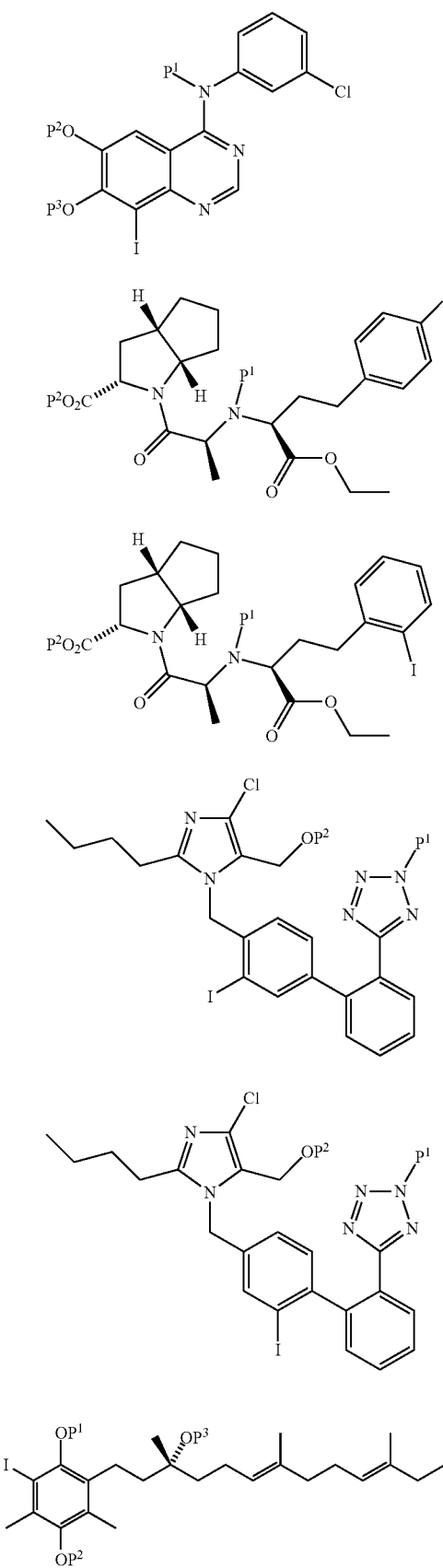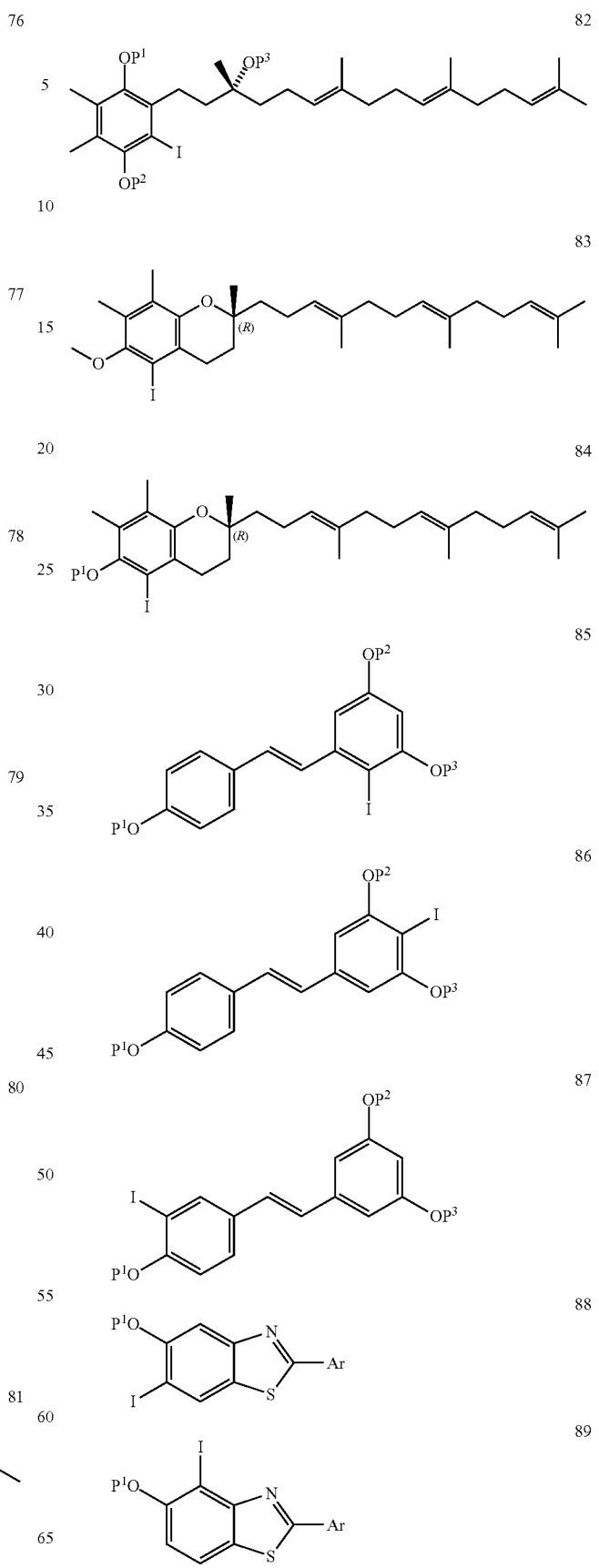

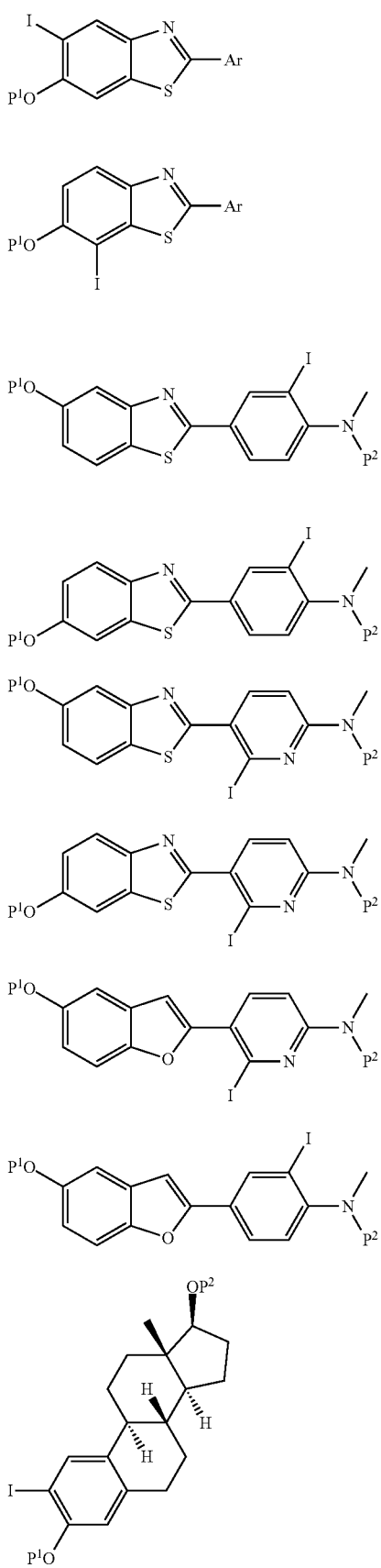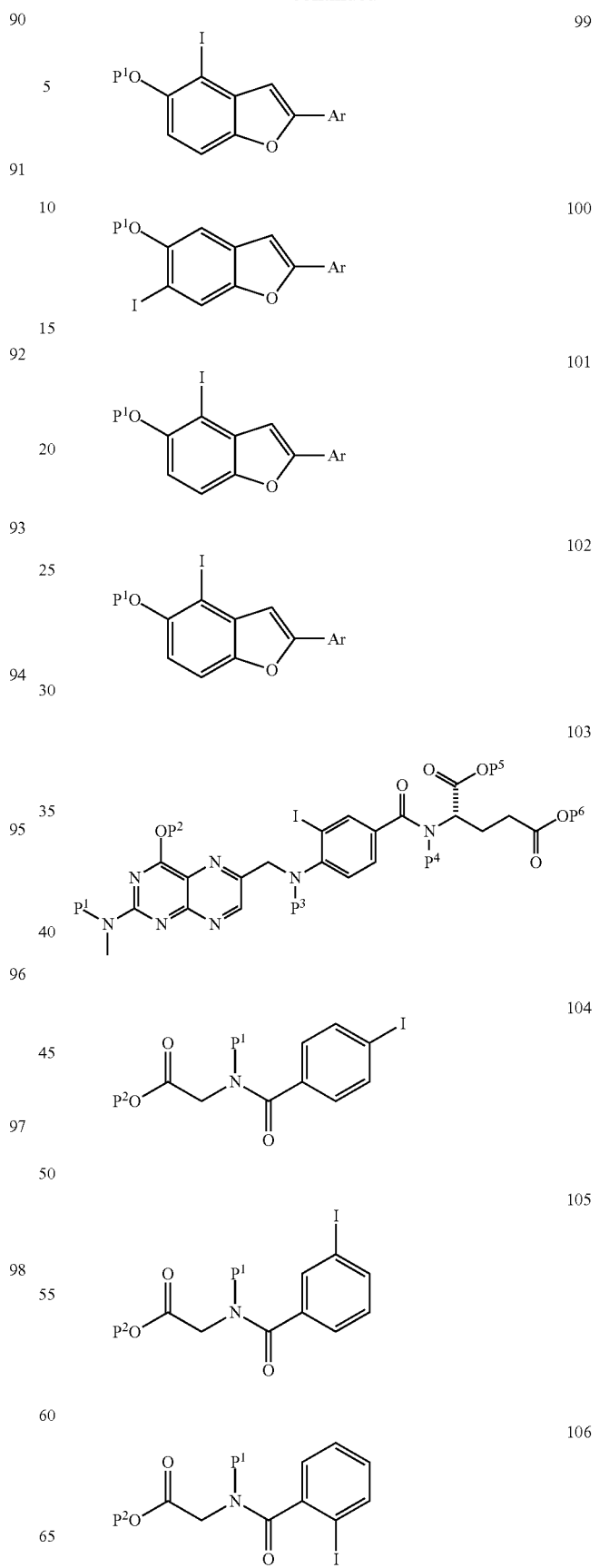

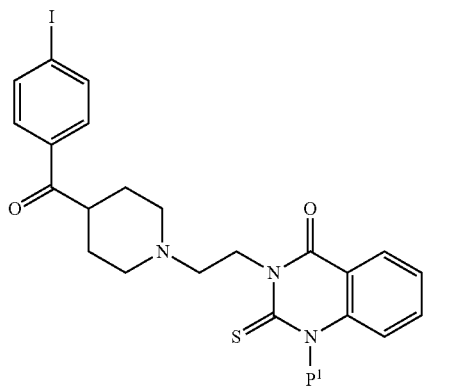

107

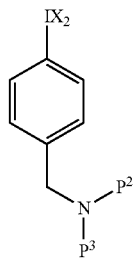

108 wherein Ar is an optionally substituted aryl or heteroaryl, wherein Ar does not have unprotected protic groups; and $P^1$, $P^2$, $P^3$, $P^4$, $P^5$, and $P^6$ are each, independently, protecting groups. In some embodiments, each X is acetate.

In some embodiments, the present application provides a compound of Formula I or a process utilizing a compound of Formula I (e.g., a process of making a compound of Formula III, V, VI, or VII starting from a compound of Formula I; or a process of making a compound of Formula I), wherein the compound of Formula I is selected from any of the following:

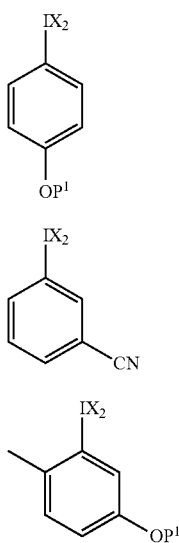

109

110

111

112

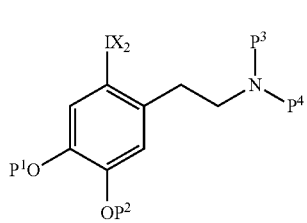

113

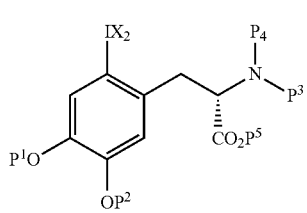

114

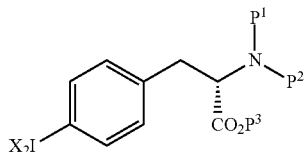

115

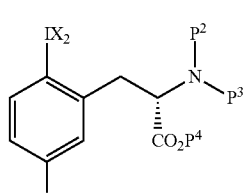

116

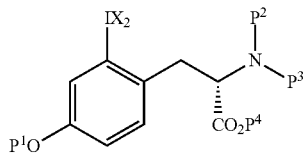

117

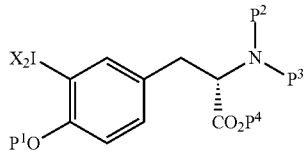

118

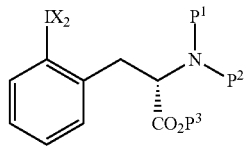

119

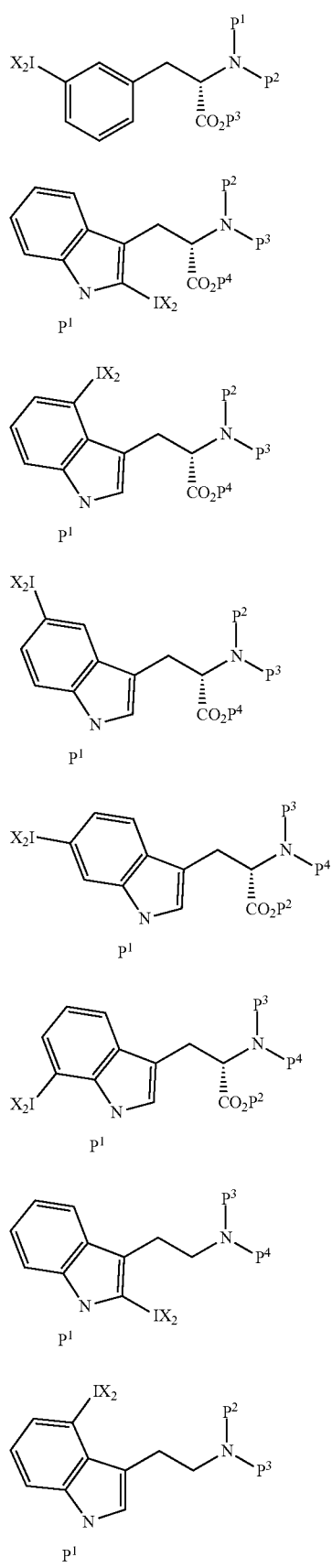
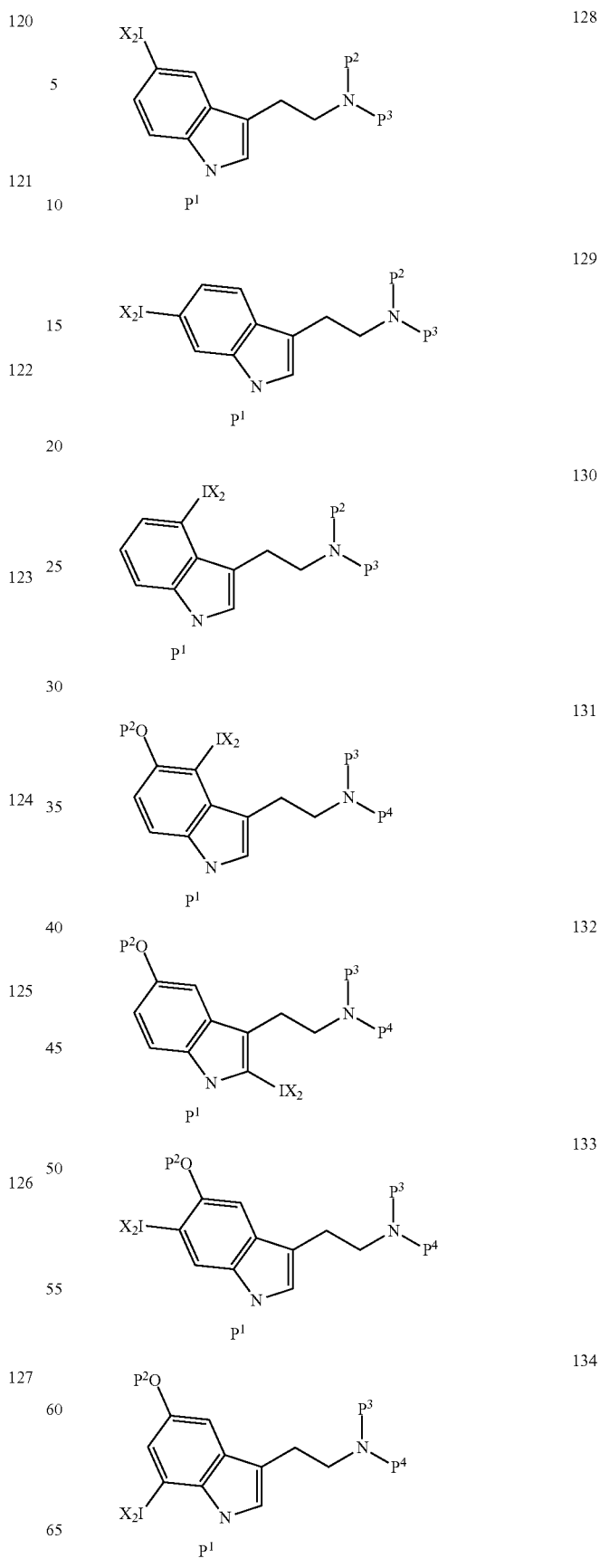

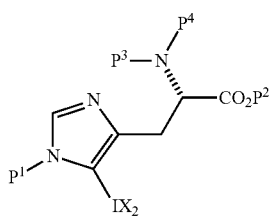
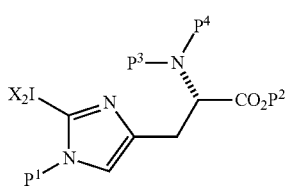
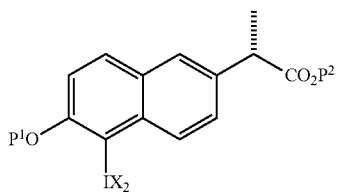
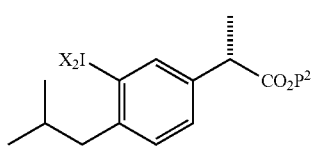
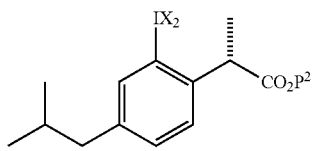
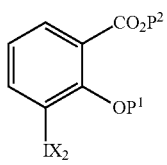
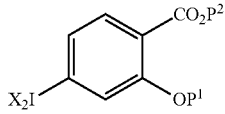
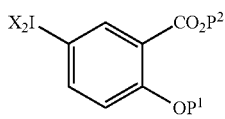
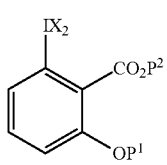
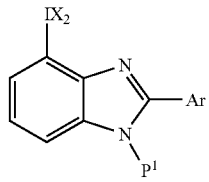
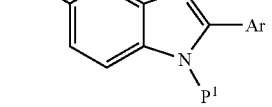
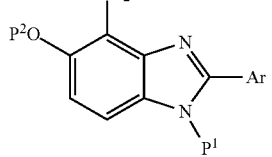
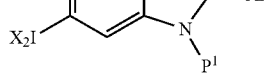
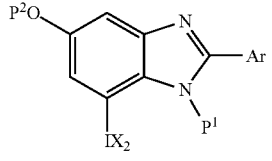
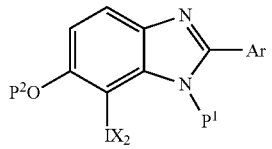
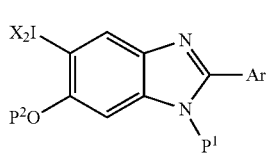
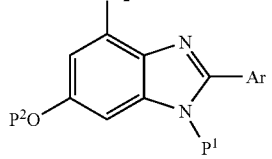

152
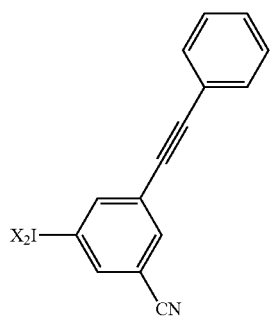
153
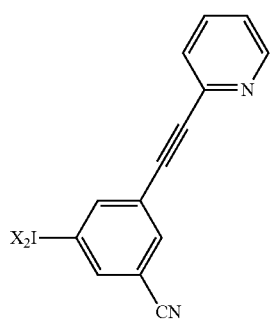
154
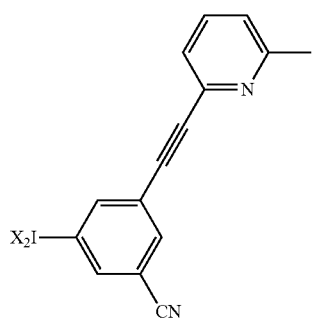
155
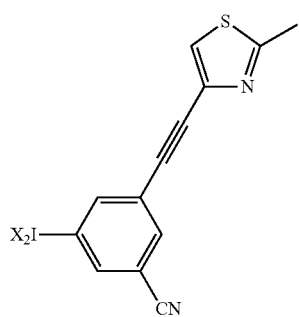
156
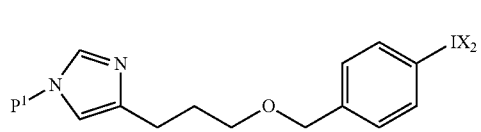
157
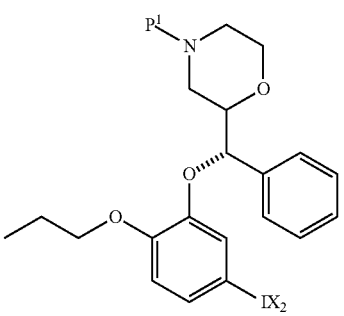
158
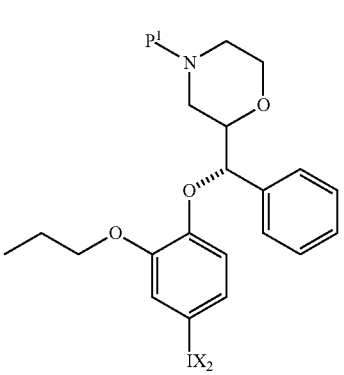
159
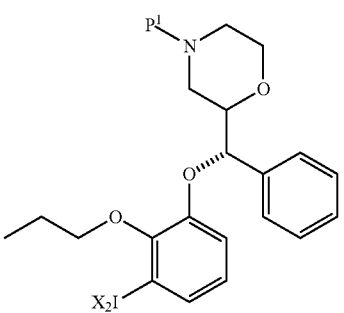
160
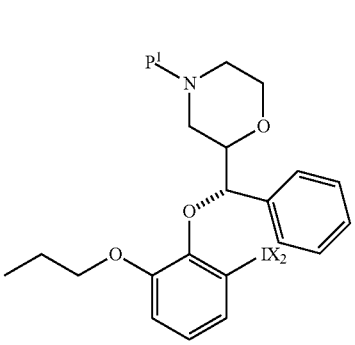
161
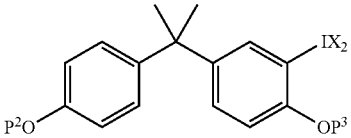

162
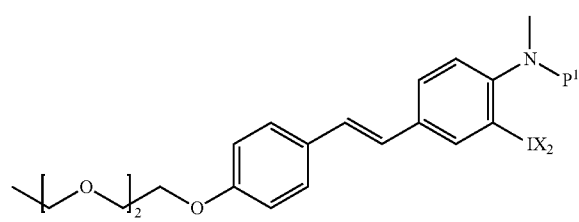
163
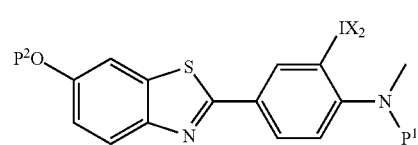
164
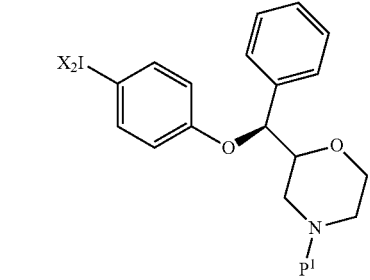
165
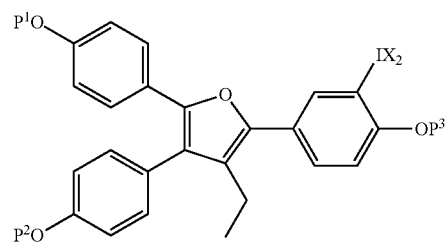
166
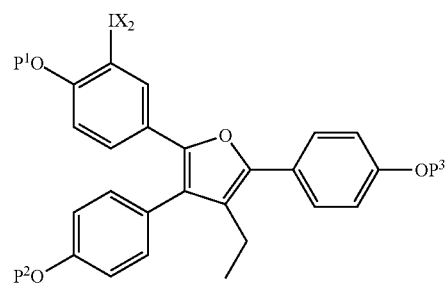
167
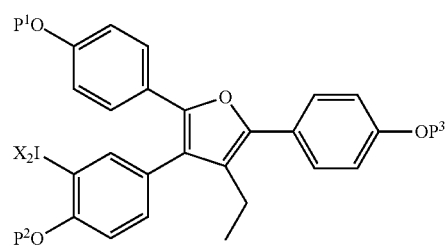
168
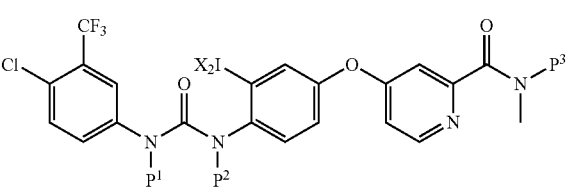
169
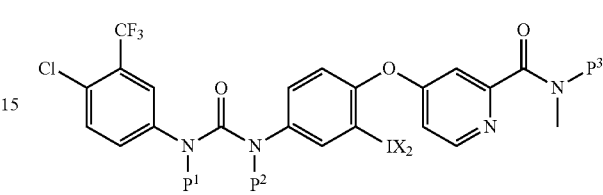
170
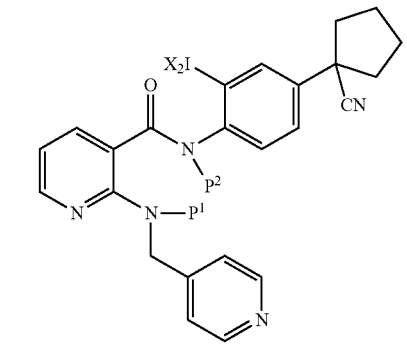
171
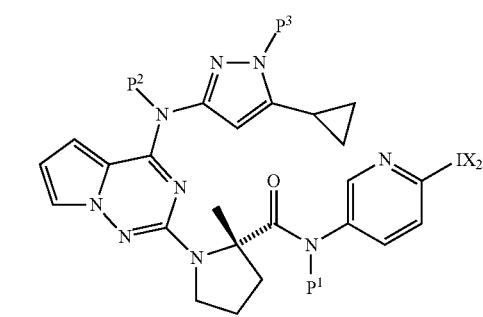
172
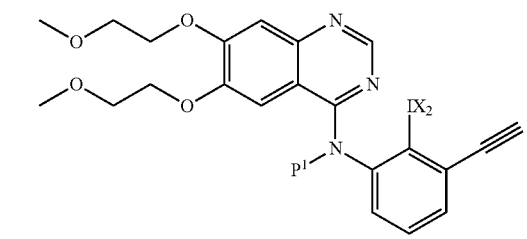
173
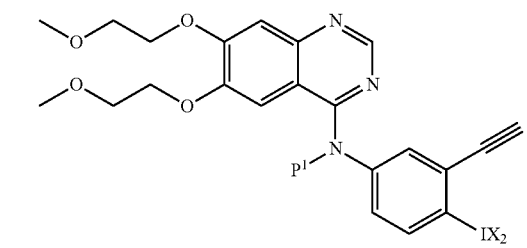

174
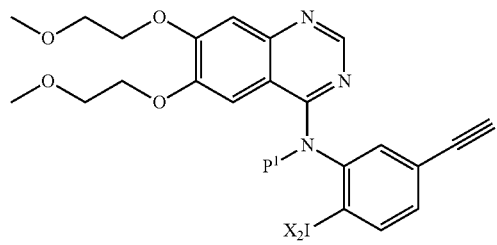
175
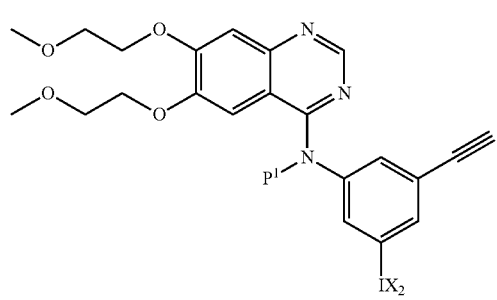
176
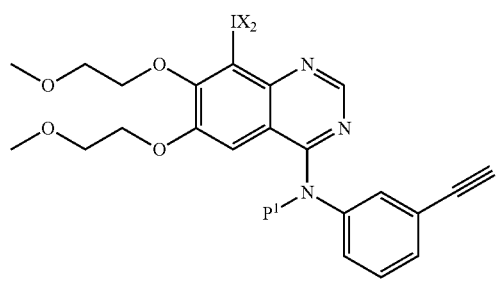
177
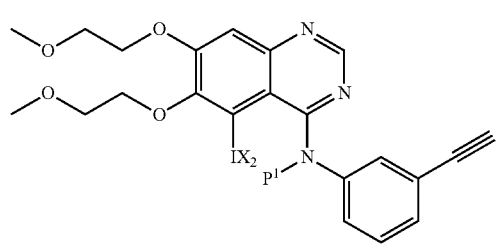
178
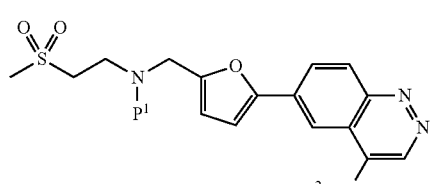
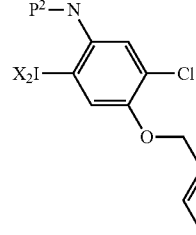
179
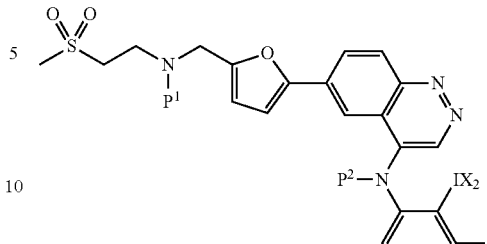
180
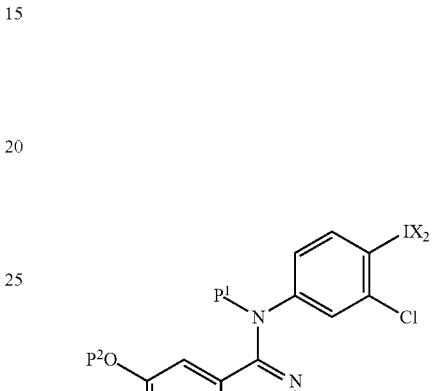
181
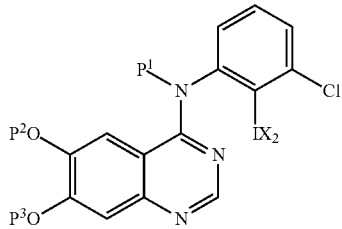
182
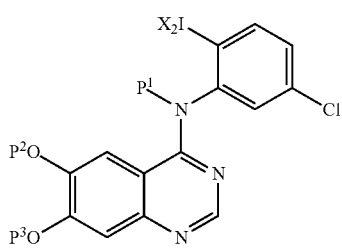
183
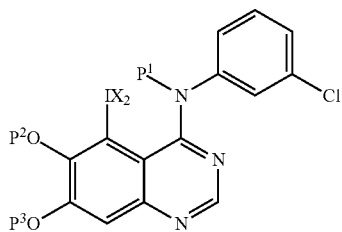

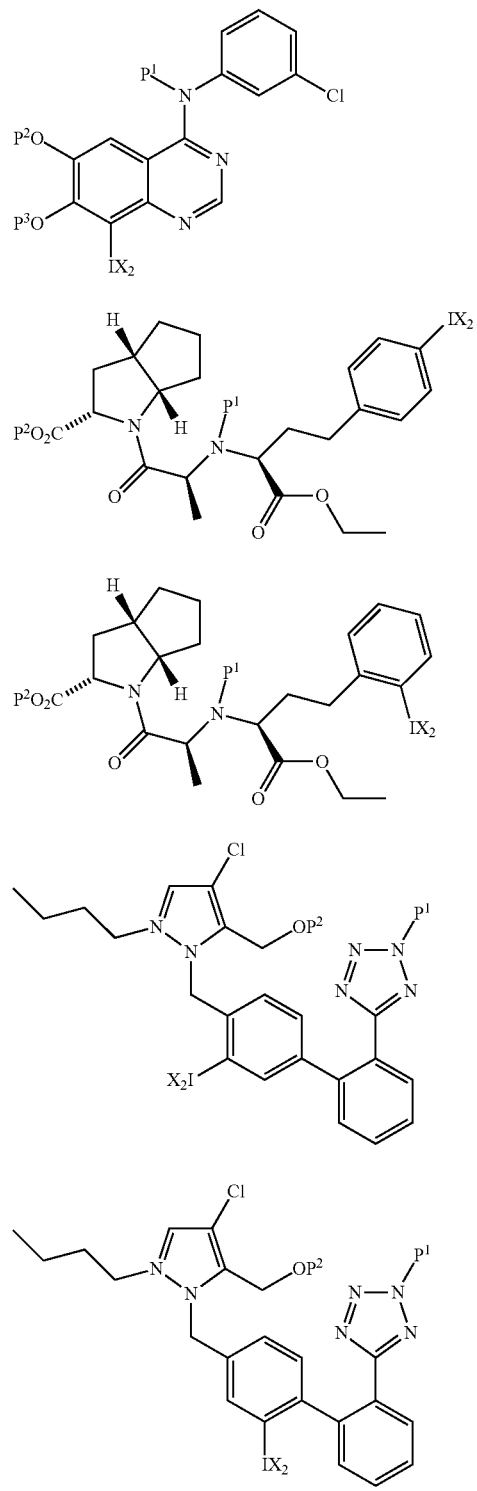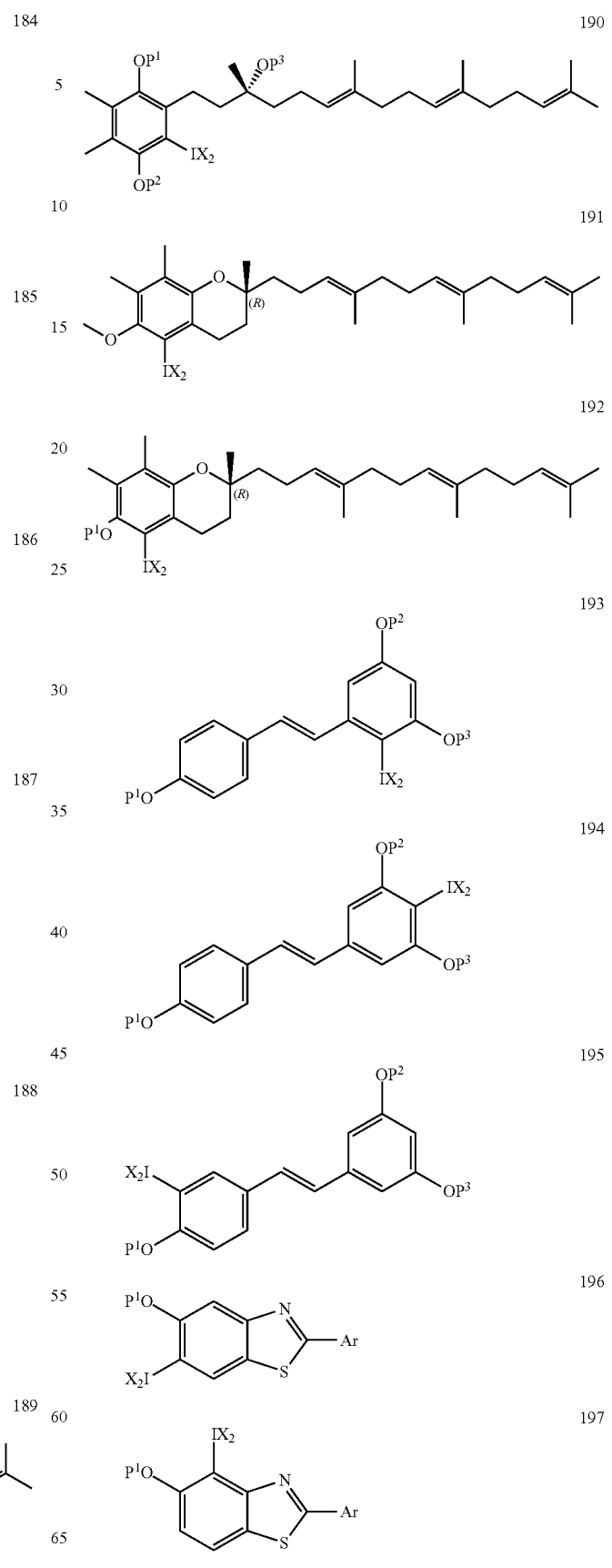

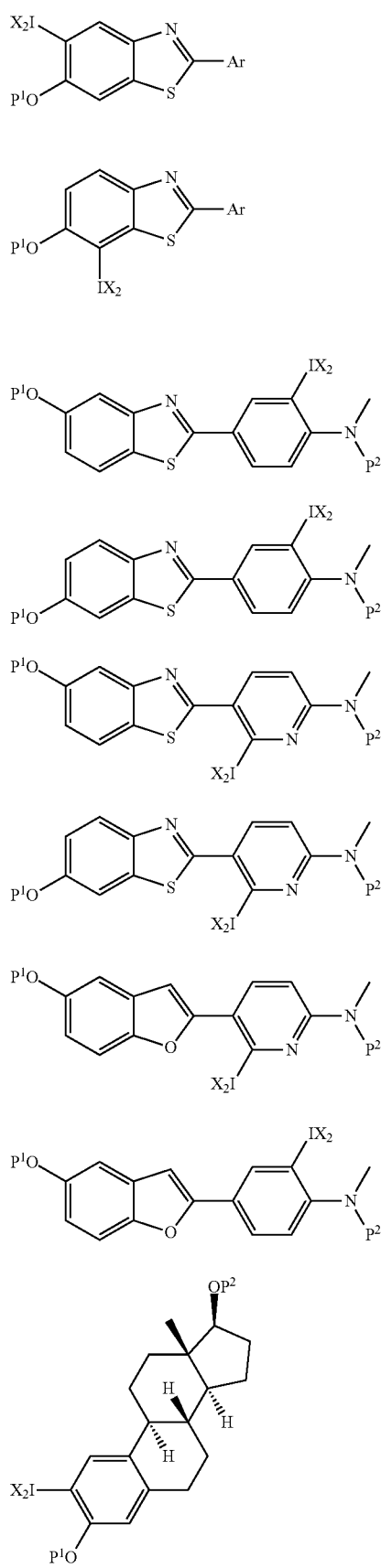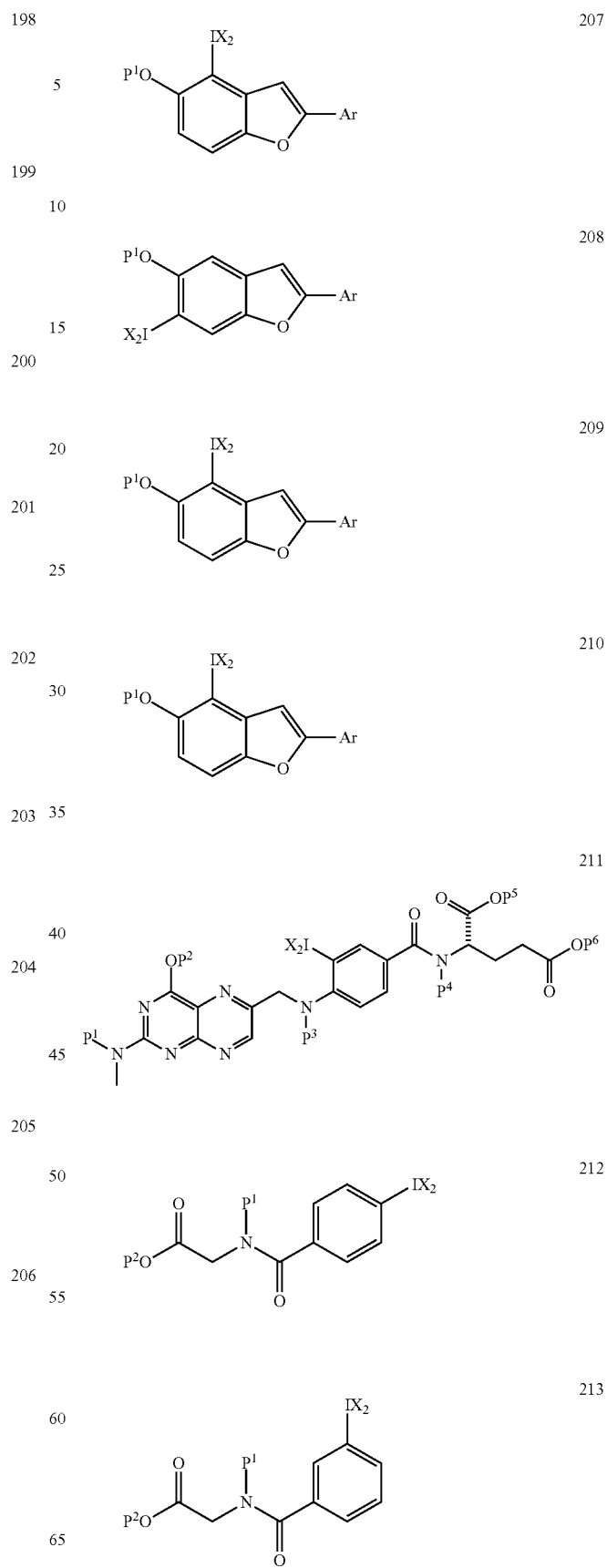

53
-continued

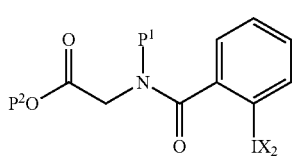
214

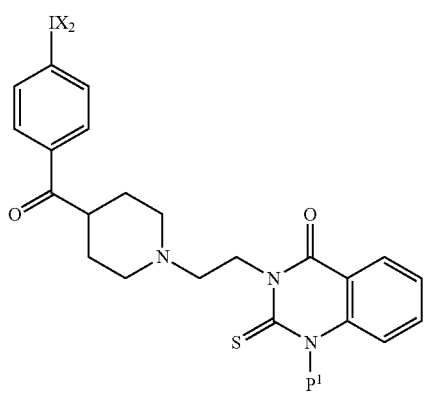

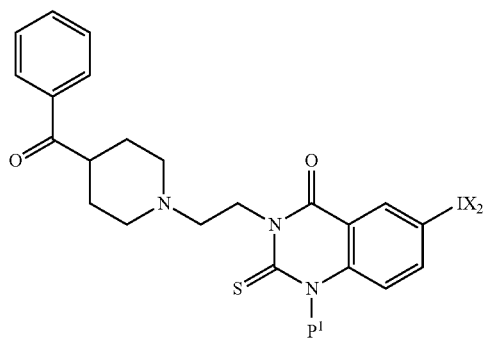
216 wherein Ar is an optionally substituted aryl or heteroaryl, wherein Ar does not have unprotected protic groups; and $P^1$, $P^2$, $P^3$, $P^4$, $P^5$, and $P^6$ are each, independently, protecting groups; and X is defined above. In some embodiments, each X is acetate.

In some embodiments, the present application provides a compound of Formula III or a process involving a compound of Formula III (e.g., a process of making a compound of Formula III or a process of making a compound of Formula, VI, or VII):

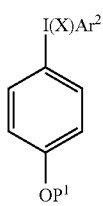
217

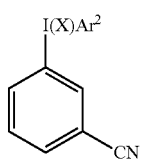
218

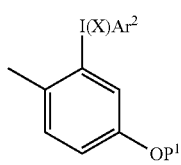
219

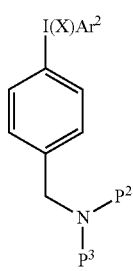
220

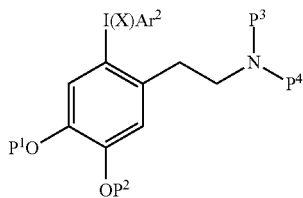
221

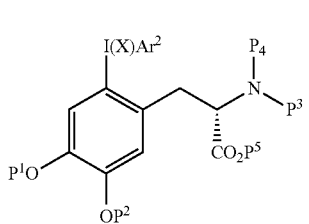
222

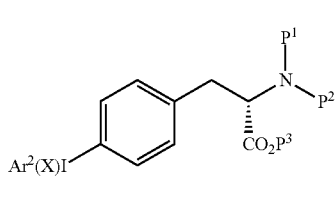
223

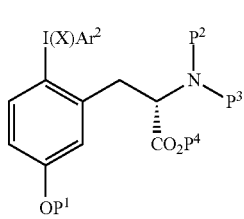
224

| 225 | 226 |
|---|---|
| 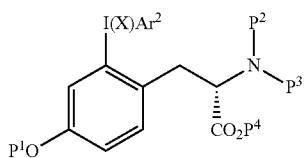 | 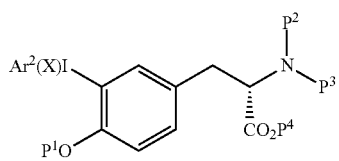 |
| 227 | 228 |
| 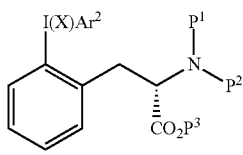 | 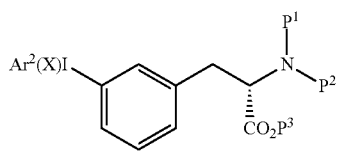 |
| 229 | 230 |
| 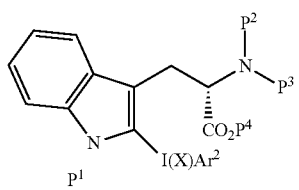 | 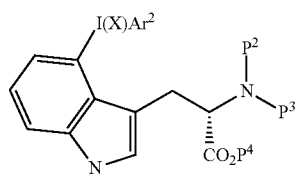 |
| 231 | 232 |
| 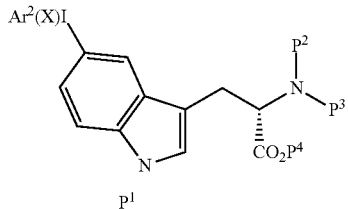 | 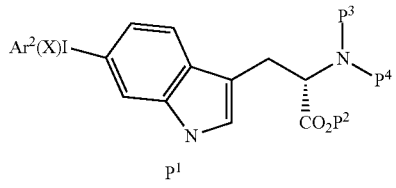 |
| 233 | 234 |
| 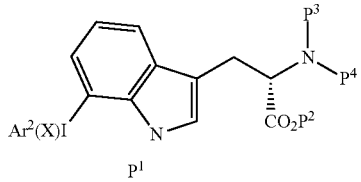 | 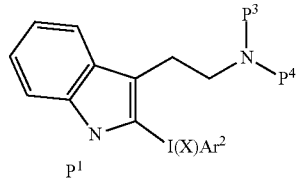 |
| 235 | 236 |
| 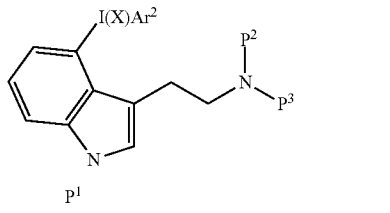 | 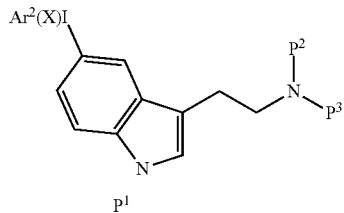 |
| 237 | 238 |
| 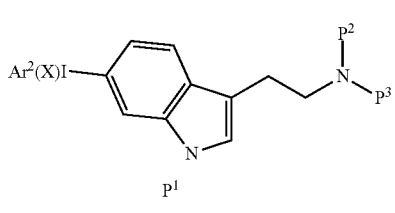 | 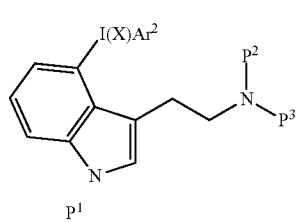 |
| 239 | 240 |
| 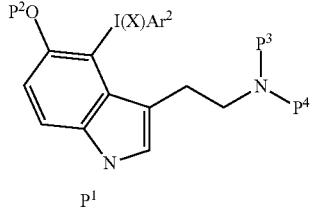 | 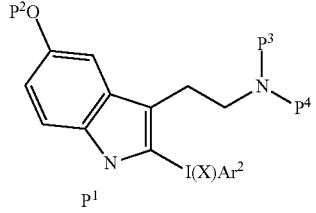 |

-continued
| | |
|---|---|
| 241 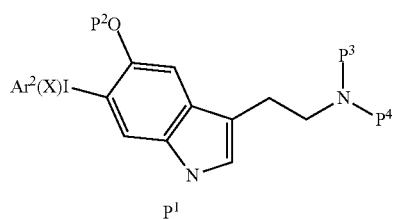 | 242 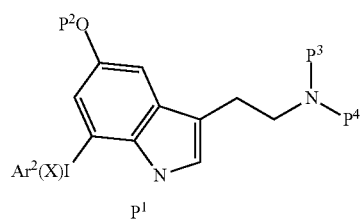 |
| 243 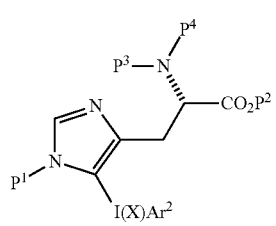 | 244 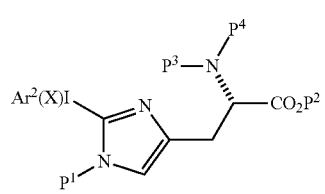 |
| 245 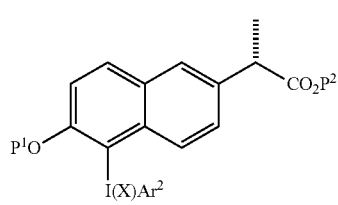 | 246 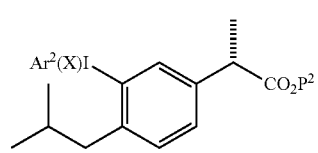 |
| 247 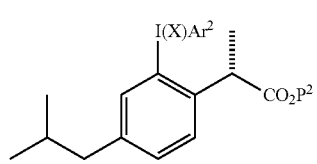 | 248 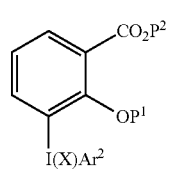 |
| 249 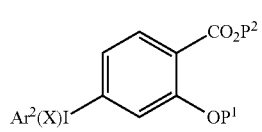 | 250 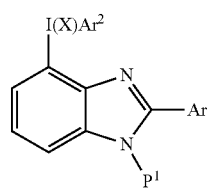 |
| 251 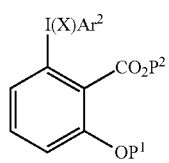 | 252 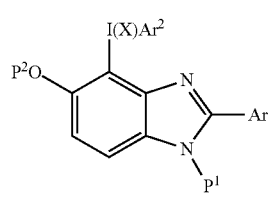 |
| 253 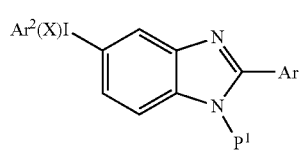 | 254 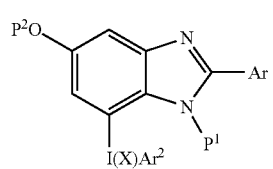 |
| 255 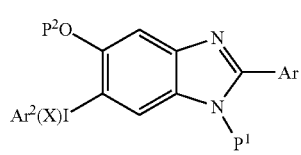 | 256 |

-continued
| 257 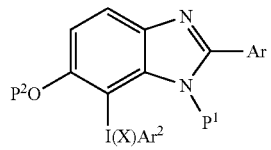 | 258 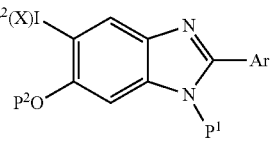 |
| --- | --- |
| 259 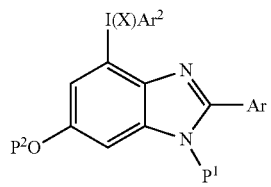 | 260 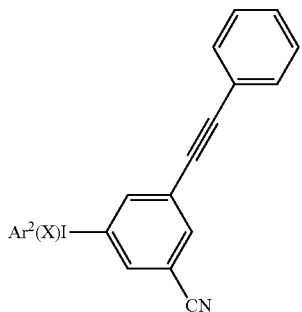 |
| 261 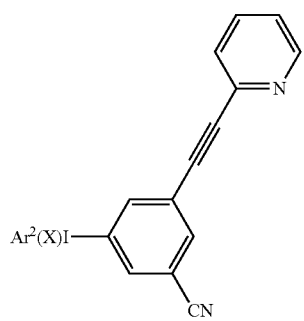 | 262 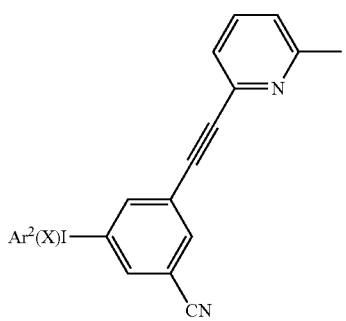 |
| 263 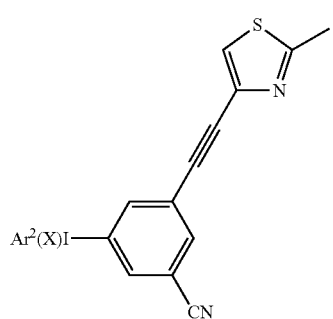 | 264 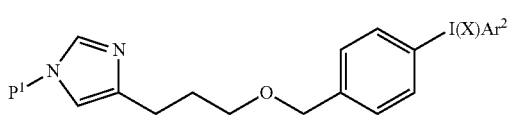 |
| 265 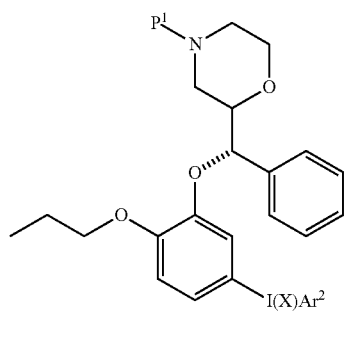 | 266 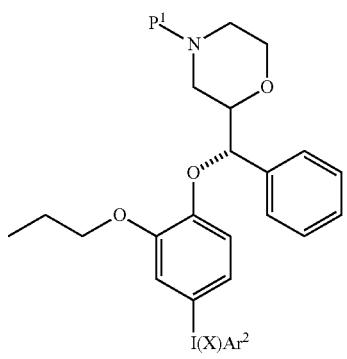 |

-continued
267 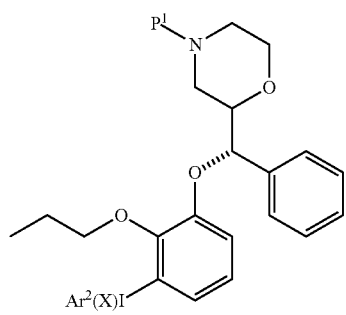
268 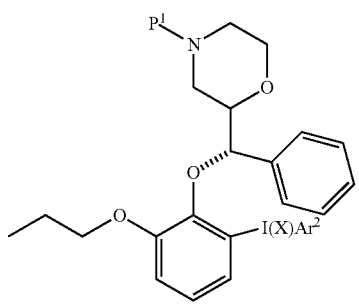
269 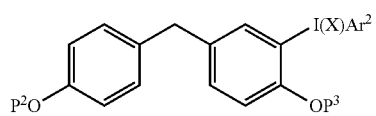
270 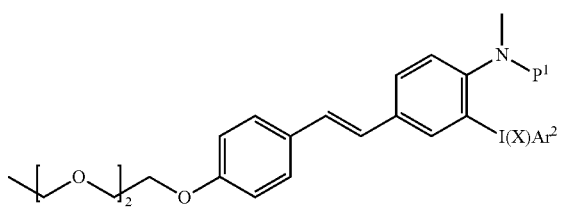
271 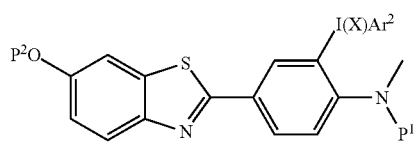
272 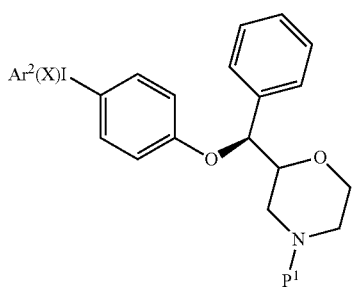
273 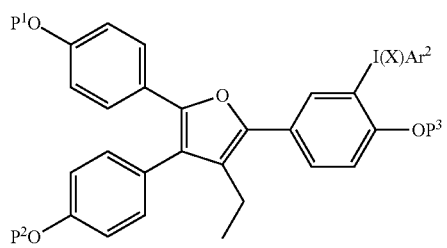
274 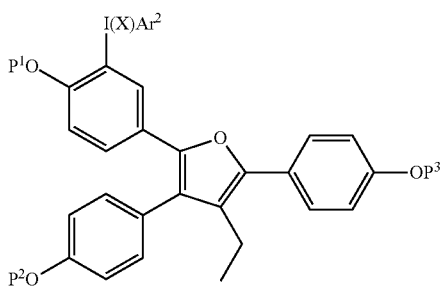
275 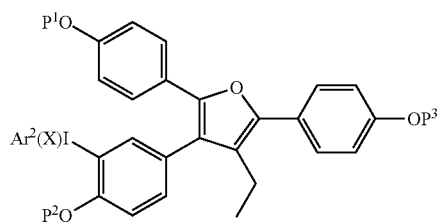
276 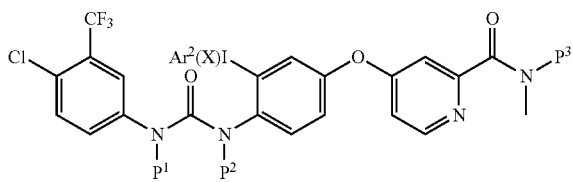

-continued
277
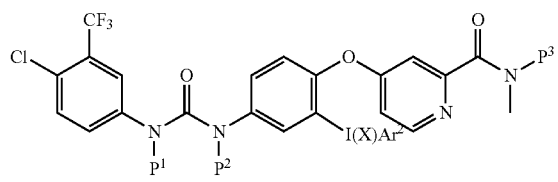
278
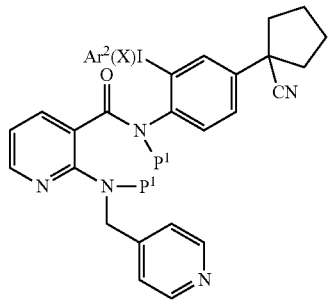
279
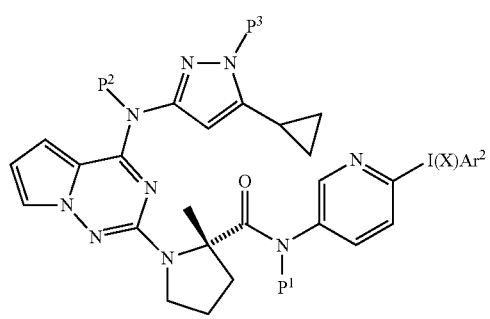
280
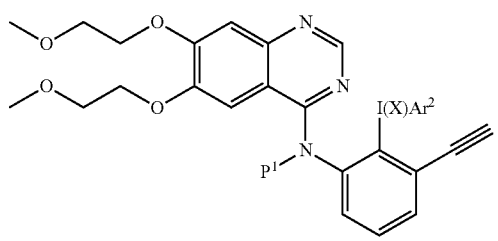
281
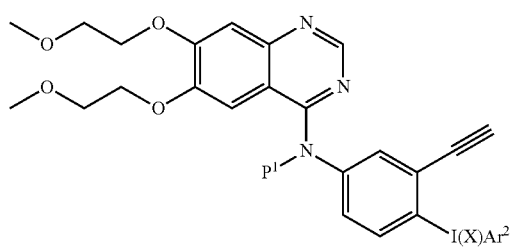
282
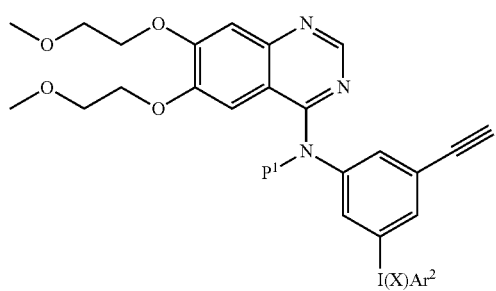
283
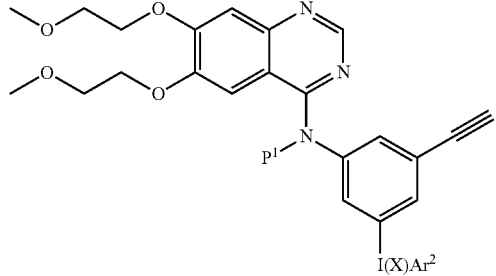
284
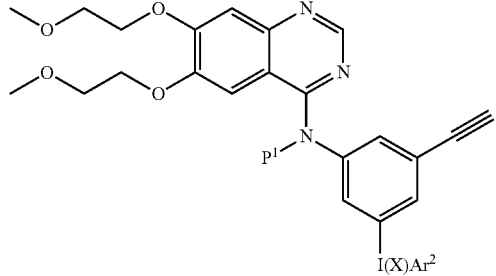
285
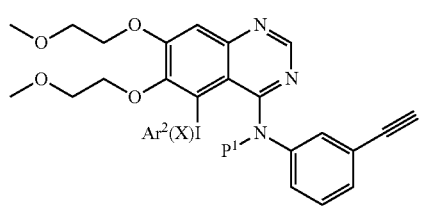
286
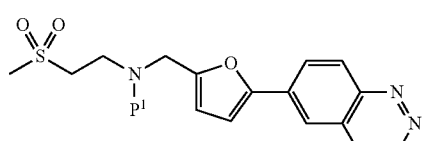

-continued
287 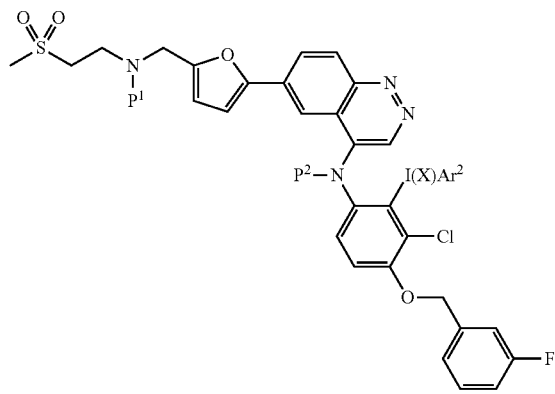
288 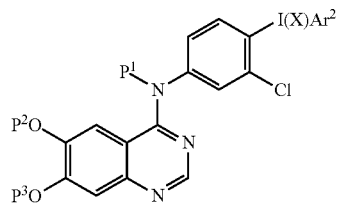
289 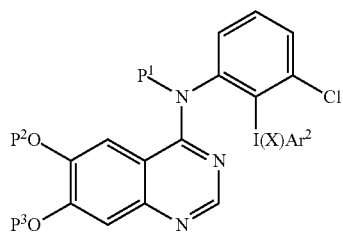
290 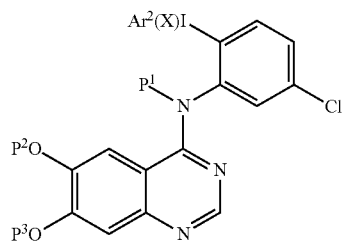
291 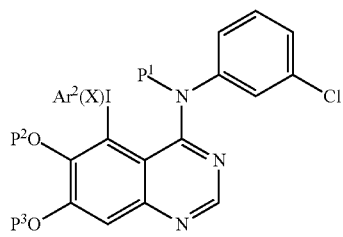
292 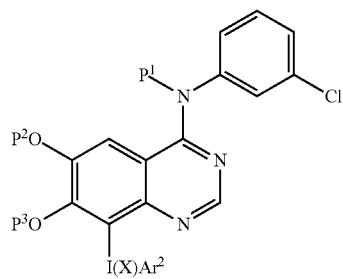
293 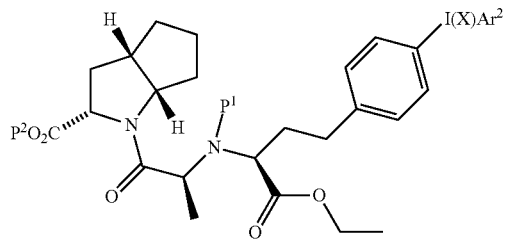
294 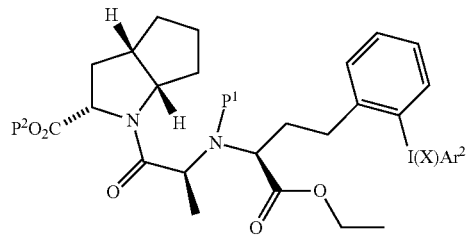
295 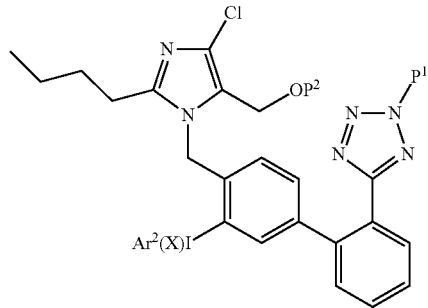
296 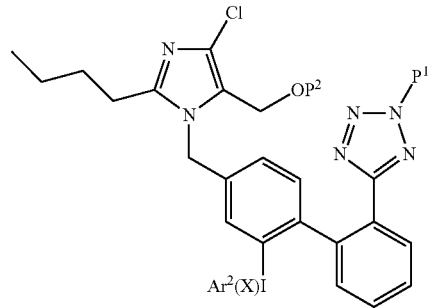

-continued
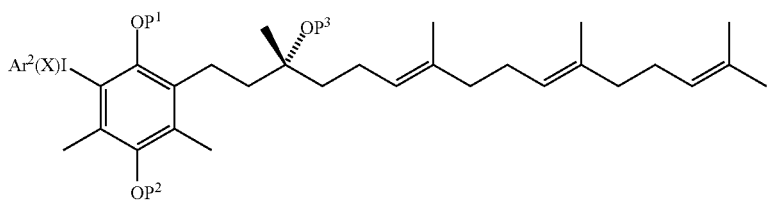
297
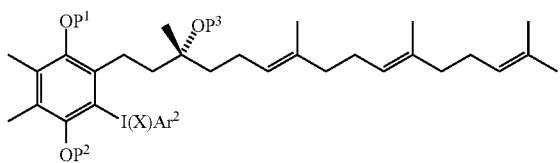
298
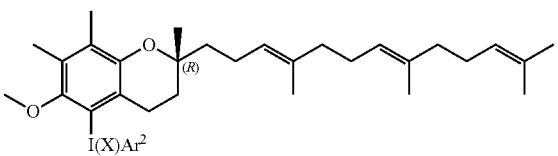
299
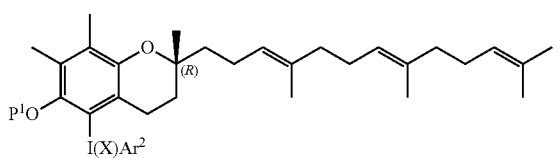
300
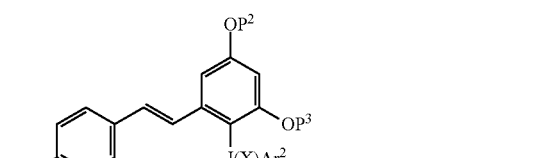
301
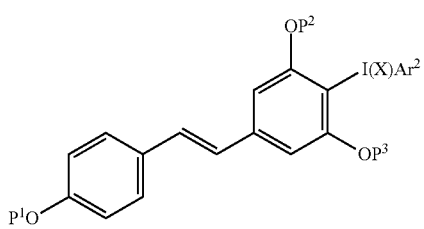
302
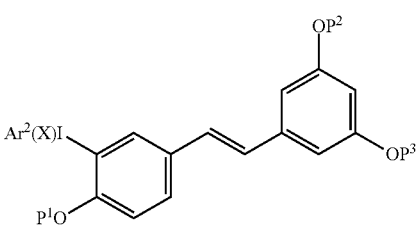
303
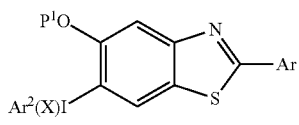
304
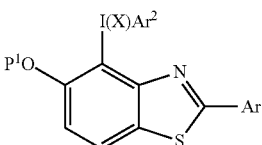
305
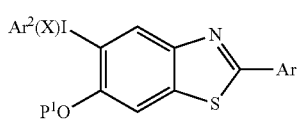
306
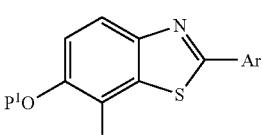
307
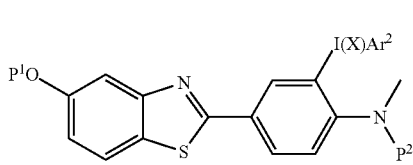
308
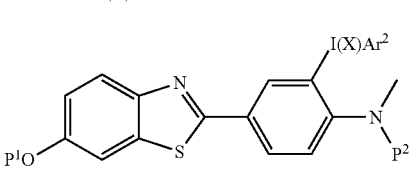
309
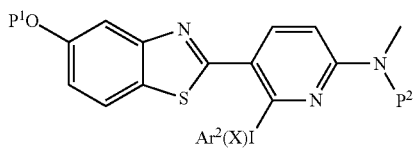
310
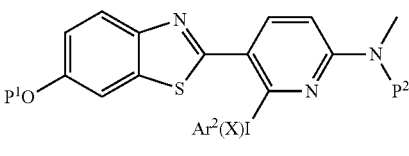
311
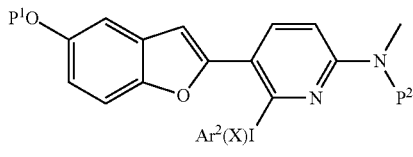
312
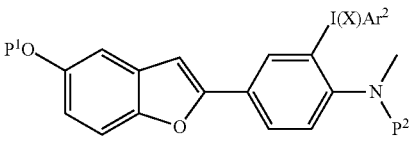
313

-continued
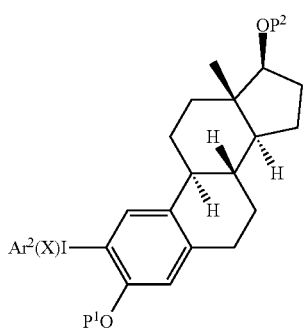 
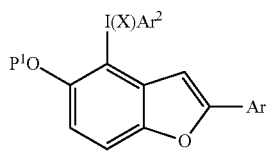 314
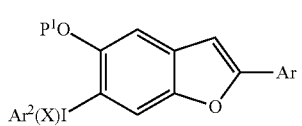 
315
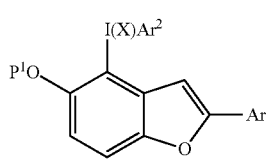 316
317
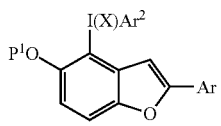 318
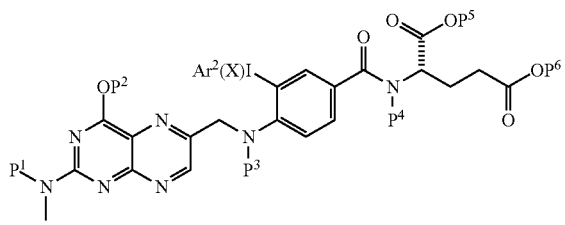 319
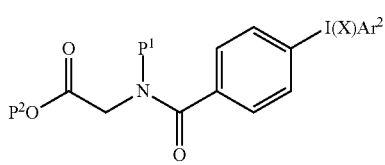 320
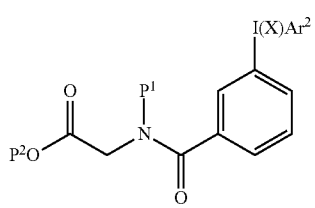 321
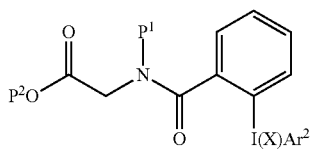 322
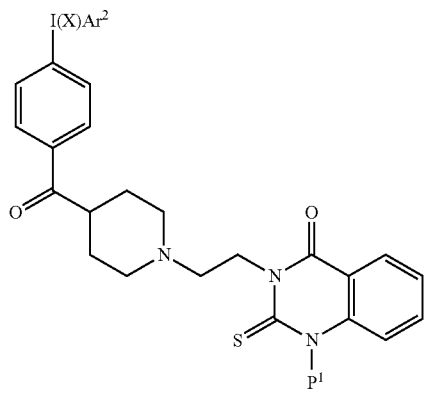 323

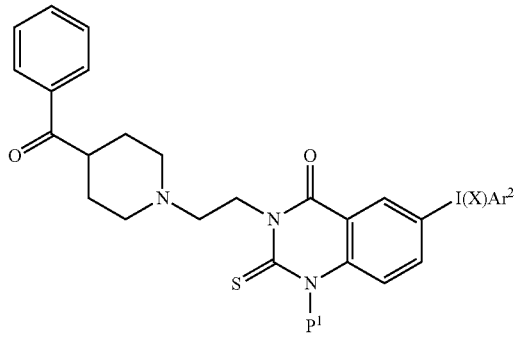

wherein Ar is an optionally substituted aryl or heteroaryl, wherein Ar does not have unprotected protic groups; and $P^1$, $P^2$, $P^3$, $P^4$, $P^5$, and $P^6$ are each, independently, protecting groups; and $Ar^2$ and X are defined above. In some embodiments, each X is acetate. In some embodiments, $Ar^2$ is p-methoxyphenyl. In some embodiments, the present application provides the compound of Formula V corresponding to compounds 217-324, wherein X is replaced by Y. In some embodiments, Y is $PF_6^-$ or triflate.

In some embodiments, the present application provides any of the individual compounds 1-324 disclosed herein. In some embodiments, the present application provides any process described herein utilizing any of compounds 1-324. In some embodiments, the present application provides a compound of Formula VI or VII, or a salt thereof, derived from compounds 217-324. In some embodiments, the compound of Formula VI or VII, or salt thereof, derived from compounds 217-324 has a fluoro atom (e.g. a $^{18}F$ atom) at the position corresponding to W or F in Formulas VI and VII, respectively.

The compounds of Formula III or V can be used to make fluorinated compounds, including $^{18}F$ labeled compounds as described in in US 2011/0313170 and US 2012/0004417, which are incorporated herein by reference in its entirety.

For example, the compounds of Formula III or V can be utilized to prepare compounds of Formula VI:

VI or a salt thereof, wherein $Ar^1$ is as defined above; and W is a moiety wherein the pKa of the acid H—W is less than 12. In one embodiment, the method includes reacting in a polar solvent a compound MW, wherein M is a counter ion and W is as defined in Formula VI and a compound of Formula V:

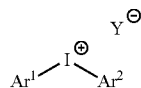

V wherein $Ar^1$ and $Ar^2$ are as defined above; Y is a leaving group; and
W is as defined above.

The polar solvent can then be removed from the reaction mixture. The remaining mixture can then be combined with a nonpolar solvent and heated to produce a compound of Formula VI.

In some embodiments, the method can include heating a mixture comprising a nonpolar solvent, a compound MW, and a compound of Formula V.

In some embodiments, the nonpolar solution of the reaction mixture of MW and a compound of Formula V can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In further embodiments, the nonpolar solution of the reaction mixture of MW and a compound of Formula V can be filtered prior to heating, the nonpolar solvent can be removed (e.g., by evaporation), and the heating of the sample can be performed in a different solvent.

In some embodiments, contaminant salts are removed from the solution of the reaction mixture of MW and a compound of Formula V in the polar or nonpolar solution by chromatography. For example, the contaminant salts can be removed by size exclusion, gel filtration, reverse phase, or other chromatographic method prior to heating.

Substituted aryls and heteroaryls which are prepared using the methods described herein can have an W moiety which includes any moiety in which the pKa of H—W (i.e., the conjugate acid of X) is less than about 12. In some cases, W is a radioactive isotope (e.g., $^{18}F$, $^{123}I$, $^{131}I$, and compounds having $^{32}P$ and $^{33}P$). In some embodiments, W can be chosen from halide, aryl carboxylate, alkyl carboxylate, phosphate, phosphonate, phosphonite, azide, thiocyanate, cyanate, phenoxide, triflate, trifluoroethoxide, thiolates, and stabilized enolates. For example, W can be fluoride, chloride, bromide, iodide, trifluoroacetate, benzoate, and acetate. In some embodiments, X is fluoride. In some embodiments, is a radioactive isotope of fluoride (e.g., $^{18}F$).

Y can be any suitable leaving group. In some embodiments, Y is a weakly coordinating anion (i.e., an anion that coordinates only weakly with iodine). For example, Y can be the conjugate base of a strong acid, for example, any anion for which the pKa of the conjugate acid (H—Y) is less than about 1. For example, Y can be triflate, mesylate, nonaflate, hexaflate, toluene sulfonate (tosylate), nitrophenyl sulfonate (nosylate), bromophenyl sulfonate (brosylate), perfluoroalkyl sulfonate (e.g., perfluoro $C_{2-10}$ alkyl sulfonate), tetraphenylborate, hexafluorophosphate, trifluoroacetate, perfluoroalkylcarboxylate, tetrafluoroborate, perchlorate, hexafluorostibate, hexachlorostibate, chloride, bromide, or iodide. In some embodiments, a slightly more basic leaving group such as acetate or benzoate may be used.

The counter ion M can be any suitable cation for the desired W. The choice of the source of W, and accordingly M, is readily within the knowledge of one of ordinary skill in the art. For example, M can be chosen from an alkali metal, alkaline earth metal and transition metal salts such as, for example, calcium, magnesium, potassium, sodium and zinc salts. Metal cations may also be complexed to cryptands or crown ethers to enhance their solubility and to labilize the W moiety. M can also include organic salts made from quaternized amines derived from, for example, N,N' dibenzylethylenediamine, chloroprocaine, choline, diethanolamine, ethylenediamine, meglumine (N-methylglucamine) and procaine. In some embodiments, M can be a lithium, sodium, potassium, or cesium with cryptands or crown ethers, a tetrasubstituted ammonium cation, or phosphonium cation. When W is fluoride, the choice of fluoride source is also readily within the knowledge of one of ordinary skill in the art. A variety of fluoride sources can be used in the preparation of the fluorinated aryl and heteroaryl compounds as provided herein, including but not limited to NaF, KF, CsF, tetrabutylammonium fluoride, and tetramethylammonium fluoride. In certain instances the choice of fluoride source will depend on the functionality present on the compound of Formula V.

The methods described above can be useful in the preparation of fluorinated aryl and heteroaryl ring systems. For example, the methods can be used to prepare a compound of Formula VII:

$$Ar^1—F \qquad \qquad VII$$

or a salt thereof, wherein $Ar^1$ is an aryl or heteroaryl ring system. In particular, the methods can be used to prepare radiolabeled fluorinated aryl and heteroaryl ring systems (e.g., PET radiotracers). In some embodiments, said F is $^{18}F$. In some embodiments, the method can include reacting in a polar solvent a compound MF and a compound of Formula V. The polar solvent can then be removed from the reaction mixture. The remaining mixture can then be combined with a nonpolar solvent and heated to produce a compound of Formula VII.

In some embodiments, the method can include heating a mixture comprising a nonpolar solvent, a compound MF, and a compound of Formula V.

In some embodiments, the nonpolar solution of the reaction mixture of MF and a compound of Formula V can be filtered prior to heating. The filtration step can remove any insoluble material (e.g., insoluble salts) that remain in the reaction mixture. In some embodiments, the solvent can be removed from the filtrate prior to heating (i.e., the residue can be heated neat).

In some embodiments, the nonpolar solution of the reaction mixture of MF and a compound of Formula V can be filtered prior to heating, the nonpolar solvent can be removed (e.g., by evaporation), and the heating of the sample can be performed in a different solvent.

In some embodiments, contaminant salts are removed from the nonpolar solution of the reaction mixture of MF and a compound of Formula V by chromatography. For example, the contaminant salts can be removed by size exclusion, gel filtration, reverse phase, or other chromatographic method prior to heating.

The therapeutic use of compounds of Formula VI or VII with demonstrated pharmacologic activity in amounts which are suitable for modulation of physiologic or pathologic processes and which, in proportion to the demonstrated clinical benefits, demonstrate acceptable toxicity. In particular, the use of $^{18}F$ radiofluorinated molecules of Formula VII claimed herein as in vivo medical imaging agents is contemplated for the diagnosis of disease, the noninvasive demonstration of physiologic or pathologic processes in vivo, and for the coordinate use of such in vivo radiopharmaceutical agents with structurally analogous nonradioactive molecules to determine i) the presence of receptors for the therapeutic agent in individual subjects so that those individuals with probable response to the therapy can be identified prior to exposure to the drug and/or ii) the amount of administered radiopharmaceutical agent localized in an intended target so that dosage for the nonradioactive analogous therapeutic agent can be determined on a patient by patient basis.

In some embodiments, the compounds are provided as pharmaceutically acceptable salts. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or ACN are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Definitions

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "$C_{n-m}$" indicates a range which includes the endpoints, wherein n and m are integers and indicate the number of carbons. Examples include $C_{1-4}$, $C_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 3 carbon atoms. Examples of alkyl moieties include, but are not limited to, chemical groups such as methyl, ethyl, n-propyl, and isopropyl.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, and propoxy (e.g., n-propoxy and isopropoxy). In some embodiments, the alkyl group has 1 to 3 carbon atoms.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6 or 1 to 4 carbon atoms.

As used herein, the term "aminosulfonyl", employed alone or in combination with other terms, refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonylamino" refers to a group of formula —NHS(O)$_2$N(alkyl)$_2$, wherein each alkyl group independently has n to in carbon atoms. In some embodiments, each alkyl group has, independently, 1 to 6 or 1 to 4 carbon atoms.

As used herein, the term "aminocarbonylamino" refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6 or 1 to 4 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "di($C_{n-m}$-alkyl)carbamyl" refers to a group of formula C(O)N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "amino" refers to a group of formula NH$_2$.

As used herein, the term "$C_{1-6}$ alkyl-O—$C_{1-6}$ alkylene" refers to a group of formula $C_{1-6}$ alkylene-O—$C_{1-6}$ alkyl.

As used herein, the term "$C_{1-6}$ alkyl-NR$^{4a}$—$C_{1-6}$ alkylene" refers to a group of formula $C_{1-6}$ alkylene-NR$^{4a}$—$C_{1-6}$ alkyl.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "arylalkyl" refers to a group of formula-alkylene-aryl. In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is benzyl.

As used herein, the term "carbamyl" refers to a group of formula C(O)NH$_2$.

As used herein, the term "carbonyl", employed alone or in combination with other terms, refers to a —C(O)— group.

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused, bridged or spiro rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form C=O or C=S linkages. In some embodiments, cycloalkyl is $C_{3-12}$ cycloalkyl, which is monocyclic or bicyclic. Examplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula-alkylene cycloalkyl. In some embodiments, cycloalkylalkyl is $C_{3-12}$ cycloalkyl-$C_{1-3}$ alkyl, wherein the cycloalkyl portion is monocyclic or bicyclic. In some embodiments, cycloalkylalkyl is $C_{3-12}$ cycloalkyl-$C_{1-4}$ alkyl, wherein the cycloalkyl portion is monocyclic or bicyclic.

As used herein, "$C_{n-m}$ haloalkoxy" refers to a group of formula O-haloalkyl having n to m carbon atoms. An example haloalkoxy group is $OCF_3$. In some embodiments, the haloalkoxy group is fluorinated only. In some embodiments, the alkyl group has 1 to 6 or 1 to 4 carbon atoms.

As used herein, the term "halo" refers to a halogen atom selected from F, Cl, I or Br.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. The heteroaryl may have one or more C=O or C=S linkages. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen. In some embodiments, heteroarylalkyl is $C_{1-9}$ heteroaryl-$C_{1-4}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused, bridged, or spiro rings) ring systems, including spiro systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a C=O, C=S, S=O, or $S(=O)_2$ group (or other oxidized linkage) or a nitrogen atom can be quaternized. In some embodiments, heterocycloalkyl is 5- to 10-membered $C_{2-9}$ heterocycloalkyl, which is monocyclic or bicyclic and which has 1, 2, 3, or 4 heteroatom ring members independently selected from nitrogen, sulfur and oxygen. Examples of heterocycloalkyl groups include 1,2,3,4-tetrahydro-quinoline, azetidine, azepane, pyrrolidine, piperidine, piperazine, morpholine, thiomorpholine, pyran, and a 2-oxo-1,3-oxazolidine ring.

As used herein, the term "heterocycloalkylalkyl" refers to a group of formula-alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen. In some embodiments, heterocycloalkylalkyl is $C_{2-9}$ heterocycloalkyl-$C_{1-4}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present application that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.
General Procedure for Oxidation of an Iodoarene with F-TEDA-BF$_4$/TMSOAc Under a dry atmosphere of N$_2$, 0.5 mmol of the an aryl iodide (1-105) was dissolved in 3 mL of dry acetonitrile. Trimethylsilyl acetate (165 mg, 1.25 mmol) was added to the solution followed by a solution of F-TEDA-BF$_4$ (220 mg, 0.65 mmol) in an additional 3 mL of dry acetonitrile. The reaction mixture was allowed to stand at room temperature for 3-8 h. Acetonitrile was then removed in vacuo and 3×3 mL dichloromethane were used to extract the remaining mixture. The combined dichloromethane solutions were washed with 4×6 mL aqueous acetate buffer (NaOAc: HOAc=0.5 M: 0.5 M, pH=5) and dried over sodium sulfate. The dichloromethane was removed in vacuo to yield the crude product, which was dissolved in 3 mL of dichloromethane and dripped into 150 mL pentane to precipitate the aryliodonium diacetate products, which were collected by vacuum filtration.

Example 1

1-(Diacetoxyiodo)-4-methoxybenzene (1a)

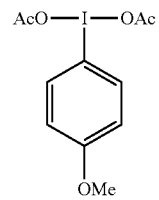

(70%) $^1$H NMR (CD$_3$CN, 400 MHz, 25° C.): δ 8.055 (d, J=9.1 Hz, 2H), 7.053 (d, J=9.1 Hz, 2H), 3.861 (s, 3H), 1.905 (s, 6H); $^{13}$C NMR (CD$_3$CN, 100 MHz, 25° C.) δ 177.73, 163.73, 138.75, 118.00, 111.97, 56.85, 20.76; HRMS: (HR-FAB) calcd. for C$_{14}$H$_{13}$NO$_4$I$^+$[M-2OAc+3-NBA]$^+$ 385.9889 found 385.9885. This compound has been prepared previously: Cerioni, G. and G. Uccheddu, "Solution structure of bis(acetoxy)iodoarenes as observed by 17O NMR spectroscopy", *Tetrahedron Lett.* 2004, 45, 505-507. Characterization data were consistent with the previous literature.

Example 2

3-(Diacetoxyiodo)benzonitrile

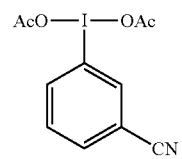 [SMILES: CC(=O)OI(OC(C)=O)c1cccc(C#N)c1]

$^1$H NMR (CD$_3$CN, 400 MHz, 25° C.): δ 8.515 (s, 1H, H2), 8.406 (d, J=8.1 Hz, 1H, H6), 7.866 (d, J=8.1 Hz, 1H, H4), 7.711 (t, J=8.1 Hz, 1H, H5), 1.954 (s, 6H, (OCOCH$_3$)$_2$); $^{13}$C NMR (CD$_3$CN, 100 MHz, 25° C.) δ 178.25 (CO), 140.65 (C6), 139.69 (C2), 136.88 (C5), 132.95 (C4), 121.84 (C3), 115.82 (CN), 109.99 (C1); HRMS (HRFAB): calcd. For C$_{14}$H$_{10}$N$_2$O$_3$I [M-2Oac+3-NBA]+ 380.9736 found 380.9722. (Kazmierczak, P. and L. Skulski, "A simple, two-step conversion of various iodo arenes to (diacetoxyiodo) arenes with chromium(VI) oxide as the oxidant", *Synthesis* 1998, 1721-1723): $^1$H NMR (CDCl$_3$, 200 MHz) δ 7.61-8.39 (4H, m, ArH), 2.02 (6H, s, MeCO$_2$).)

Example 3

2-[2-[(Di-tert-butoxycarbonyl)amino]ethyl]-4,5-dimethoxy-2-iodobenzene

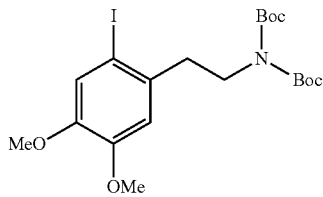 [SMILES: COc1cc(I)c(CCN(C(=O)OC(C)(C)C)C(=O)OC(C)(C)C)cc1OC]

To a solution of N-iodosuccinamide (NIS) (4.95 g, 22 mmol) in dry acetonitrile (50 mL) was added 2-(3,4-dimethoxyphenyl)ethanamine (3.32 mL, 20 mmol) and trifluoroacetic acid (3.85 mL, 50 mmol) with stirring. The mixture was stirred at room temperature in a 250 mL round bottom flask for two hours. The acetonitrile was removed and the remaining solid was taken up in water. The water solution was treated with saturated sodium bisulfite aqueous solution until the purple color disappeared. The pH was adjusted to 8 and the aqueous solution was extracted with dichloromethane (3×50 mL) The organic layers were combined and dried over sodium sulfate. The solvent was evaporated to yield 2-(2-iodo-4,5-dimethoxyphenyl)ethanamine (4.3 g, 70%). The crude product was dried under dynamic vacuum overnight and was sufficiently pure for subsequent steps.

2-(2-iodo-4,5-dimethoxyphenyl)ethanamine (4.3 g) was dissolved in a dry acetonitrile (30 mL) solution containing BOC anhydride (4.84 g, 22 mmol), 4-dimethylpyridine (195 mg, 1.6 mmol), and triethylamine (3.1 mL, 22 mmol). The reaction was stirred overnight at room temperature before being concentrated under reduced pressure. The concentrate was diluted with 30 mL ethyl acetate and washed with saturated $NH_4Cl$ solution, water, and brine. The organic layer was dried over sodium sulfate and concentrated under reduced pressure. The crude product was purified by column chromatography (60 Å silica, 20% ethyl acetate in hexanes, $R_f$=0.3) before subjected to a second round of BOC protection. The purified, BOC-protected 2-(2-iodo-4,5-dimethoxyphenyl)ethanamine was dissolved in 30 mL of an acetonitrile solution containing BOC anhydride (4.36 g, 20 mmol), DMAP (195 mg, 1.6 mmol), and triethylamine (2.78 mL, 20 mmol) and stirred at room temperature for 20 h. The reaction mixture was concentrated in vacuo, diluted with 30 mL ethyl acetate and washed with saturated $NH_4Cl$ solution, water, and brine. The organic layer was dried over sodium sulfate and concentrated under reduced pressure. The crude product was purified by column chromatography (60 Å silica, 15% ethyl acetate in hexanes, $R_f$=0.3) to yield 8.8 g (90%) 2-[2-[(di-tert-butoxycarbonyl)amino]ethyl]-4,5-dimethoxy-2-iodobenzene. $^1H$ NMR ($CD_3CN$, 400 MHz, 25° C.): δ 7.25 (s, 1H), 6.72 (s, 1H), 3.77 (t, J=6.60 Hz, 1H), 3.76 (s, 3H), 3.74 (s, 3H), 2.93 (t, J=6.60 Hz, 1H), 1.41 (s, 18H); $^{13}C$ NMR ($CD_3CN$, 400 MHz, 25° C.): δ 170.9, 153.3, 150.6, 149.6, 135.3, 122.9, 114.7, 88.9, 82.8, 56.8, 56.4, 47.0, 40.1, 28.3; HRMS (HREI): calcd. for $C_{20}H_{30}INO_6M^+$ 507.1118 found 507.1122; calcd. for $C_{20}H_{30}INO_6$ $[M+Na]^+$ 530.1016 found 530.1036.

Example 4

2-[(2S)-2-[(Di-tert-butoxycarbonyl)amino]-3-methoxy-3-oxopropyl]-4,5-dimethoxy-2-iodobenzene

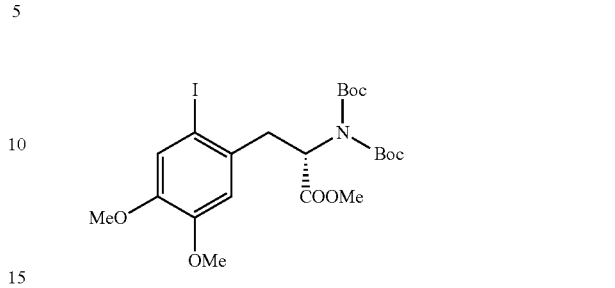

To a solution of N-iodosuccinamide (8.3 g, 37 mmol) in 80 mL of dry acetonitrile were added (S)-3-(3,4-dimethoxyphenyl)1-methoxy-1-oxopropan-2-amine hydrochloride (4.63 g, 16.8 mmol) and trifluoroacetic acid (2.7 mL, 37 mmol) with stirring. The reaction mixture was stirred at room temperature in a 250 mL round bottom flask protected from light for 2 and half hours. The acetonitrile was removed and the remaining solid was taken up into water. The water solution was treated with saturated sodium bisulfite aqueous solution until the purple color disappeared. The pH was adjusted to 8 using saturated sodium bicarbonate solution. The neutralized aqueous solution was extracted with dichloromethane (3×50 mL) The organic layers were combined and dried over sodium sulfate. The solvent was evaporated to yield (S)-3-(2-Iodo-4,5-dimethoxyphenyl)-1-methoxy-1-oxopropan-2-amine (5.17 g, 98%) as a pale yellow oil. The crude product was dried over dynamic vacuum overnight and was sufficiently pure for subsequent steps.

(S)-3-(2-Iodo-4,5-dimethoxyphenyl)-1-methoxy-1-oxopropan-2-amine (5.17 g) was dissolved in a dry acetonitrile (40 mL) solution containing BOC anhydride (7.17 g, 32.9 mmol) and 4-dimethylpyridine (320 mg, 2.63 mmol), triethylamine (4.57 mL, 32.9 mmol). The reaction was stirred overnight at room temperature before being concentrated under reduced pressure. The concentrate was diluted with 40 mL ethyl acetate and washed with saturated $Nff_4Cl$ solution, water, and brine. The organic layer was dried over sodium sulfate and concentrated under reduced pressure. The crude product was purified by column chromatography (60 Å silica, 20% ethyl acetate in hexanes, $R_f$=0.3) before being subjected to a second round of BOC protection. The product was dissolved in 40 mL of an acetonitrile solution containing BOC anhydride (7.17 g, 32.9 mmol), 4-dimethylpyridine (320 mg, 2.63 mmol), triethylamine (4.57 mL, 32.9 mmol) and stirred at room temperature for 20 h. The reaction mixture was concentrated in vacuo, diluted with 40 mL ethyl acetate, and washed with saturated $NH_4Cl$ solution, water, and brine. The organic layer was dried over sodium sulfate and concentrated under reduced pressure. Chromatographic purification (60 Å silica, 15% ethyl acetate in hexanes, $R_f$=0.3) afforded 2-[(2S)-2-[(Di-tert-butoxycarbonyl)amino]-3-methoxy-3-oxopropyl]-4,5-dimethoxy-2-iodobenzene (7.63 g, 82%). $^1H$ NMR ($CD_2Cl_2$, 400 MHz, 25° C.): δ 7.19 (s, 1H), 6.62 (s, 1H), 5.13 (dd, $J_1$=11.2 Hz, $J_2$=4.3 Hz, 1H), 3.77 (s, 3H), 3.76 (s, 3H), 3.74 (s, 3H), 3.44 (dd, $J_1$=14.1 Hz, $J_2$=4.3 Hz, 1H), 3.30 (dd, $J_1$=14.1 Hz, $J_2$=11.2 Hz, 1H), 1.36 (s, 18H); $^{13}C$ NMR ($CD_2Cl_2$, 400 MHz, 25° C.): δ 170.9, 152.3, 149.9, 149.1, 133.1, 122.3, 114.5, 89.2, 83.4, 58.3, 56.6, 56.2, 52.7, 40.6, 28.1; HRMS (HRFAB): calcd. for $C_{22}H_{32}INO_8$ $M^+$565.1173 found 565.1168, calcd. for $C_{22}H_{33}INO_8$ $[M+H]^+$ 566.1251 found 566.1230.

Example 5

2-(Diacetoxyiodo)-1-[2-[(di-tert-butoxycarbonyl)amino]ethyl]-4,5-dimethoxybenzene (5a)

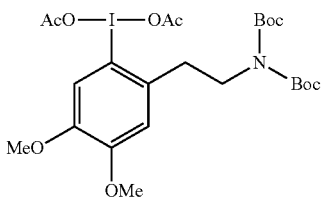 [SMILES: COc1cc(CCN(C(=O)OC(C)(C)C)C(=O)OC(C)(C)C)c(I(OC(C)=O)OC(C)=O)cc1OC]

In a $N_2$ charged glove box, 1 mmol (507 mg) of 2-[2-[(Di-tert-butoxycarbonyl)amino]ethyl]-4,5-dimethoxy-2-iodobenzene was dissolved in 5 mL dry acetonitrile and transferred to a 20 mL high density polyethylene vial. Trimethylsilyl acetate (330 mg, 2.5 mmol) and a solution of F-TEDA-$BF_4$ (439 mg, 1.30 mmol) in 8 mL dry acetonitrile were dropwisely added sequentially. The reaction mixture was allowed to stand at room temperature for 8 h. The reaction solution was placed in a 100 mL Schlenk flask, sealed and removed from the glove box. Acetonitrile was removed by vacuum transfer and the remaining yellow oil was treated with 3 aliquots (5 mL each) of dichloromethane and the aliquots were decanted off of the colorless precipitated salts that remained in the flask. The combined dichloromethane extracts were washed (4×15 mL) with aqueous acetate buffer (NaOAc: HOAc=0.5 M: 0.5 M, pH=5) and dried over sodium sulfate. The dichloromethane was removed in vacuo to yield a pale yellow oil. Pentane (8 mL) was added to the oil and mixture was placed in an ultrasonic bath and sonicated until the salt solidified until. The pentane was decanted away and the remaining light yellow solid was dried under dynamic vacuum for overnight to yield 381 mg (0.61 mmol, 61%) 2-(Diacetoxyiodo)-1-[2-[(di-tert-butoxycarbonyl)amino]ethyl]-4,5-dimethoxybenzene. $^1$H NMR ($CD_3CN$, 400 MHz, 25° C.): δ 7.732 (s, 1H), 7.047 (s, 1H), 3.882 (s, 3H), 3.848 (t, J=7.6 Hz, 2H), 3.830 (s, 3H), 3.120 (t, J=7.6 Hz, 2H), 1.899 (s, 6H), 1.451 (s, 9H); $^{13}$C NMR ($CD_3CN$, 100 MHz, 25° C.) δ 177.6, 153.8, 153.3, 149.8, 136.5, 121.6, 115.9, 113.9, 83.1, 57.1, 56.6, 48.2, 39.1, 28.3, 20.6; HRMS: (HRFAB) calcd. for $C_{26}H_{34}IN_2O_9^+$ [M-2OAc+3-NBA]$^+$ 645.1304 found 645.1312.

Example 6

2-(Diacetoxyiodo)-1-[(2S)-2-[(di-tert-butoxycarbonyl)amino]-3-methoxy-3-oxopropyl]-4,5-dimethoxybenzene (6a)

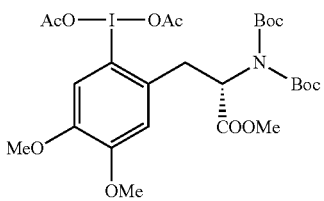 [SMILES: COC(=O)[C@H](Cc1cc(OC)c(OC)cc1I(OC(C)=O)OC(C)=O)N(C(=O)OC(C)(C)C)C(=O)OC(C)(C)C]

In a $N_2$ charged glove box, 1 mmol (565 mg) of 2-[(2S)-2-[(Di-tert-butoxycarbonyl)amino]-3-methoxy-3-oxopropyl]-4,5-dimethoxy-2-iodobenzene was dissolved in 5 mL dry acetonitrile and transferred to a 20 mL high density polyethylene vial. Trimethylsilyl acetate (330 mg, 2.5 mmol) and a solution of F-TEDA-$BF_4$ (439 mg, 1.30 mmol) in 8 mL dry acetonitrile were dropwisely added sequentially. The reaction mixture was allowed to stand at room temperature for 8 h. The reaction solution was placed in a 100 mL Schlenk flask, sealed and removed from the glove box. Acetonitrile was removed by vacuum transfer and the remaining yellow oil was treated with 3 aliquotes (5 mL) of dichloromethane and the aliquots were decanted off of the colorless precipitated salts that remained in the flask. The combined dichloromethane extracts were washed (4×15 mL) with aqueous acetate buffer (NaOAc: HOAc=0.5 M: 0.5 M, pH=5) and dried over sodium sulfate. The dichloromethane was removed in vacuo to yield a pale yellow oil. Pentane (8 mL) was added to the oil and mixture was placed in an ultrasonic bath and sonicated until the salt solidified until. The pentane was decanted away and the remaining light yellow solid was dried under dynamic vacuum for overnight to yield 246 mg (0.36 mmol, 36%) 2-(Diacetoxyiodo)-1-[(2S)-2-[(di-tert-butoxycarbonyl)amino]-3-methoxy-3-oxopropyl]-4,5-dimethoxybenzene. $^1$H NMR ($CD_3CN$, 400 MHz, 25° C.): δ 7.720 (s, 1H), 7.011 (s, 1H), 5.236 (dd, $J_1$=10.4 Hz, $J_2$=3.2 Hz, 1H), 3.864 (s, 3H), 3.821 (s, 3H), 3.728 (s, 3H), 3.676 (dd, $J_1$=14.8 Hz, $J_2$=3.2 Hz, 1H), 3.446 (dd, $J_1$=14.8 Hz, $J_2$=10.4 Hz, 1H), 1.898 (s, 6H), 1.352 (s, 9H); $^{13}$C NMR ($CD_3CN$, 100 MHz, 25° C.) δ 171.3, 153.3, 152.7, 149.9, 134.5, 121.6, 114.3, 84.2, 60.8, 57.2, 56.6, 53.3, 39.5, 28.1, 20.5; HRMS: (HR-FAB) calcd. for $C_{28}H_{36}IN_2O_{11}^+$ [M-2OAc+3-NBA]$^+$ 703.1358 found 703.1365.

Example 7

[2-[2-[(Di-tert-butoxycarbonyl)amino]ethyl]-4,5-dimethoxyphenyl]-(4'-methoxyphenyl)iodonium triflate

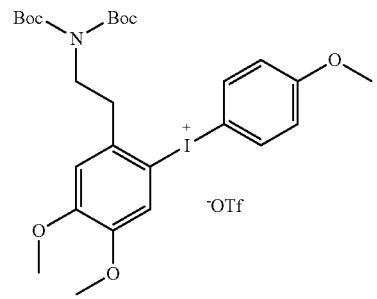

In a $N_2$ charged glove box, 381 mg (0.61 mmol) 2-(diacetoxyiodo)-1-[2-[(di-tert-butoxycarbonyl)amino]ethyl]-4,5-dimethoxybenzene was dissolved in 2 mL dry acetonitrile. A saturated solution of potassium (4-methoxylphenyl)trifluoroborate (130 mg, 0.61 mmol) in 5 mL dry acetonitrile was added to the reaction mixture followed by trimethylsilyl trifluoroacetate (113 mg, 0.61 mmol) solution in 2.5 mL dry acetonitrile. Acetonitrile was then removed in vacuo and dichloromethane (3×4 mL) were used to extract the remaining yellow oil. The combined dichloromethane solutions were washed (3×10 mL) with aqueous acetate buffer (NaOAc: HOAc=0.5 M: 0.5 M, pH=5) and dried over sodium sulfate. Dichloromethane was removed in vacuo to yield a pale yellow oil. The oil was dissolved in 2 mL dry acetonitrile and poured into a 4 mL aqueous solution of sodium hexafluorophosphate (587 mg, 3.5 mmol) precipitating the diaryliodonium hexafluorophosphate salt. The mixture was extracted with dichloromethane (3×5 mL) and the combined organic layers were dried over sodium sulfate, and the solvent was removed under reduced pressure. The crude product was purified by column chromatography (60 Å silica, 40% acetone in hexanes, $R_f$=0.3) to yield 250 mg [2-[2-[(Di-tert-butoxycarbonyl)amino]ethyl]-4,5-dimethoxyphenyl]-(4'-methoxyphenyl)iodonium hexafluorophosphate (250 mg, 0.33 mmol). This compound was dissolved in 1 mL acetonitrile/water (9:1 by volume) solution and slowly passed down an Amberlite IRA-400 ion exchange column (triflate counterion). (The column was prepared for ion exchange by treating the commercially obtained Amberlite IRA-400 (Cl) resin with saturated sodium triflate solution and washing with 10 column volumes of distilled water.) [2-[2-[(Di-tert-butoxycarbonyl)amino] ethyl]-4,5-dimethoxyphenyl]-(4'-methoxyphenyl)iodonium triflate (250 mg, 0.33 mmol) was collected and dried under dynamic vacuum for 20 h. The salt was dissolved dichloromethane (2 mL) and transferred to a 20 mL borosilicate glass vial. Pentane (18 mL) was carefully layered on top of the previous dichloromethane solution. The vial was capped and the sealed container was shielded from ambient light with aluminum foil. Colorless needles formed at the solution interface; these were collected after 20 h. The needles were subjected to a second round of recrystallization using the identical conditions (dichloromethane (2 mL), pentane (18 mL) layering, 20 h in dark) to yield colorless needles of [2-[2-[(di-tert-butoxycarbonyl)amino]ethyl]-4,5-dimethoxyphenyl]-(4'-methoxyphenyl)iodonium triflate (180 mg, 0.24 mmol). The crystals were dried under vacuum and stored in a –40° C. freezer under $N_2$. $^1$H NMR ($CD_3CN$, 400 MHz, 25° C.): δ 8.01 (d, J=9.01 Hz, 2H), 7.56 (s, 1H), 7.04 (d, J=9.01 Hz, 2H), 6.95 (s, 1H), 3.84 (s, 3H), 3.83 (s, 3H), 3.82 (s, 3H), 3.80 (t, J=7.16 Hz, 2H), 3.10 (t, J=7.16 Hz, 2H), 1.44 (s, 18H); $^{13}$C NMR ($CD_3CN$, 100 MHz, 25° C.) δ 164.3, 154.2, 153.8, 151.0, 138.2, 136.6, 120.3, 119.1, 115.2, 107.0, 83.8, 57.3, 56.9, 56.8, 47.4, 38.3, 28.3; $^{19}$F NMR ($CD_3CN$, 400 MHz, 25° C.): δ –79.3 (s, 3F). HRMS: (HREI) calcd. for $C_{27}H_{37}O_7NI$ [M-OTf]$^+$ 614.9165. found 614.1627.

Example 8

[2-[(2S)-2-[(Di-tert-butoxycarbonyl)amino]-3-methoxy-3-oxopropyl]-4,5-dimethoxyphenyl]-(4'-methoxyphenyl)iodonium triflate (6b)

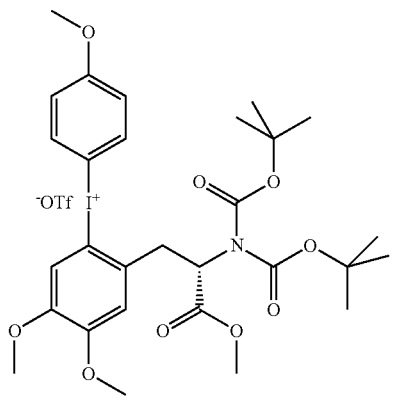 [SMILES: COC(=O)[C@H](Cc1cc(OC)c(OC)cc1[I+]c1ccc(OC)cc1)N(C(=O)OC(C)(C)C)C(=O)OC(C)(C)C ; "-OTf"]

In a $N_2$ charged glove box, 492 mg (0.72 mmol) 2-(diacetoxyiodo)-1-[(2S)-2-[(di-tert-butoxycarbonyl)amino]-3-methoxy-3-oxopropyl]-4,5-dimethoxybenzene was dissolved in 2.5 mL dry acetonitrile. A saturated solution of potassium (4-methoxylphenyl)trifluoroborate (153.4 mg, 0.72 mmol) in 6 mL dry acetonitrile was added to the reaction mixture followed by trimethylsilyl trifluoroacetate (133.4 mg, 0.72 mmol) solution in 1 mL dry acetonitrile. Acetonitrile was then removed in vacuo and dichloromethane (3×5 mL) were used to extract the remaining yellow oil. The combined dichloromethane solutions were washed (3×12 mL) with aqueous acetate buffer (NaOAc: HOAc=0.5 M: 0.5 M, pH=5) and dried over sodium sulfate. Dichloromethane was removed in vacuo to yield a pale yellow oil. Dichloromethane was removed in vacuo to yield a pale yellow oil. The oil was dissolved in 3 mL dry acetonitrile and poured into a 3 mL aqueous solution of sodium hexafluorophosphate (1 g, 6 mmol) precipitating the diaryliodonium hexafluorophosphate salt. The mixture was extracted with dichloromethane (3×6 mL) and the combined organic layers were dried over sodium sulfate, and the solvent was removed under reduced pressure Minimum amount of ethyl acetate was used to rinse off the brown color. Remained oil (200 mg, mmol) was dissolved in a mixture of dichloromethane (2.5 mL) and ethyl acetate (2.5 mL). This solution was transferred to a 20 mL borosilicate glass vial. Pentane (15 mL) was carefully layered on top of the previous solution. Colorless needles formed at the solution interface; these were collected after 20 h. The needles were subjected to a second round of recrystallization using the identical conditions (dichloromethane (2.5 mL), ethyl acetate (2.5 mL), pentane (15 mL) layering, 20 h in dark) to yield colorless needles of [2-[(2S)-2-[(Di-tert-butoxycarbonyl)amino]-3-methoxy-3-oxopropyl]-4,5-dimethoxyphenyl]-(4'-methoxyphenyl)iodonium hexafluorophosphate (120 mg). This compound was dissolved in 1 mL acetonitrile/water (9:1 by volume) solution and slowly passed down an Amberlite IRA-400 ion exchange column (triflate counterion). (The column was prepared for ion exchange by treating the commercially obtained Amberlite IRA-400 (Cl) resin with saturated sodim triflate solution and washing with 10 column volumes of distilled water.) [2-[(2S)-2-[(Di-tert-butoxycarbonyl)amino]-3-methoxy-3-oxopropyl]-4,5-dimethoxyphenyl]-(4'-methoxyphenyl)iodonium triflate (120 mg, 0.14 mmol) was collected and dried under dynamic vacuum for 20 h. The salt was dissolved in a mixture of dichloromethane (3 mL) and ethyl acetate (3 mL) This solution was transferred to a 50 mL borosilicate glass Schlenk tube. Pentane (20 mL) was carefully layered on top of the previous dichloromethane solution. The tube was capped and the sealed container was shielded from ambient light with aluminum foil. Colorless needles foil led at the solution interface; these were collected after 48 h to yield colorless needles of [2-[(2S)-2-[(Di-tert-butoxycarbonyl)amino]-3-methoxy-3-oxopropyl]-4,5-dimethoxyphenyl]-(4'-methoxyphenyl)iodonium triflate (90 mg, 0.11 mmol). The crystals were dried under vacuum and stored in a 40° C. freezer under $N_2$. $^1$H NMR ($CD_2Cl_2$, 400 MHz, 25° C.): δ 7.94 (d, J=8.8 Hz, H2'/H6', 2H), 7.30 (s, H6, 1H), 6.99 (d, J=8.8 Hz, H3'/H5', 2H), 6.93 (s, H3, 1H), 5.10 (dd, $J_1$=7.4 Hz, $J_2$=7.3 Hz, CH, 1H), 3.85 (s, —$OCH_3$, 3H), 3.84 (s, —$OCH_3$, 3H), 3.76 (s, —$OCH_3$, 3H), 3.74 (s, —$COOCH_3$, 3H), 3.62 (dd, $J_1$=14.3 Hz, $J_2$=7.3 Hz, —$CH_2$, 1H), 3.39 (dd, $J_1$=14.3 Hz, $J_2$=7.4 Hz, —$CH_2$, 1H), 1.44 (s, Boc, 18H); $^{13}$C NMR ($CD_2Cl_2$, 400 MHz, 25° C.): δ 171.0 (C=O), 163.7 (C4'), 153.5 (C=O), 152.7 (C4), 150.8 (C5), 137.5 (C2'/C6'), 134.4 (C2), 118.8 (C6), 118.6 (C3'/C5'), 114.6 (C3), 107.6 (C1), 102.7 (C1'), 84.8 (3° C. on Boc), 58.9 (α-C), 57.1 (4-$OCH_3$), 56.6

(5-OCH$_3$), 56.4 (4'-OCH$_3$), 53.4 (COOCH$_3$), 39.9 (β-C), 28.2 (1° C. on Boc); $^{19}$F NMR (CD$_3$CN, 400 MHz, 25° C.): δ −79.3 (s, 3F); HRMS (HRFAB): calcd. for C$_{29}$H$_{39}$INO$_9$ [M-OTf]$^+$ 672.1669, 673.1703 found.

Example 9

[2-[(2S)-2-[(Di-tert-butoxycarbonyl)amino]-3-methoxy-3-oxopropyl]-4,5-dimethoxyphenyl]-[4'-(3,3-dimethylbutoxy)phenyl]iodonium hexafluorophosphate

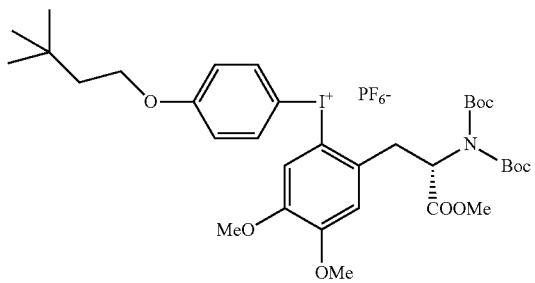

(65%). $^1$H NMR (CD$_3$CN, 400 MHz, 25° C.): δ 7.96 (d, J=9.1 Hz, 2H), 7.41 (s, 1H), 7.04 (d, J=9.1 Hz, 2H), 6.95 (s, 1H), 5.09 (dd, J$_1$=9.3 Hz, J$_2$=5.8 Hz, 1H), 4.10 (t, J=7.2 Hz, 2H), 3.82 (s, 3H), 3.84 (s, 3H), 3.76 (s, 3H), 3.75 (s, 3H), 3.58 (dd, J$_1$=14.7 Hz, J$_2$=5.8 Hz, 1H), 3.39 (dd, J$_1$=14.7 Hz, J$_2$=5.8 Hz, 1H), 1.70 (t, J=7.2 Hz, 2H), 1.38 (s, 18H), 0.97 (s, 9H); $^{13}$C NMR (CD$_3$CN, 100 MHz, 25° C.) δ 171.2, 163.8, 153.9, 153.2, 151.1, 138.4, 135.0, 119.7, 115.6, 107.4, 102.4, 85.0, 67.4, 59.3, 57.2, 56.8, 53.5, 42.7, 39.5, 30.4, 29.9, 28.1; $^{19}$F NMR (CD$_3$CN, 400 MHz, 25° C.): δ −72.9 (d, J=706.2 Hz, 6F). HRMS: (HREI) calcd. for C$_{34}$H$_{49}$INO$_9$PF$_6$ [M-PF$_6$+Na]$^+$ 742.6703 found 742.2457.

General Procedure for One-Pot Syntheses of Diaryliodonium Salts from Aryl Iodides In a N$_2$ charged glove box, 0.5 mmol of an aryl iodide was dissolved in 3 mL dry acetonitrile. Trimethylsilyl acetate (165 mg, 1.25 mmol) was added to the solution followed by a solution of F-TEDA-BF$_4$ (220 mg, 0.65 mmol) in 3 mL dry acetonitrile. The reaction mixture was allowed to stand at room temperature for 3-8 h. A saturated solution of potassium (4-methoxylphenyl)trifluoroborate (117.2 mg, 0.55 mmol) in 6 mL dry acetonitrile was added to the reaction mixture. Acetonitrile was then removed in vacuo and 3×3 mL dichloromethane were used to extract the remaining yellow oil. The combined dichloromethane solutions were washed (4×6 mL) with aqueous acetate buffer (NaOAc: HOAc=0.5 M: 0.5 M, pH=5) and dried over sodium sulfate. The dichloromethane was removed in vacuo to yield the crude product, which was purified by silica gel chromatography and/or crystallization. After recrystallization, the obtained acetate salts were subject to ion exchange to either the hexafluorophosphate or triflate salts. Typically, the acetate salt was dissolved in minimum amount of acetonitrile/water (9:1 by volume) solution and slowly passed down an Amberlite IRA-400 ion exchange column (triflate or hexafluorophosphates counterion). (The column was prepared for ion exchange by treating the commercially obtained Amberlite IRA-400 (Cl) resin with saturated sodium triflate or sodium hexafluorophosphate solution and washing with 10 column volumes of distilled water.) The triflate or hexafluorophosphates salts were collected and dried under dynamic vacuum for 20 h and submitted to recrystallization by layering in mixed solvent systems (dichloromethane and pentane or dichloromethane, ethyl acetate and pentane).

Example 10

Bis(4-methoxyphenyl)iodonium hexafluorophosphate

Recrystallization in a mixture of diethyl ether/dichloromethane gave 391 mg of bis(4-methoxyphenyl)iodonium hexafluorophosphate (80.5%). $^1$H NMR (CD$_3$CN, 400 MHz, 25° C.): δ 7.973 (d, J=9.1 Hz, 4 H, H2/H2'/H6/H6'), 7.046 (d, J=9.1 Hz, 4 H, H3/H3'/H5/H5'), 3.833 (s, 6 H, OMe); $^{13}$C NMR (CD$_3$CN, 100 MHz, 25° C.) δ 164.61 (C4/C4'), 138.55 (C2/C2'/C6/C6'), 119.42 (C3/C3'/C5/C5'), 103.36 (C1/C1'), 57.06 (OMe); $^{19}$F NMR (CD$_3$CN, 376 MHz, 25° C.) δ −72.833 (d, 1JP-F=707.3 Hz, PF$_6$—); HRMS (HRFAB): calcd. for C$_{14}$H$_{14}$O$_2$I [M-PF$_6$]+ 341.0038 found 341.0036.

Example 11

(3,4-Dimethoxyphenyl)(4'-methoxyphenyl)iodonium hexafluorophosphate

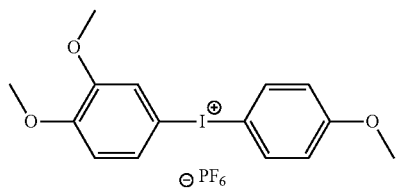

Recrystallization with diethyl ether/dichloromethane gave 370 mg (71.7%) of (3,4-dimethoxyphenyl)(4'-methoxyphenyl)iodonium hexafluorophosphate. $^1$H NMR (CD$_3$CN, 400 MHz, 25° C.): δ7.986 (d, J=9.1 Hz, 2 H, H2'/H6'), 7.647 (dd, J1=8.9 Hz, J2=2.2 Hz, 1 H, H6), 7.558 (d, J=2.2 Hz, 1 H, H2), 7.049 (d, J=9.1 Hz, 2 H, H3'/H5'), 7.022 (d, J=8.9 Hz, 1 H, H5), 1543.845 (s, 3 H, 3-OMe), 3.843 (s, 3 H, 4'-OMe), 3.834 (s, 3 H, 4-OMe); $^{13}$C NMR (CD$_3$CN, 100 MHz, 25° C.) δ 164.58 (C4'), 154.62 (C4), 152.50 (C3), 138.49 (C2'/C6'), 130.65 (C6), 119.38 (C2), 119.13 (C3'/C5'), 115.52 (C5), 103.37 (C1), 102.64 (C1'), 57.49 (3-OMe), 57.14 (4'-OMe), 57.05 (4-OMe); $^{19}$F NMR (CD$_3$CN, 376 MHz, 25° C.) δ −72.786 (d, 1JP-F=705.8 Hz, PF$_6$—); HRMS (HRFAB): calcd. for C$_{15}$H$_{16}$O$_3$I [M-PF$_6$]+ 371.0144 found 371.0156.

Example 12

(2-Methoxyphenyl)(4'-methoxyphenyl)iodonium hexafluorophosphate

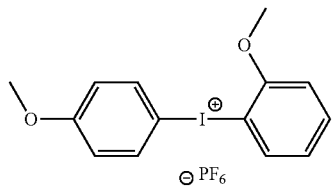

Recrystallization from a mixture of diethyl ether/dichloromethane gave 405 mg (83.3%) of (2-methoxyphenyl)(4'-methoxyphenyl)iodonium hexafluorophosphate. ¹H NMR (CD₃CN, 400 MHz, 25° C.): δ7.988 (d, J=9.2 Hz, 2 H, H2'/H6'), 7.878 (d, J=8.4 Hz, 1 H, H6), 7.659 (td, J1=8.4 Hz, J2=1.3 Hz, 1 H, H4), 7.232 (dd, J1=8.4 Hz, J2=1.3 Hz, 1 H, H5), 7.063 (td, J1=8.4 Hz, J2=1.3 Hz, 1 H, H3), 7.051 (d, J=9.2, 2 H, H3'/H5'), 3.970 (s, 3 H, 2-OMe), 3.841 (s, 3 H, 4'-OMe); ¹³C NMR (CD₃CN, 100 MHz, 25° C.) δ 164.73 (C4'), 157.90 (C2), 139.52 (C2'/C6'), 137.08 (C4), 136.79 (C6), 125.36 (C3), 119.44 (C3'/C5'), 114.70 (C5), 104.69 (C1), 100.92 (C1'), 58.40 (2-OMe), 57.06 (4'-OMe); ¹⁹F NMR (CD₃CN, 376 MHz, 25°C.) δ −72.675 (d, 1JP-F=706.2 Hz, PF₆—); HRMS (HRFAB): calcd. For $C_{14}H_{14}O_2I$ [M-PF₆]+ 341.0038 found 341.0035.

Example 13

(4,5-Dimethoxy-2-methylphenyl)(4'-methoxyphenyl) iodonium hexafluorophosphate

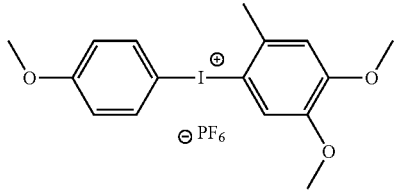

Recrystallization from a mixture of diethyl ether/dichloromethane to give 397 mg (75%) of (4,5-dimethoxy-2-methylphenyl)(4-methoxyphenyl)iodonium hexafluorophosphate. ¹H NMR (CD₃CN, 400 MHz, 25° C.): δ7.939 (d, J=9.2 Hz, 2 H, H2'/H6'), 7.593 (s, 1 H, H6), 7.055 (d, J=9.2 Hz, 2H, H3'/H5'), 7.026 (s, 1 H, H5), 3.835 (s, 6 H, 3/4'-OMe), 3.828 (s, 3 H, 4-OMe), 2.550 (s, 3 H, 2-Me); ¹³C NMR (CD₃CN, 100 MHz, 25° C.) δ 164.45 (C4'), 154.63 (C4), 150.46 (C5), 138.28 (C2'/C6'), 136.71 (C2), 120.59 (C6), 119.41 (C3'/C5'), 115.28 (C3), 107.01
(C1), 102.58 (C1'), 57.51 (3-OMe), 57.14 (4'-OMe), 57.04 (4-OMe); ¹⁹F NMR (CD₃CN, 376 MHz, 25° C.) δ −72.735 (d, 1JP—F=706.9 Hz, PF₆—); HRMS (HRFAB): calcd. For $C_{16}H_{18}O_3I$ [M-PF₆]+ 3385.0301 found 3385.0313

Example 14

Phenyl(4-methoxyphenyl)iodonium hexafluorophosphate

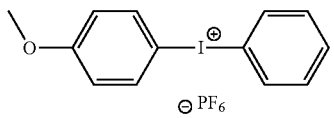

Recrystallization from a mixture of diethyl ether/dichloromethane gave 355 mg (77.9%) of phenyl(4-methoxyphenyl)iodonium hexafluorophosphate. ¹H NMR (CD₃CN, 400 MHz, 25° C.): δ8.022 (d, J=7.6 Hz, 2 H, H2/H6), 8.011 (d, J=9.4 Hz, 2 H, H2'/H6'), 7.701 (t, J=7.6 Hz, 1 H, H4), 7.734 (t, J=7.6 Hz, 2 H, H3/H5), 7.063 (d, J=9.4 Hz, 2 H, H3'/H5'), 3.839 (s, 6 H, OMe); ¹³C NMR (CD₃CN, 100 MHz, 25° C.) δ 164.77 (C4'), 139.04 (C2'/C6'), 136.22 (C2/C6), 134.27 (C4), 133.77 (C3/C5), 119.58 (C3'/C5'), 115.29 (C1), 102.50 (C1'), 57.09 (OMe); ¹⁹F NMR (CD₃CN, 376 MHz, 25° C.) δ −72.754 (d, 1JP-F=707.7 Hz, PF₆—); HRMS (HRFAB): calcd. for $C_{13}H_{12}OI$ [M-PF₆]+ 310.9925 found 310.9932.

Example 15

(3-(Trifluoromethyl)phenyl)(4'-methoxyphenyl)iodonium hexafluorophosphate

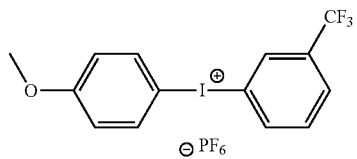

Recrystallization from a mixture of diethyl ether/dichloromethane gave 503 mg (96.1%) of (3-(trifluoromethyl)phenyl)(4'-methoxyphenyl)iodonium hexafluorophosphate. ¹H NMR (CD₃CN, 400 MHz, 25° C.): δ8.384 (s, 1 H, H2), 8.266 (d, J=8.1 Hz, 1 H, H6), 8.056 (d, J=9.2 Hz, 2 H, H2'/H6'), 7.996 (d, J=8.1 Hz, 1 H, H4), 7.716 (t, J=8.1 Hz, 1 H, H5), 7.083 (d, J=9.2, 2 H, H3'/H5'), 3.847 (s, 3 H, 4'-OMe); ¹³C NMR (CD₃CN, 100 MHz, 25° C.) δ 164.99 (C4'), 139.99 (C6), 139.38 (C2'/C6'), 134.44 (C5), 134.281 (q, J=33.6 Hz, C3), 133.08 (q, J=3.7 Hz, C2), 133.05 (q, J=3.7 Hz, C4), 124.11 (q, J=272.8 Hz, CF3), 119.71 (C3'/C5'), 114.83 (C1), 102.54 (C1'), 57.13 (4'-OMe); ¹⁹F NMR (CD₃CN, 376 MHz, 25° C.) δ −63.420 (J1(F—C)=272.8 Hz, J2(F—C)=33.6 Hz, CF₃), −72.625 (d, J1(P—F)=707.1 Hz, PF₆—); HRMS (HRFAB): calcd. for $C_{14}H_{11}OIF_3$ [M-PF₆]+ 378.9807 found 378.9817.

Example 16

(3-Cyanophenyl)(4'-methoxyphenyl)iodonium hexafluorophosphate

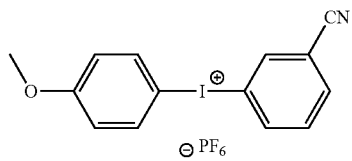

Recrystallization from a mixture of diethyl ether/dichloromethane gave 354 mg (73.7%) of (3-cyanophenyl)(4'-methoxyphenyl)iodonium hexafluorophosphate. ¹H NMR (CD₃CN, 400 MHz, 25° C.): δ 8.389 (t, J=1.6 Hz, 1 H, H2), 8.273 (dd, J1=8.2 Hz, J2=1.6 Hz, 1 H, H6), 8.038 (d, J=9.4 Hz, 2 H, H2'/H6'), 8.017 (dd, J1=8.2 Hz, J2=1.6 Hz, 1 H, H4), 7.665 (t, J=8.2 Hz, 1 H, H5), 7.082 (d, J=9.4, 2 H, H3'/H5'), 3.850 (s, 3 H, 4'-OMe); ¹³C NMR (CD₃CN, 100 MHz, 25° C.) δ 165.04 (C4'), 140.40 (C6), 139.50 (C2), 139.47 (C2'/C6'), 137.79 (C5), 134.13 (C4), 119.75 (C3'/C5'), 117.63 (C3), 116.75 (CN), 114.53 (C1), 102.56 (C1'), 57.16 (4'-OMe); ¹⁹F NMR (CD₃CN, 376 MHz, 25° C.) δ −72.675 (d, 1JP-F=707.5 Hz, PF₆—); HRMS (HRFAB): calcd. for $C_{14}H_{11}NOI$ [M-PF₆]+ 335.9885 found 335.9876.

Example 17

(S)-(4-(3-((4-(tert-butoxycarbonyl)morpholin-2-yl)methoxy)pyridine-2-yloxy)-2-fluorophenyl)(4-methoxyphenyl)iodonium hexafluorophosphate

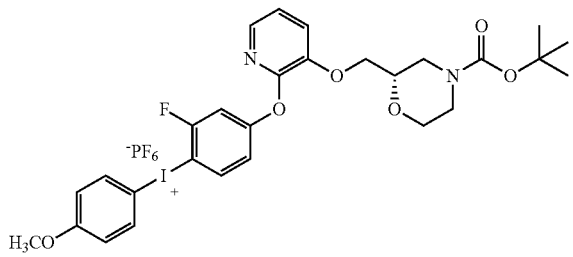

This compound was obtained by slow evaporation of an acetone/hexane solution. Filtration afforded (S)-(4-(3-((4-(tert-butoxycarbonyl)morpholin-2-yl)methoxy)pyridine-2-yloxy)-2-fluorophenyl)(4-methoxyphenyl)iodonium hexafluorophosphate (0.023 g, 68%) as an off-white amorphous solid. $^{19}$F NMR (CD$_3$CN) 376 MHz δ −96.02 (m, 1F), α −72.89 (d, J=703.1 Hz, 6F). $^1$H NMR (CD$_3$CN) 400 MHz δ 1.425 (s, 9H), δ 2.499 (s, 1H), δ 2.815 (s, 1H), δ 3.389 (td, J$_1$=2.8 Hz, J$_2$=11.6 Hz, 1H), δ 3.581 (m, 1H), δ 3.737 (m, 2H), δ 3.844 (s, 3H), δ 4.019 (m, 2H), δ 7.054 (dd, J$_1$=2.7 Hz, J$_2$=8.8 Hz, 1H), δ 7.054 (d, J=9.2 Hz, 2H), δ 7.134 (dd, J$_1$=4.8 Hz, J$_2$=8.0 Hz, 1H), δ 7.238 (dd, J$_1$=4.7 Hz, J$_2$=8.2 Hz, 1H), δ 7.489 (dd, J$_1$=1.6 Hz, J$_2$=8.2 Hz, 1H), δ 7.810 (dd, =1.6, J$_2$=4.9 Hz, 1H). δ 8.023 (d, J=9.2 Hz, 2H), δ 8.081 (dd, J$_1$=6.95 Hz, J$_2$=8.97 Hz, 1H). $^{13}$C NMR (CD$_3$CN) 125 MHz δ 28.93, 45.23, 45.84, 57.09, 67.29, 70.72, 74.51, 80.97, 94.42, 103.35, 108.93, 119.52, 123.71, 124.08, 138.98, 139.08, 139.86, 139.88, 146.04, 155.93, 162.31, 163.07, 164.75. HRMS (HRFAB) calcd. for C$_{28}$H$_{31}$FIN$_2$O$_6$ [M+H]$^+$ 637.1204. found 637.1206.

Example 18

(5-(4-((3R,4R)-4-(ethoxycarbonyl)-1-oxo-2-propyl-1,2,3,4-tetrahydroisoquinolin-3-yl)phenoxy)-2-fluorophenyl)(4-methoxyphenyl)iodonium hexafluorophosphate

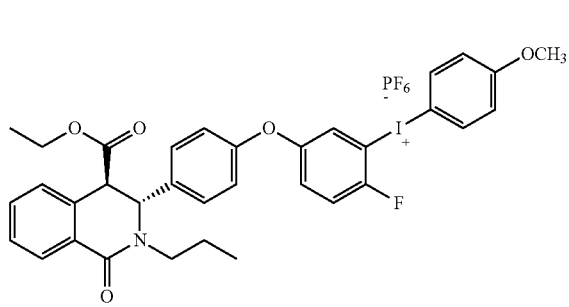

This material was obtained by evaporation of an acetone/hexane solution. Filtration afforded (5-(4-((3R,4R)-4-(ethoxycarbonyl)-1-oxo-2-propyl-1,2,3,4-tetrahydroisoquinolin-3-yl)phenoxy)-2-fluorophenyl)(4-methoxyphenyl) iodonium hexafluorophosphate (15.5 mg, 33.7%) as an off-white amorphous solid. $^{19}$F NMR (CD$_3$CN) 376 MHz δ −106.18 (m, F), δ −72.98 (d, J=707 Hz, PF$_6$). $^1$H NMR (CD$_3$CN) 400 MHz δ 0.8790 (t, J=7.2 Hz, 3H), δ 1.203 (t, J=7.2 Hz, 2H), δ 1.602 (m, 2H), δ 2.755 (ddd, J=5.2, 8.8, 13.7 Hz, 1H), δ 3.839 (s, 3H), δ 3.989 (ddd, J=7.1, 8.8, 13.4 Hz, 1H), δ 4.065 (d, J=1.7 Hz, 1H), δ 4.141 (quar., J=7.2 Hz, 1H), δ 4.144 (quar., J=7.2 Hz, 1H), δ 5.352 (d, J=1.7 Hz, 1H), δ 6.821 (d, J=8.8 Hz, 2H), δ 7.005 (d, J=9.2 Hz, 2H), δ 7.083 (d, J=8.8 Hz, 2H), δ 7.175 (m, 1H), δ 7.225 (m, 1H), δ 7.406 (m, 1H), δ 7.425 (m, 2H), δ 7.622 (dd, J=1.1, 3.0 Hz, 1H), δ 7.948 (d, J=9.2 Hz, 2H), δ 8.011 (m, 1H).

Example 19

(3-Cyano-5-((2-methylthiazol-4-yl)ethynyl)phenyl)(4-methoxyphenyl)iodonium hexafluorophosphate

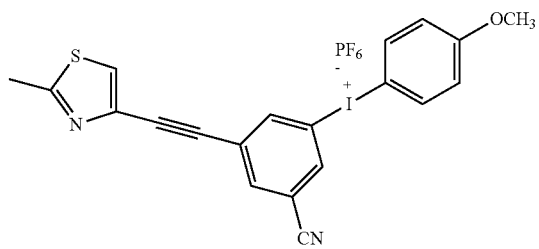

Recrystallization from acetone/hexane yielded 0.070 g (40%) of a colorless solid. $^1$H NMR (CD$_3$CN) 400 MHz δ 2.684 (s, 3H), δ 3.858 (s, 3H), δ 7.0945 (d, J=9.2 Hz, 2H), δ 7.701 (s, 1H), δ 8.057 (d, J=9.2, 2H), δ 8.153 (t, J=1.6 Hz, 1H), δ 8.357 (t, J=1.6 Hz, 1H), δ 8.416 (t, J=1.6 Hz, 1H). $^{19}$F NMR (CD$_3$CN) 376 MHz δ −72.56 (d, J=748 Hz, PF$_6$). $^{13}$C NMR (CD$_3$CN) 150 MHz δ 19.37, δ 56.93, δ 84.61, δ 89.84, δ 102.36, δ 114.03, δ 116.72, δ 116.73, δ 119.58 δ 127.31, δ 128.08, δ 135.79, δ 138.63, δ 139.36, δ 139.93, δ 142.10, δ 164.91, δ 168.04. HRMS (positive mode) obsd mass (M+H)$^+$ 456.9867; calcd mass (C$_{20}$H$_{14}$N$_2$OSI+H)$^+$, 456.9872.

Example 20

(2-methoxy-5-(2-(4-methoxyphenyl)propan-2-yl)phenyl)(4-methoxyphenyl)iodonium hexafluorophosphate

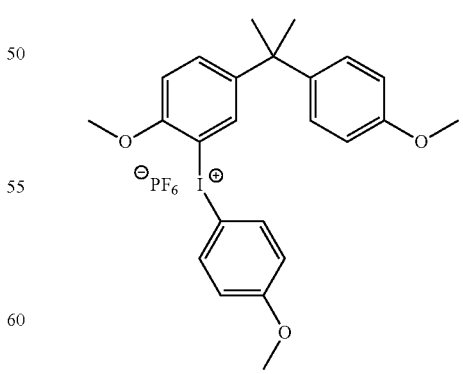

The initial ion exchange yielded a light brown oil. The oil was dissolved in 3 mL of a 1:1 solution of ethyl acetate:dichloromethane and added to a 20 mL vial. Pentane was carefully layered over the ethyl acetate:dichloromethane mixture until the vial was full. The vial was sealed and protected from the light. After 3 days, the crystallized product was collected by vacuum filtration to give (2-methoxy-5-(2-(4-methoxyphenyl)propan-2-yl)phenyl)(4-methoxyphenyl)iodonium hexafluorophosphate as colorless crystalline needles; yield 0.30 g (52%). $^1$H NMR (CD$_3$CN) 400 MHz δ 1.619 (s, 6H), δ 3.762 (s, 3H), δ 3.854 (s, 3H), δ 3.920 (s, 3H), δ 6.798 (d, J=8.2 Hz, 2H), δ 6.982 (d, J=8.4 Hz, 2H), δ 7.095 (d, J=8.4 Hz, 2H), δ 7.112 (d, J=8.4 Hz, 1H), δ 7.471 (dd, J$_1$=8.2 Hz, J$_2$=2.8 Hz, 1H), δ 7.620 (d, J=2.8 Hz, 1H), δ 7.897 (d, J=8.4 Hz, 2H).

Example 21

(N,N-di-(t-butoxycarbonyl)-2-((4,5-dimethoxyphenethylamine dicarbonate)(4-methoxyphenyl)iodonium hexafluorophosphate

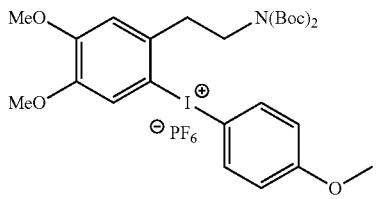

The pasty solid was dissolved in 3 mL dichloromethane and 7 mL of hexanes was layered on top, and this mixture was sealed in a vial protected from light. After the solid had crystallized, it was collected by vacuum filtration to afford (N,N-di-(t-butoxycarbonyl)-2-(4,5-dimethoxyphethylamine dicarbonate)(4-methoxyphenyl)iodonium hexafluorophosphate as a white amorphous solid; yield 0.49 g (65.2%) $^1$H NMR (CD$_3$CN) 400 MHz δ 1.44 (s, 18H), δ 3.10 (t, J=7.16 Hz, 2H), δ 3.80 (t, J=7.16 Hz, 2H), δ 3.82 (s, 3H), δ 3.83 (s, 3H), δ 3.84 (s, 3H), δ 6.95 (s, 1H), δ 7.04 (d, J=9.01 Hz, 2H), δ 7.56 (s, 1H), δ 8.01 (d, J=9.01 Hz, 2H). $^{13}$C NMR (CD$_3$CN) 100 MHz δ 28.3, 38.3, 47.4, 56.8, 56.9, 57.3, 83.8, 107.0, 115.2, 119.1, 120.3, 136.6, 138.2, 151.0, 153.8, 154.2, 164.3. $^{19}$F NMR (CD$_3$CN) 400 MHz δ −72.9 (d, J=707.0 Hz, 6F). HRMS: (HREI) calcd. for C$_{27}$H$_{37}$O$_7$NIPF$_6$ [M-PF$_6$+Na]$^+$ 614.9165. found.

Example 22

(N,N-di-(t-butoxycarbonyl)-2-(4,5-dimethoxyphenethylamine dicarbonate)(4-(3,3-dimethylbutoxyphenyl))iodonium hexafluorophosphate

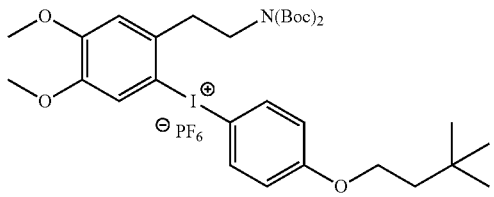

The pasty solid was recrystallized by dissolving the solid in 3 mL dichloromethane and layering 7 mL of hexanes and sealing the contents in a vial, protected from light. After the solid had crystallized, it was collected by vacuum filtration to afford (N,N-di-(t-butoxycarbonyl)-2-(4,5-dimethoxyphenethylamine dicarbonate)(4-(3,3-dimethylbutoxyphenyl))iodonium hexafluorophosphate as a white amorphous solid; yield 0.49 g (65.2%) $^1$H NMR (CD$_3$CN) 400 MHz δ 0.968 (s, 9H), δ 1.440 (s, 18H), δ 1.692 (t, J=7.2 Hz, 2H), δ 3.100 (t, J=7.2 Hz, 2H), δ 3.795 (t, J=7.2 Hz, 2H), δ 3.815 (s, 3H), δ 3.843 (s, 3H), δ 4.093 (t, J=7.2 Hz, 2H), δ 6.954 (s, 1H), δ 7.024 (d, J=8.4 Hz, 2H), δ 7.544 (s, 1H). δ 7.990 (d, J=8.4 Hz, 2H). $^{13}$C NMR (CD$_3$CN) 100 MHz δ 28.60, 30.23, 30.71, 38.63, 43.05, 47.72, 57.13, 57.63, 67.61, 84.10, 103.07, 107.39, 115.45, 119.83, 120.68, 136.84, 138.45, 151.16, 154.01, 154.39, 163.90. $^{19}$F NMR (CD$_3$CN) 376 MHz δ −79.36.

Example 23

(3-Cyano-5-(pyridine-2-ylethynyl)phenyl)(4-methoxyphenyl)iodonium hexafluorophosphate

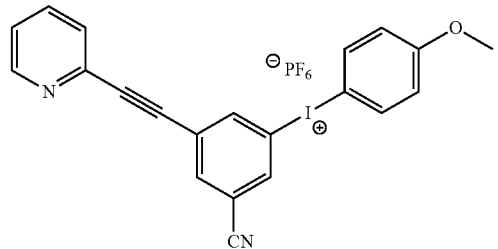 [SMILES: COc1ccc([I+]c2cc(C#N)cc(C#Cc3ccccn3)c2)cc1 ; "PF6"]

The crude filtered product was dissolved in CH$_2$Cl$_2$ to remove it from the filter and the solvent was evaporated. The colorless solid was recrystallized from CH$_2$Cl$_2$/heptanes to give a colorless, crystalline solid. (14.6 mg, 50%). $^1$H NMR (300 MHz, CD$_3$CN) δ=8.63 (d, 1 H, J=4.8 Hz), 8.49 (d, 1 H, J=1.2 Hz), 8.40 (s, 1 H), 8.21 (d, 1 H, J=0.8 Hz), 8.01 (d, 2 H, J=9.2 Hz), 7.90 (t, 1 H, J=7.6 Hz), 7.68 (d, 1 H, J=7.6 Hz), 7.48 (t, 1 H, J=6.2 Hz), 7.10 (d, 2 H, J=9.2 Hz), 3.86 (s, 3 H); $^{13}$C NMR (75 MHz, CD$_3$CN) δ=150.51, 141.36, 139.12, 138.22, 137.92, 136.81, 127.89, 124.35, 118.44, 117.30, 115.64, 55.84; $^{19}$F NMR (282 MHz, CD$_3$CN): −72.96 (d, 6F, J=705 Hz); HR-FAB MS: (M-PF$_6$)+ 437.0149 m/z (calcd for C$_{21}$H$_{14}$IN$_2$O, 437.0145).

Example 24

(3-cyano-5-((6-methylpyridin-2-yl)ethynyl)phenyl)(4-methoxyphenyl)iodonium hexafluorophosphate

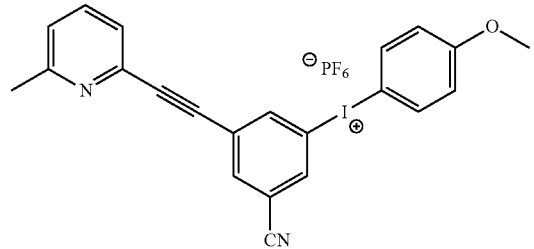

The crude product was recrystallized from CH$_2$Cl$_2$/heptanes to give a colorless, crystalline solid (12.5 mg, 50%). $^1$H NMR (400 MHz, CD$_3$CN): δ=8.47 (s, 1 H), 8.39 (s, 1 H), 8.20

(s, 1 H), 8.07 (d, 2 H, J=8.1 Hz), 7.72 (t, 1 H, J=8.0 Hz), 7.44 (d, 1 H, J=8.0 Hz), 7.29 (d, 1 H, J=8.0 Hz), 7.10 (d, 2 H, J=9.2 Hz), 3.86 (s, 3 H), 2.52 (s, 3 H). $^{13}C$ NMR (100 MHz, $CD_3CN$): δ=163.82, 159.59, 141.36, 140.57, 139.16, 138.29, 137.89, 137.10, 126.78, 125.09, 124.06, 118.49, 115.66, 112.93, 101.28, 93.33, 82.99, 55.85, 23.46; $^{19}F$ (376 MHz, $CD_3CN$) δ=−72.79 (d, 6F, 703.1 Hz); HR-FAB MS: $(M-PF_6)^+$ 451.0299 m/z (calcd for $C_{22}H_{16}IN_2O$, 451.03).

Example 25

4-(Diacetoxyiodo)-1-[(2S)-2-[(di-tert-butoxycarbonyl)amino]-3-methoxy-3-oxopropyl]benzene

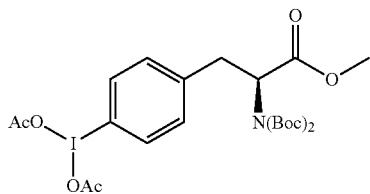

In a $N_2$ charged glove box, (5)-methyl 2-bis-(tert-butoxycarbonyl)amino)-3-(4iodophenyl)propanoate (6.4 g, 12.6 mmol) was dissolved in 63 mL of dry, distilled acetonitrile in a plastic container. To the same container was then added trimethylsilyl acetate (4.2 g, 31.4 mmol) and the reaction mixture was stirred. In a separate plastic flask, SelectFluor® was dissolved in 103 mL of dry, distilled acetonitrile and the Selectfluor® mixture was added dropwise to the phenylalanine/trimethylsilyl acetate mixture while stirring, and the solution was allowed to stir for 8 hours. After 8 hours, the acetonitrile was removed in vacuo to yield a white solid. The solid was washed with dichloromethane (3×50 mL) and the organic fractions were combined. The organic layer was washed with aqueous acetate buffer (4×40 mL) (NaOAc: HOAc; 0.5M:0.5M; pH 5), and the organic layer was dried over sodium sulfate. The dichloromethane was removed in vacuo to give a yellow oil, which was treated with 40 mL of pentanes and subjected to an ultrasonic water bath until the salt solidified. The pentane was decanted and the white solid was placed under high dynamic vacuum for 5 hours. The white solid was then carried forward to the next step without other purification. $^1H$ NMR ($CD_3CN$) 400 MHz δ 1.40 (s, 18H), δ 1.93 (s, 6H), δ 3.29 (dd, $J_1$=11.3 Hz, $J_2$=14.0 Hz, 1H), δ 3.48 (dd, $J_1$=11.3 Hz, $J_2$=14.0 Hz, 1H), δ 3.75 (s, 3H), δ 5.25 (dd, $J_1$=11.3 Hz, $J_2$=14.0 Hz, 1H), δ 7.38 (d, J=8.4 Hz, 2H), δ 8.07 (d, J=8.4 Hz, 2H).

Example 26

4-([(2S)-2-[(di-tert-butoxycarbonyl)amino]-3-methoxy-3-oxopropyl]phenyl)-[4'-(3,3-dimethylbutoxy)phenyl]iodonium triflate

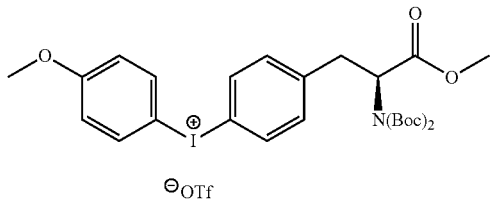

In a $N_2$ charged glove box, ((S)-methyl 2-bis-(tert-butoxycarbonyl)amino)-3-(4iodophenyl)propanoate)(bis-acetyloxy)-$\lambda^3$-iodane (1.0 g, 1.6 mmol) was dissolved in 5.6 mL of dry, distilled acetonitrile. In a separate flask, potassium (4-methoxyphenyl)trifluoroborate (0.34 g, 1.6 mmol) was dissolved in 13 mL of dry, distilled acetonitrile and was subsequently added to the hypervalent iodine solution. Next, trimethylsilyl trifluoroacetate (0.29 g, 1.6 mmol) was added dropwise to the reaction vial while stirring. After 10 minutes at room temperature the solvent was removed in vacuo to yield an oil. The oil was dissolved in 20 mL of dichloromethane and the organic layer was washed with aqueous acetate buffer (3×12 mL) (NaOAc: HOAc; 0.5M:0.5M; pH 5). The dichloromethane layer was removed in vacuo to yield a light yellow solid. The solid was redissolved in 4 mL of dry acetonitrile and an aqueous solution of sodium hexafluorophosphate (1.0 g in 4 mL deionized water) was added to the reaction flask and the solution was stirred for 3 minutes. The formed residue was extracted with dichloromethane (3×20 mL), the organic layers combined and over sodium sulfate, and removal of the solvent in vacuo gave a white solid. The white solid was redissolved in 3 mL of an acetonitrile/water (90:10) solution and passed through an IRA-400 resin previously loaded with trifluoromethanesulfonate anion with an additional 25 mL of acetonitrile/water (90:10). The solvent was removed in vacuo to give a colorless oil. $^1H$ NMR ($CD_3CN$) 400 MHz δ 1.21 (s, 18H), δ 3.21 (dd, $J_1$=11.3 Hz, $J_2$=14.0 Hz, 1H), δ 3.42 (dd, $J_1$=11.3 Hz, $J_2$=14.0 Hz, 1H), δ 3.69 (s, 3H), δ 3.83 (s, 3H), δ 5.16 (dd, $J_1$=4.9 Hz, $J_2$=10.9 Hz, 1H), δ 7.05 (d, J=8.4 Hz, 2H), δ 7.33 (d, J=8.4 Hz, 2H), δ 7.96 (d, J=8.4 Hz, 2H), δ 8.02 (d, J=8.4 Hz, 2H).

What is claimed is:

1. A process for making a compound of Formula I:

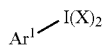

I comprising:
treating a compound of Formula II:

II with (A) a tetravalent silicon moiety having at least one X group bound to Si, wherein each X is, independently, a ligand that is a conjugate base of an acid HX, wherein HX has a pKa of less than or equal to 12; and is selected from the group consisting of halide, aryl carboxylate, alkyl carboxylate, phosphate, phosphonate, phosphonite, azide, thiocyanate, cyanate, phenoxide, triflate, thiolates, and stabilized enolates; and (B) (1-chloromethyl-4-fluoro-1,4-diazoniabicyclo[2.2.2]octane) bis(tetrafluoroborate), (1-fluoro-4-methyl-1,4-diazoniabicyclo[2.2.2]octane) bis(tetrafluoroborate), or an optionally substituted N-fluoropyridinium tetrafluoroborate;

wherein:

$Ar^1$ is selected from the group consisting of:

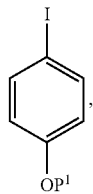

1

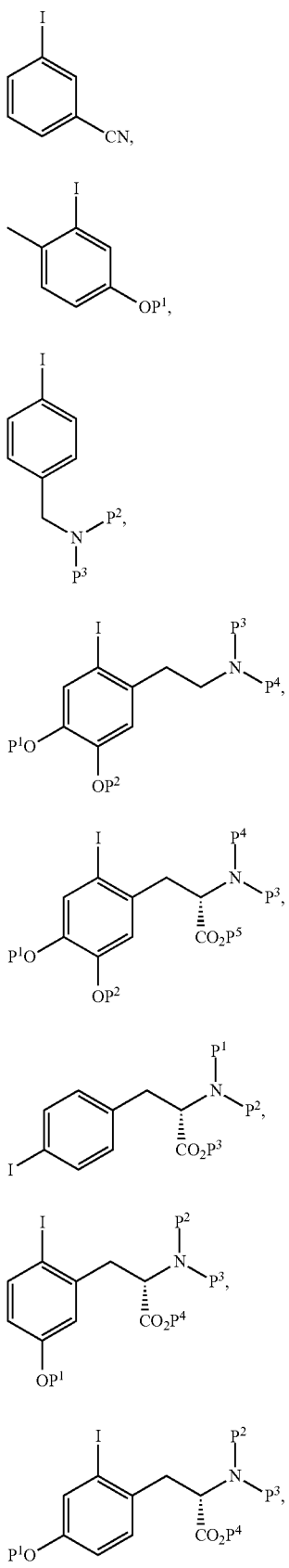
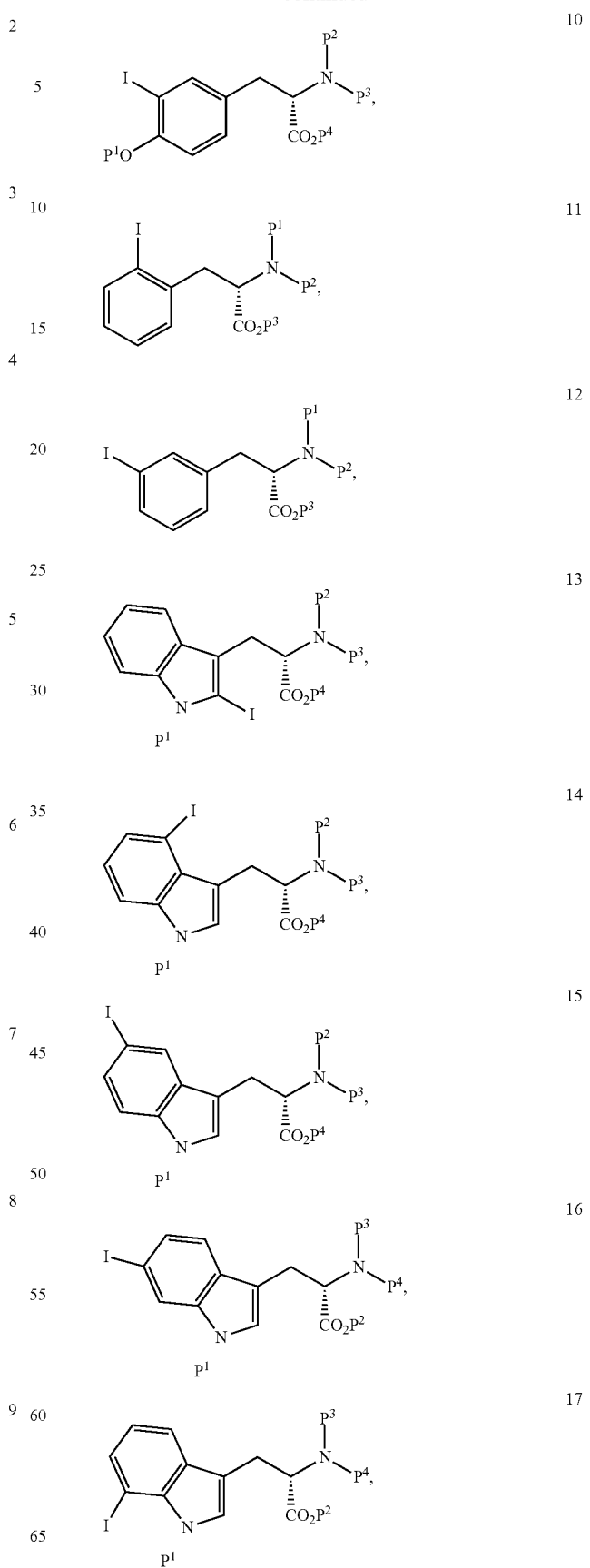

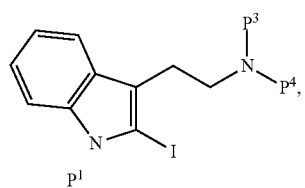
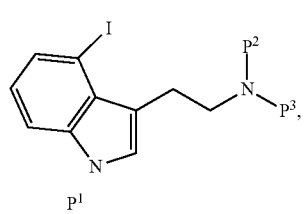
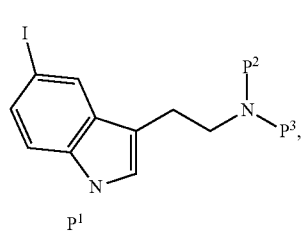
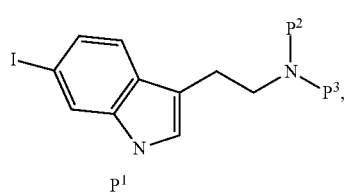
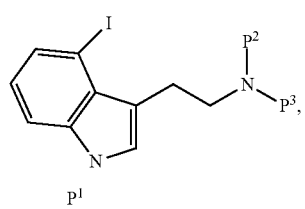
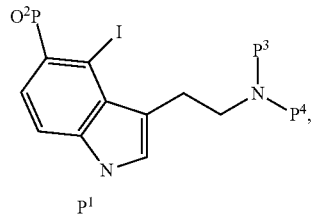
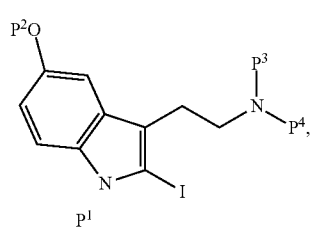
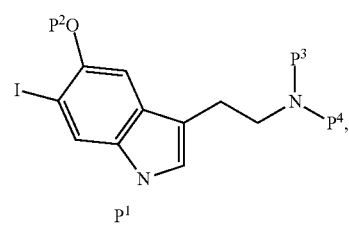
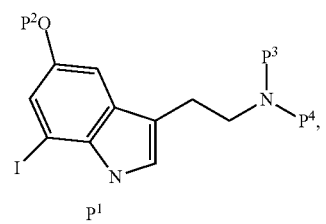
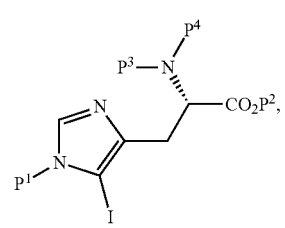
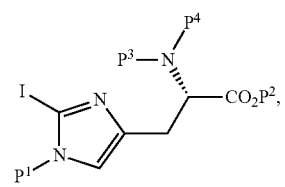
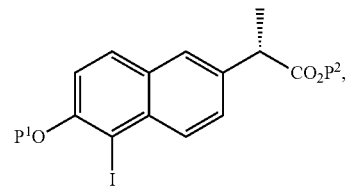
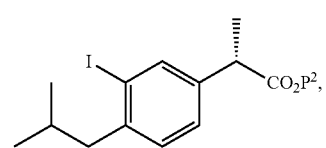
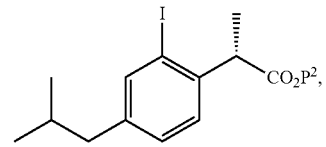
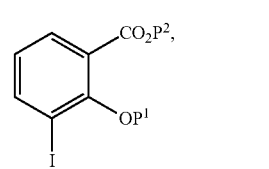

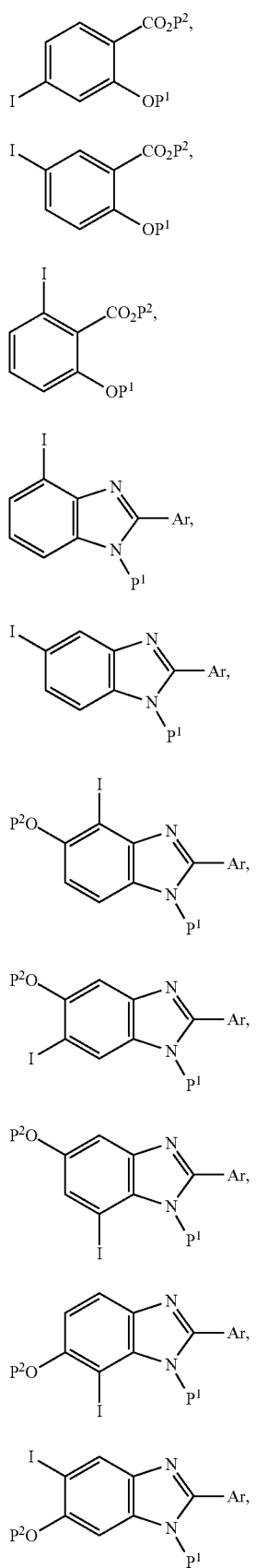
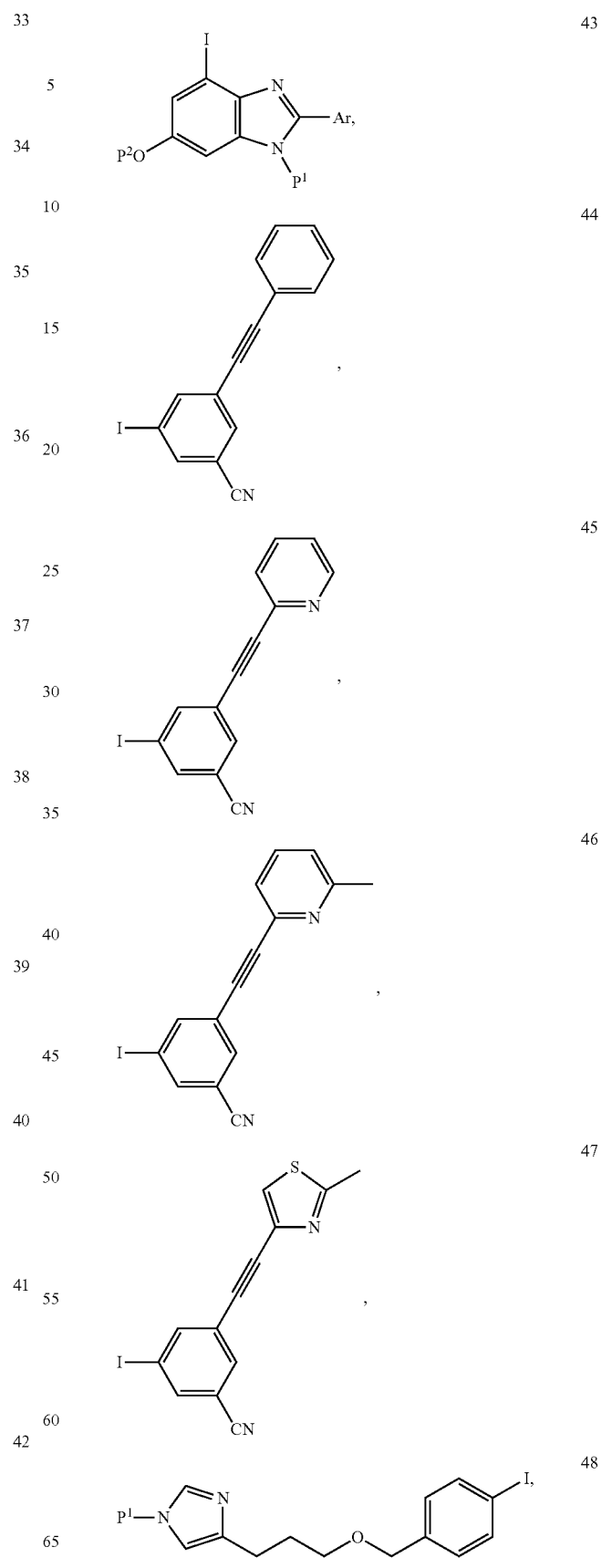

49
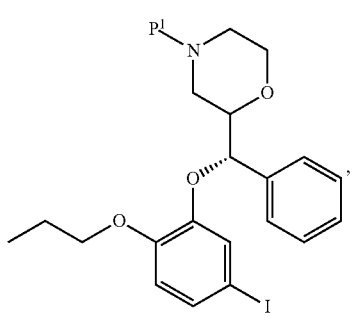
50
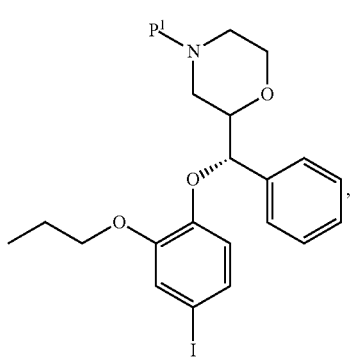
51
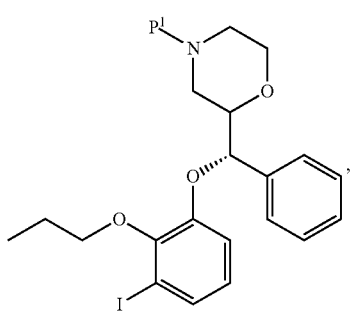
52
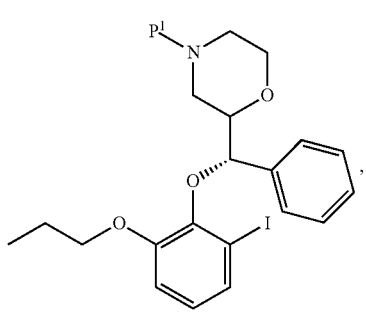
53
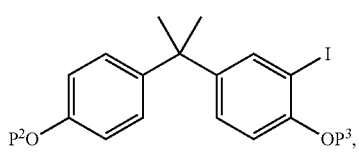
54
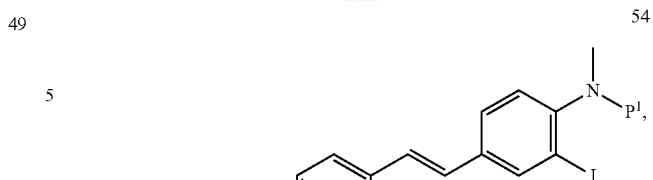
55
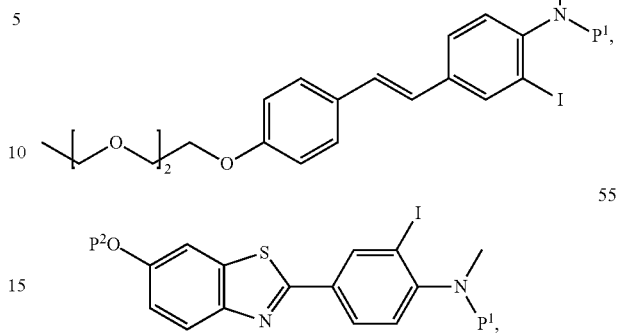
56
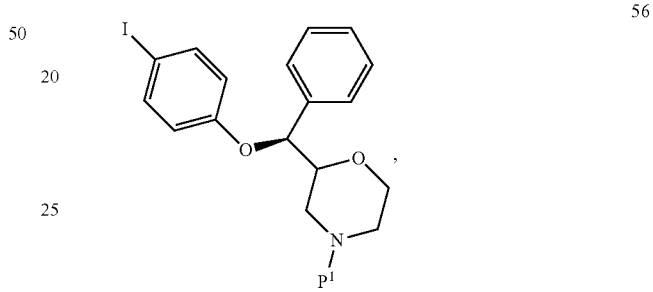
57
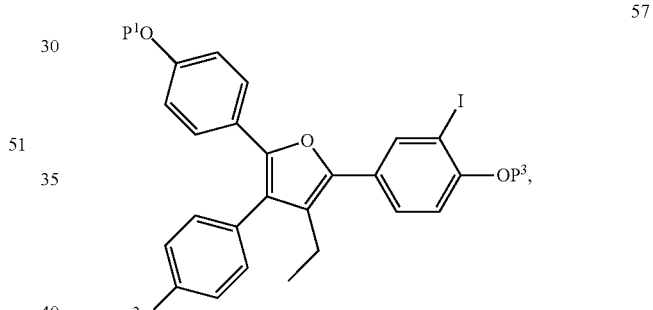
58
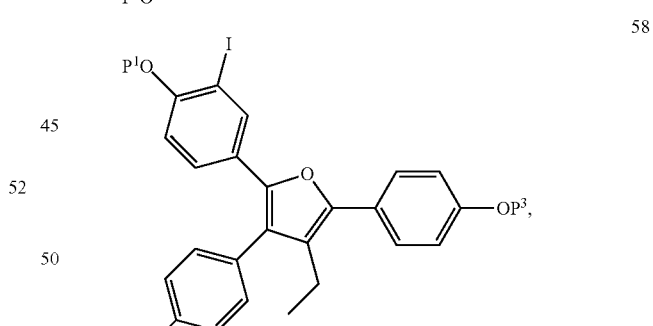
59
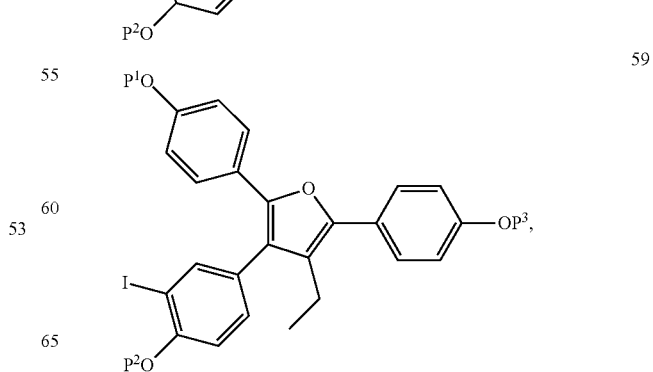

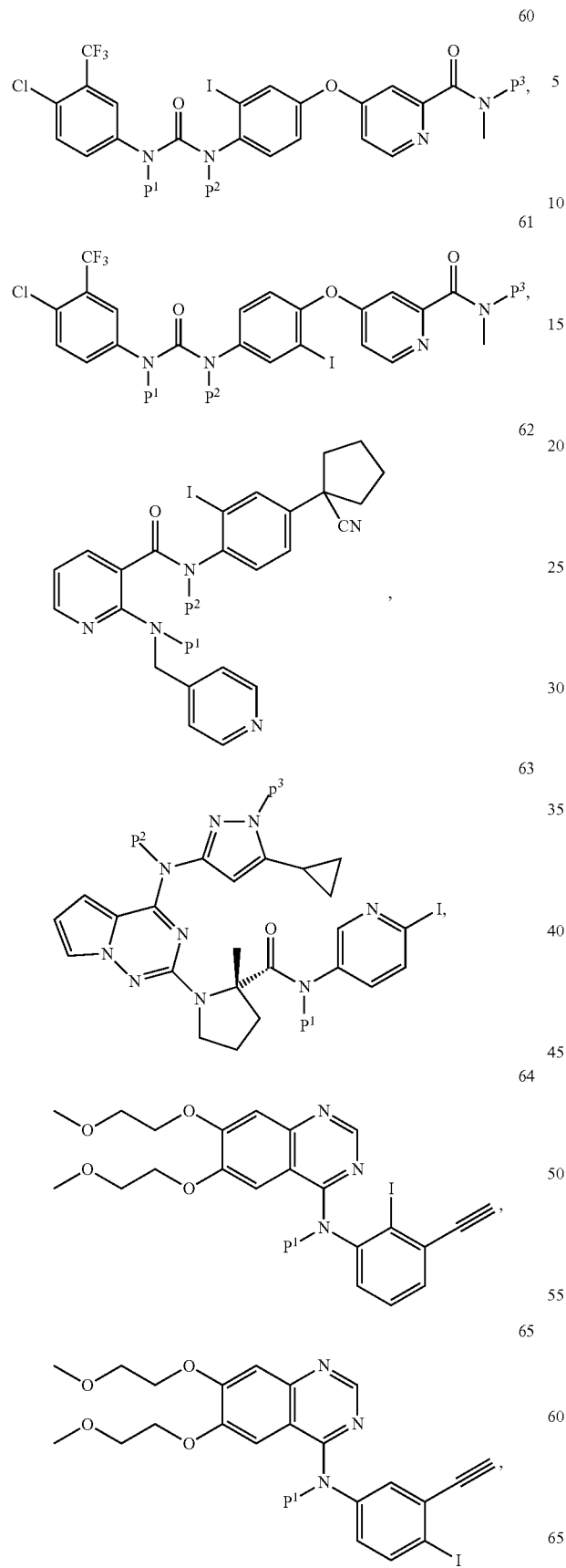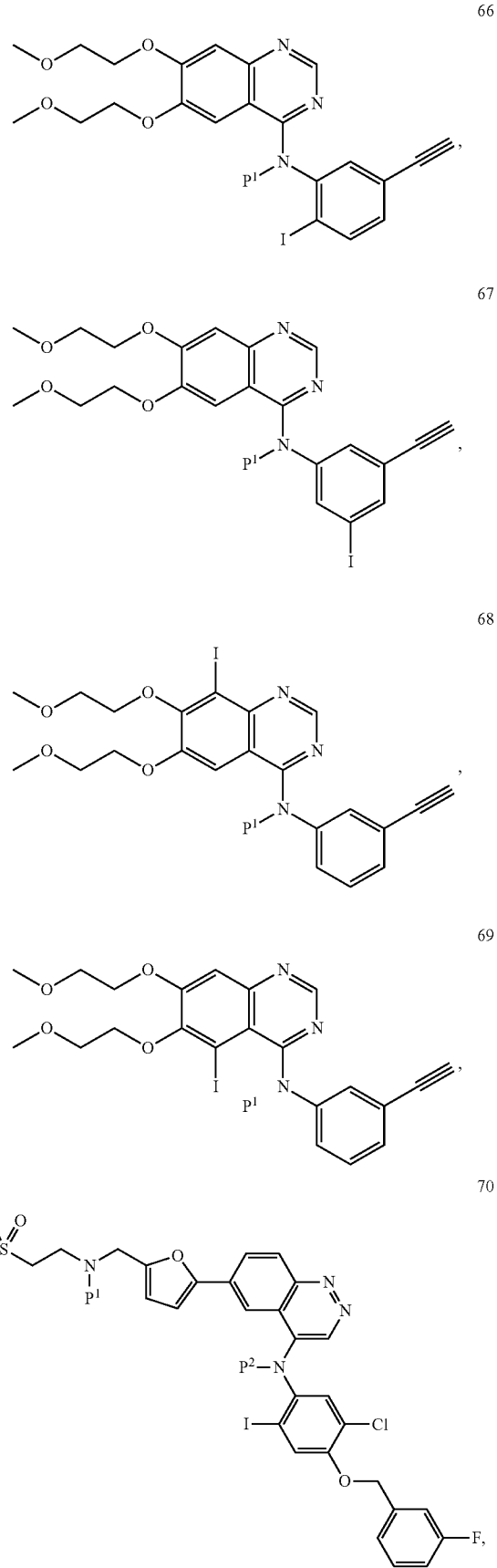

107
-continued
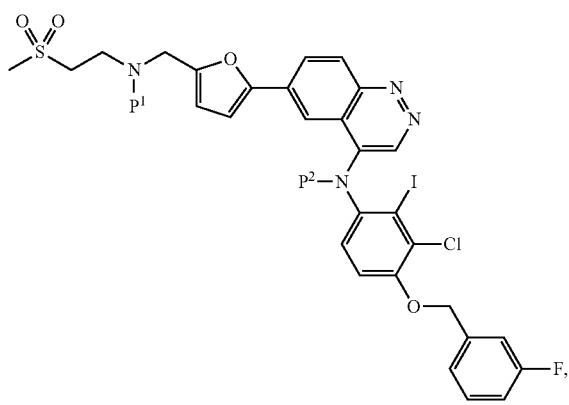
71
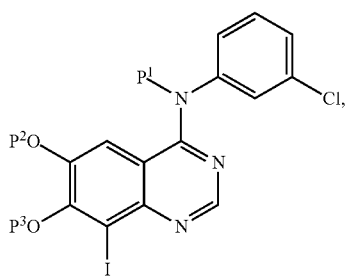
76
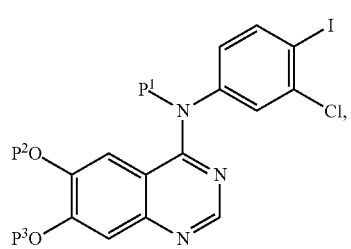
72
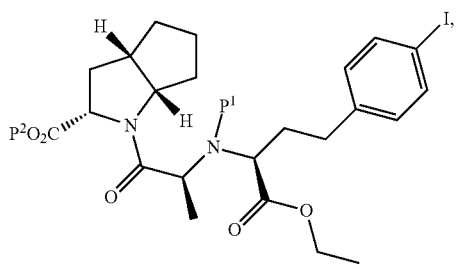
77
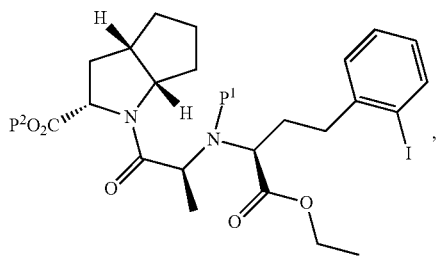
78
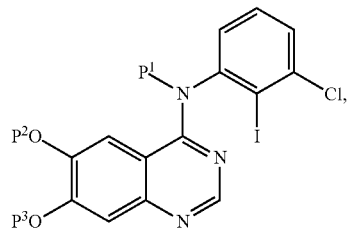
73
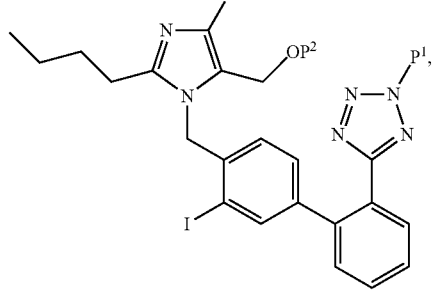
79
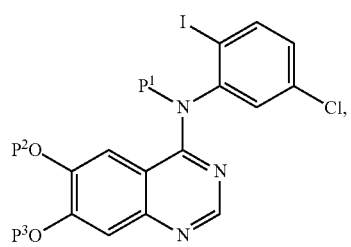
74
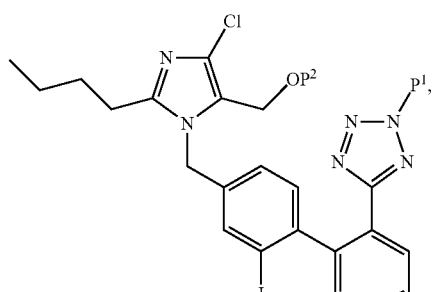
80
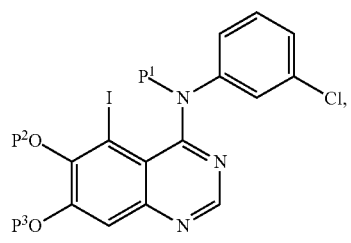
75
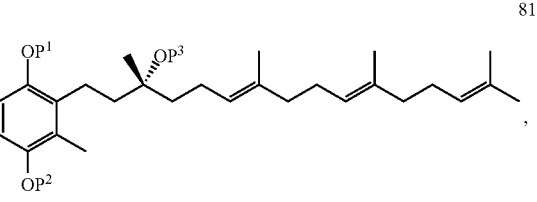
81

-continued
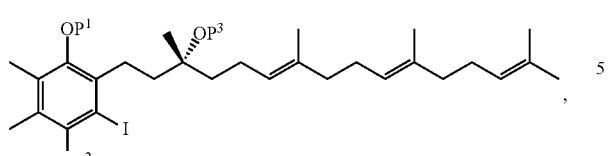
82
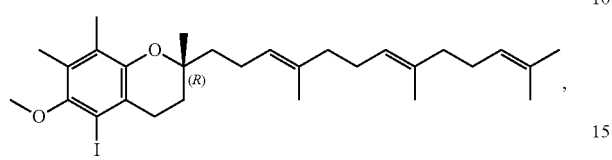
83
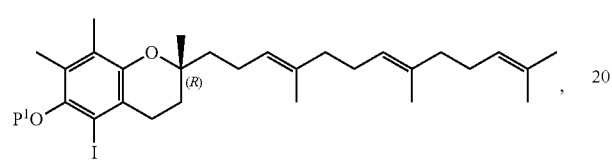
84
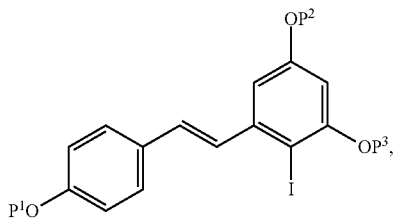
85
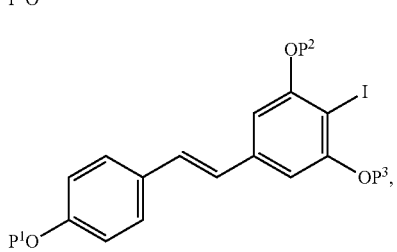
86
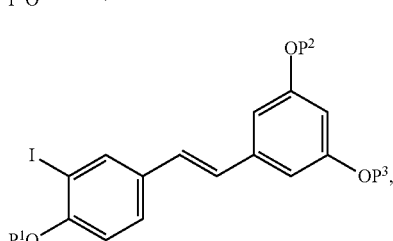
87
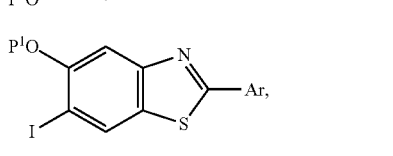
88
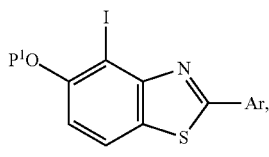
89
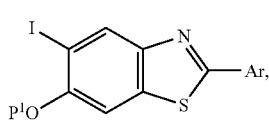
90
-continued
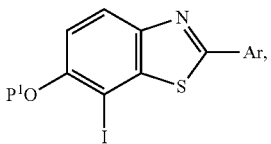
91
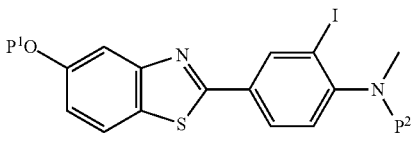
92
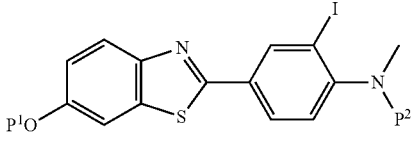
93
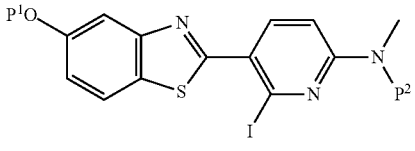
94
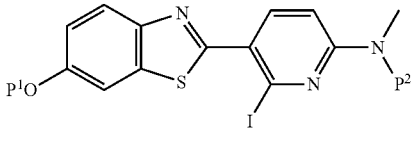
95
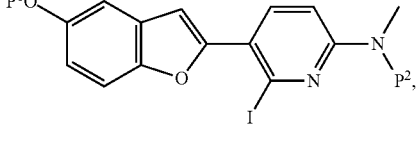
96
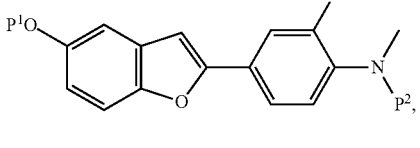
97
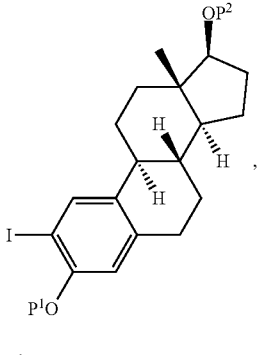
98
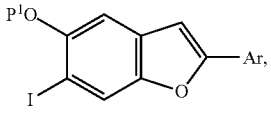
100

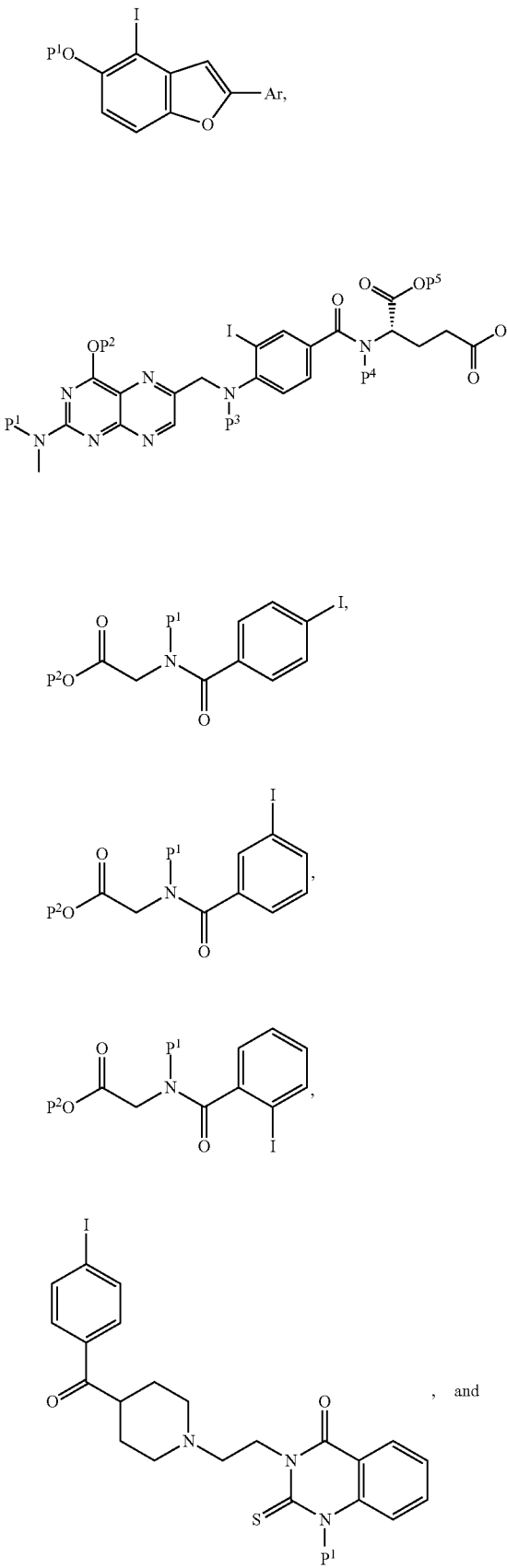

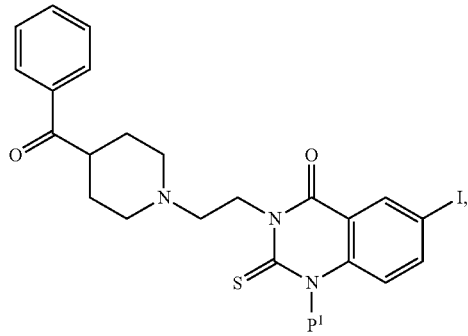

, and wherein Ar is an optionally substituted aryl or heteroaryl, wherein Ar does not have unprotected protic groups; and $P^1$, $P^2$, $P^3$, $P^4$, $P^5$, and $P^6$ are each, independently, protecting groups.

2. The process of claim 1, wherein the process is carried out in the absence of added acid.

3. The process of claim 1, wherein the process utilizes (1-chloromethyl-4-fluoro -1,4-diazoniabicyclo[2.2.2]octane) bis(tetrafluoroborate).

4. The process of claim 1, wherein the process utilizes (1-fluoro-4-methyl-1,4-diazoniabicyclo [2.2.2]octane) bis (tetrafluoroborate).

5. The process of claim 1, wherein the process utilizes N-fluoro-2,3,4,5,6-pentachloropyridinium tetrafluoroborate.

6. The process of claim 1, wherein the process utilizes less than 2 equivalents of (1-chloromethyl-4-fluoro-1,4-diazoniabicyclo[2.2.2]octane) bis(tetrafluoroborate), (1-fluoro-4-methyl-1,4-diazoniabicyclo[2.2.2]octane) bis(tetrafluoroborate), or optionally substituted N -fluoropyridinium tetrafluoroborate for 1 equivalent of the compound of Formula II.

7. The process of claim 1, wherein the process utilizes less than 1.5 equivalents of (1-chloromethyl-4-fluoro-1,4-diazoniabicyclo[2.2.2]octane) bis(tetrafluoroborate), (1-fluoro-4-methyl-1,4-diazoniabicyclo[2.2.2]octane) bis(tetrafluoroborate), or optionally substituted N -fluoropyridinium tetrafluoroborate for 1 equivalent of the compound of Formula II.

8. The process of claim 1, wherein each X is, independently, a ligand that is a conjugate base of an acid HX, wherein HX has a pKa of less than or equal to 5.

9. The process of claim 1, wherein each X is $O(C=O)CH_3$.

10. The process of claim 1, wherein the tetravalent silicon moiety is $(R^1)_3Si—X$, wherein each $R^1$ is, independently, $C_{1-12}$ alkyl or aryl.

11. The process of claim 10, wherein each $R^1$ is methyl.

12. The process of claim 10, wherein $(R^1)_3Si—X$ is $(CH_3)_3Si—X$.

13. The process of claim 10, wherein $(R^1)_3Si—X$ is $(CH_3)_3Si—O(C=O)CH_3$.

14. The process of claim 1, wherein the process utilizes 2 equivalents or more of the tetravalent silicon moiety for 1 equivalent of the compound of Formula II.

15. The process of claim 1, wherein the process utilizes 2.5 equivalents to 3 equivalents of the tetravalent silicon moiety for 1 equivalent of the compound of Formula II.

16. The process of claim 15, wherein the tetravalent silicon moiety is $(R^1)_3Si—X$, wherein each $R^1$ is, independently, $C_{1-12}$ alkyl or aryl.

17. The process of claim 1, wherein the processes comprises treating a compound of Formula II with $(CH_3)_3Si—O$ (C=)CH$_3$; and (1-chloromethyl-4-fluoro-1,4-diazoniabicyclo[2.2.2]octane) bis(tetrafluoroborate).

18. The process of claim 1, wherein the processes comprises treating a compound of Formula II with 2.5 equivalents to 3 equivalents of (CH$_3$)$_3$Si—O(C=O)CH$_3$; and less than 1.5 equivalents of (1-chloromethyl-4-fluoro-1,4-diazoniabicyclo[2.2.2]octane) bis(tetrafluoroborate).

19. A process for making a compound of Formula III:

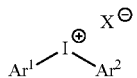
III wherein Ar$^2$ is an optionally substituted aryl or heteroaryl, the process comprising:
treating a compound of Formula II:

Ar$^1$—I      II with (A) a tetravalent silicon moiety having at least one X group bound to Si, wherein each X is, independently, a ligand that is a conjugate base of an acid HX, wherein HX has a pKa of less than or equal to 12; and is selected from the group consisting of halide, aryl carboxylate, alkyl carboxylate, phosphate, phosphonate, phosphonite, azide, thiocyanate, cyanate, phenoxide, triflate, thiolates, and stabilized enolates; and
(B) (1-chloromethyl-4-fluoro-1,4-diazoniabicyclo [2.2.2] octane) bis(tetrafluoroborate), (1-fluoro-4-methyl-1,4-diazoniabicyclo [2.2.2]octane) bis(tetrafluoroborate), or an optionally substituted N-fluoropyridinium tetrafluoroborate;
wherein:
Ar$^1$ is selected from the group consisting of:

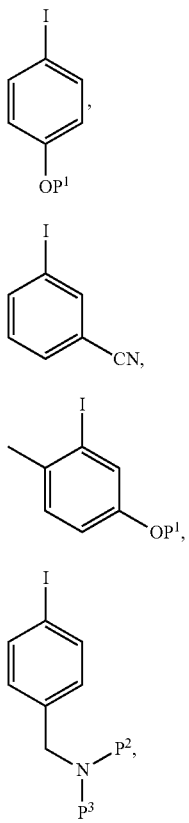

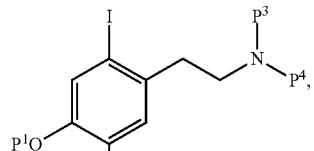

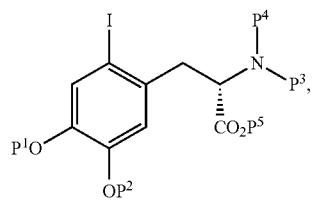

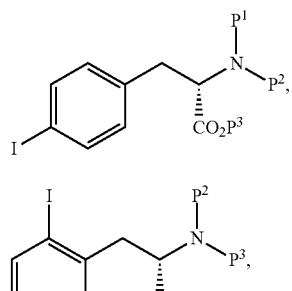

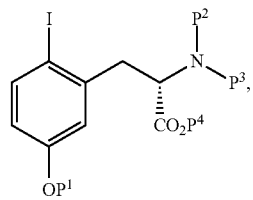

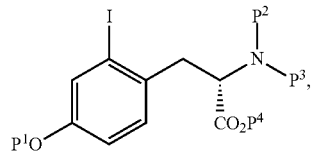

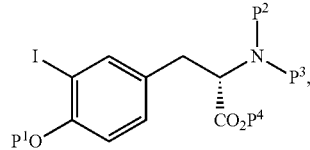

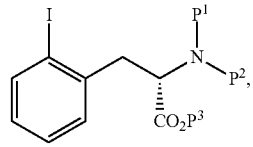

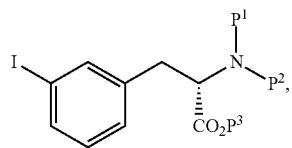

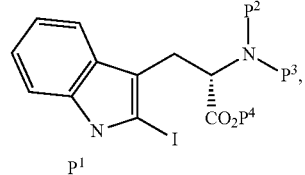

14
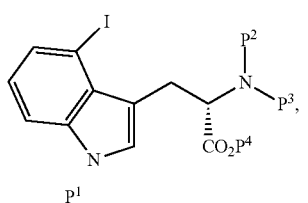
15
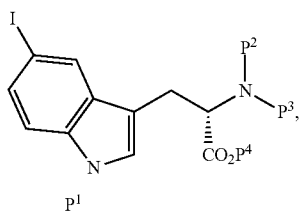
16
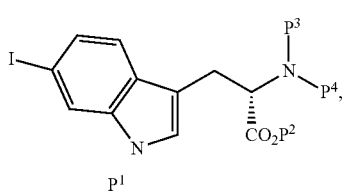
17
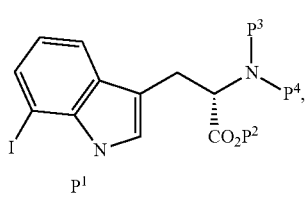
18
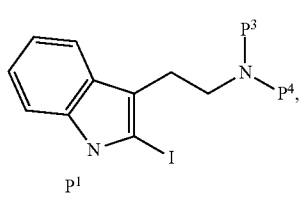
19
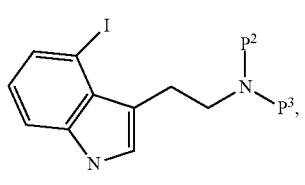
20
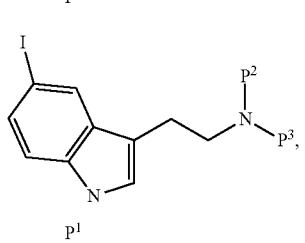
21
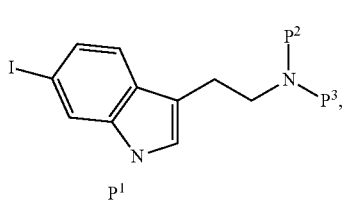
22
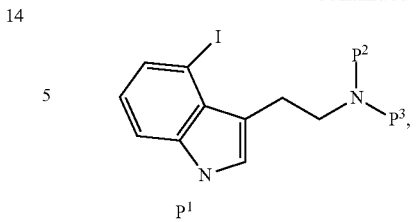
23
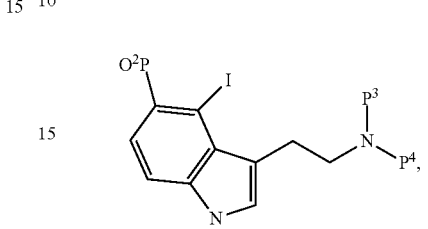
24
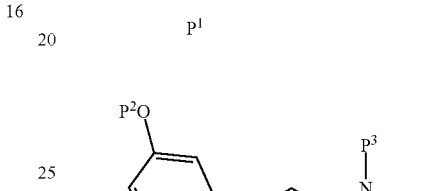
25
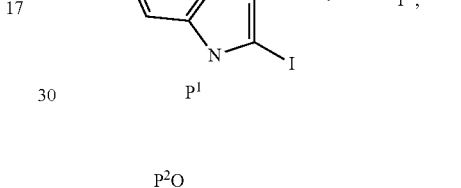
26
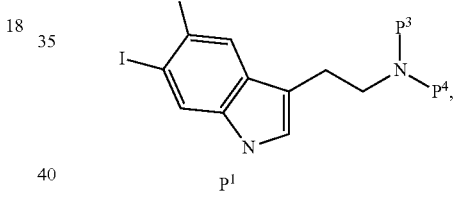
27
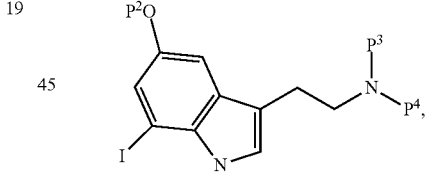
28
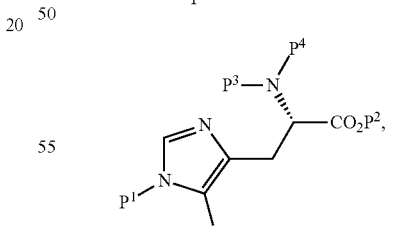
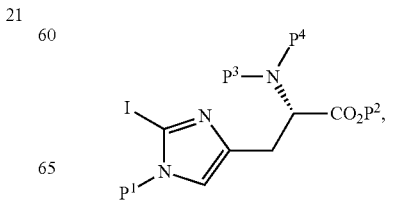

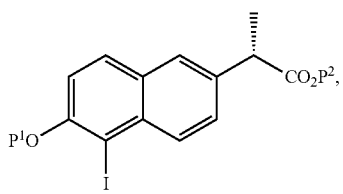
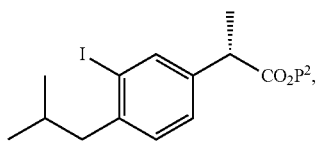
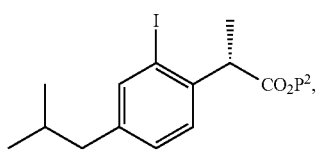
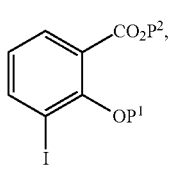
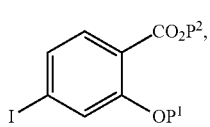
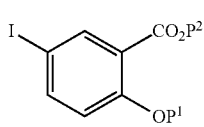
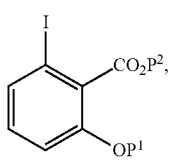
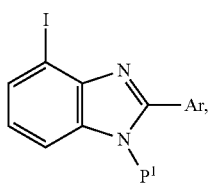
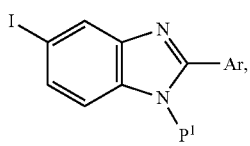
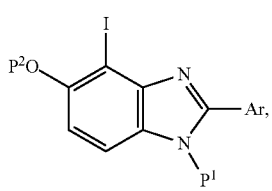
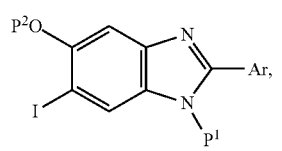
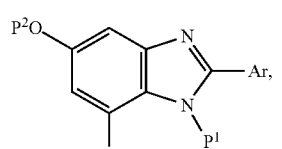
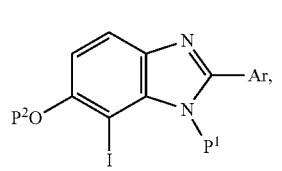
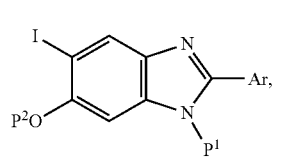
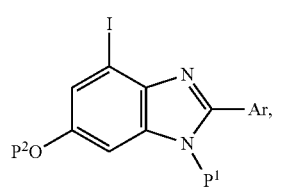
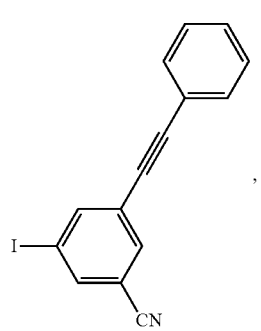
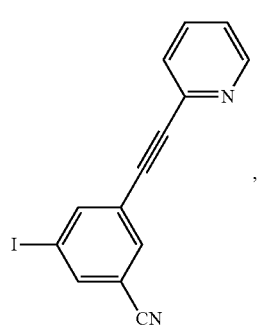

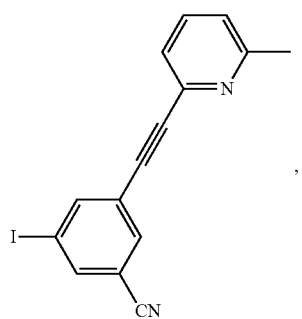
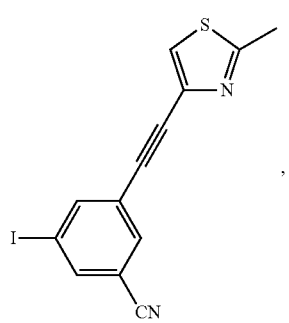
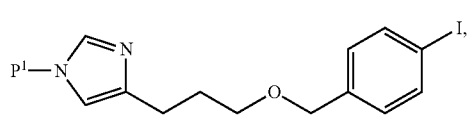
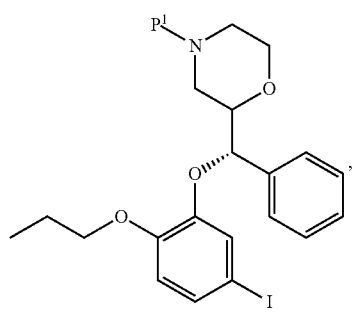
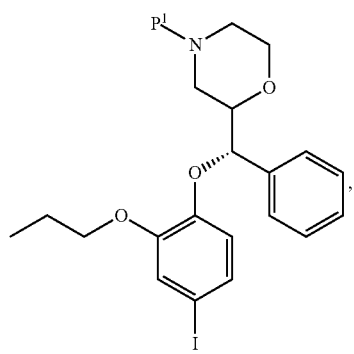
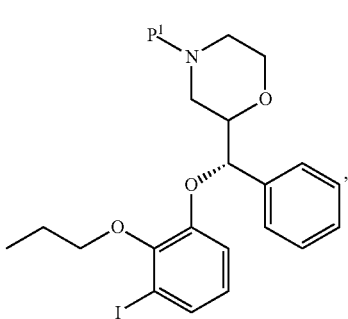
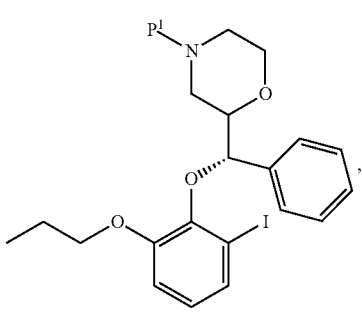
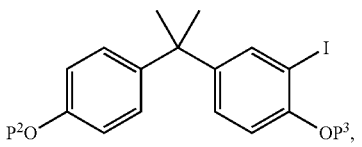
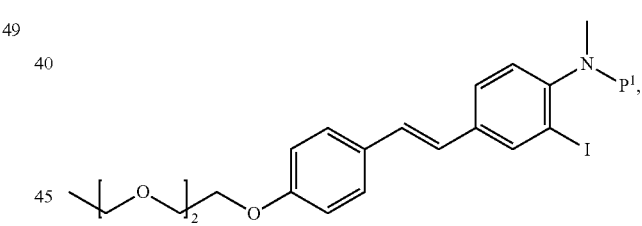
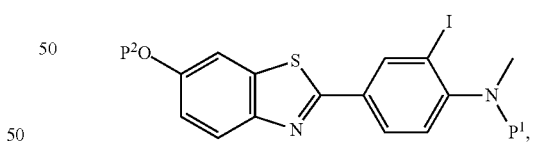
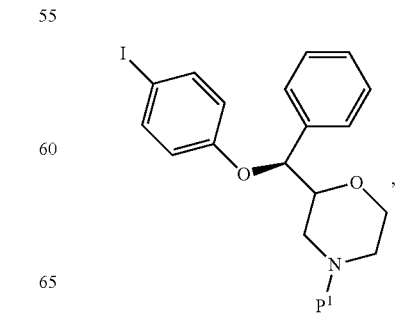

57
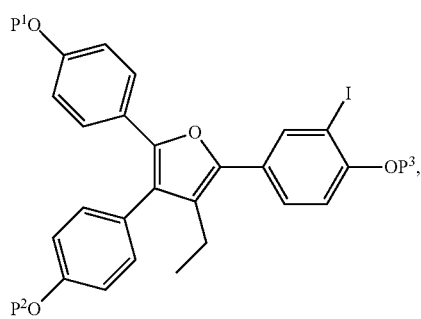
58
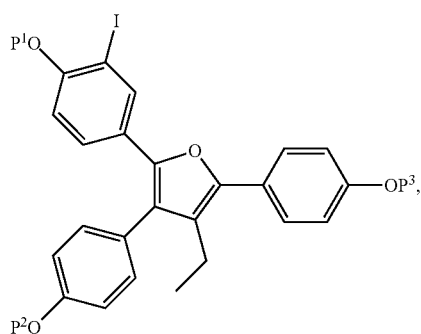
59
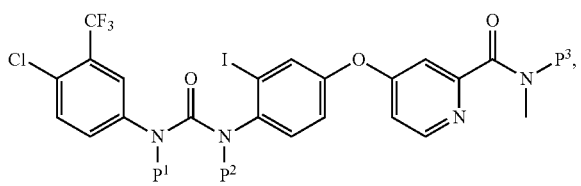
60
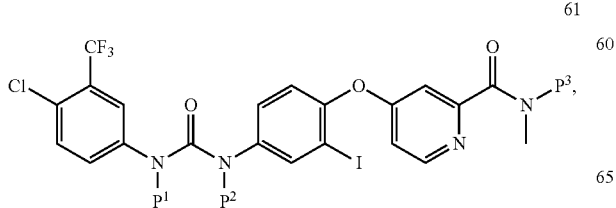
61
62
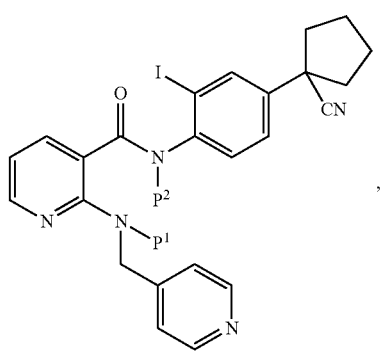
63
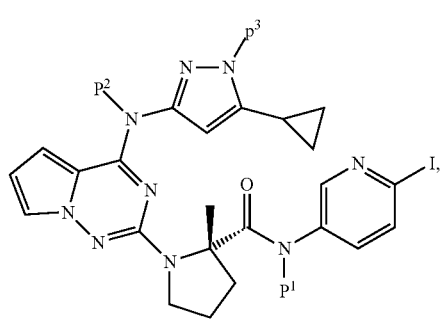
64
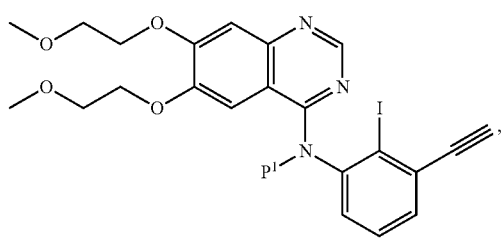
65
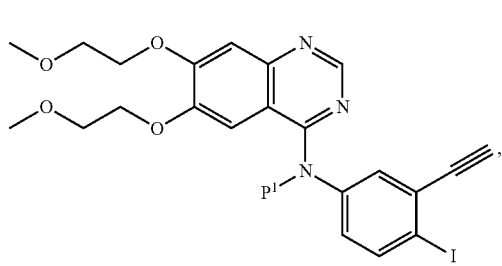
66
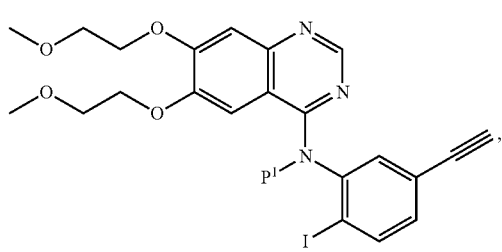

67
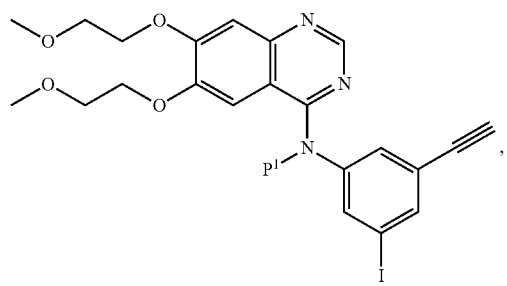
68
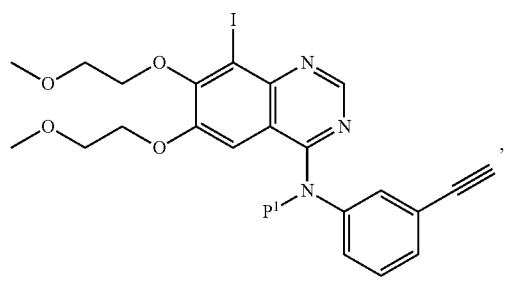
69
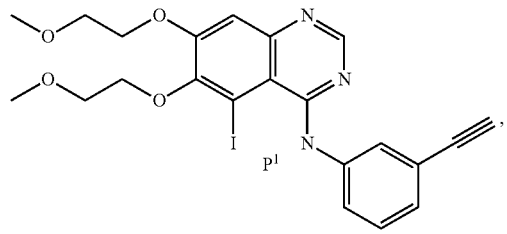
70
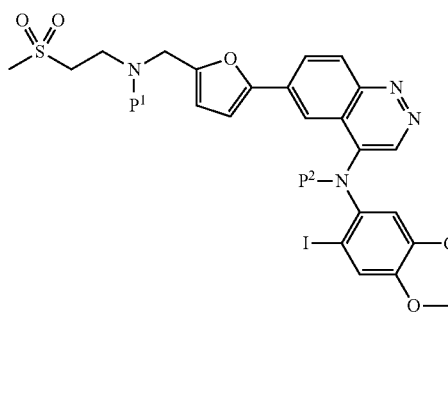
71
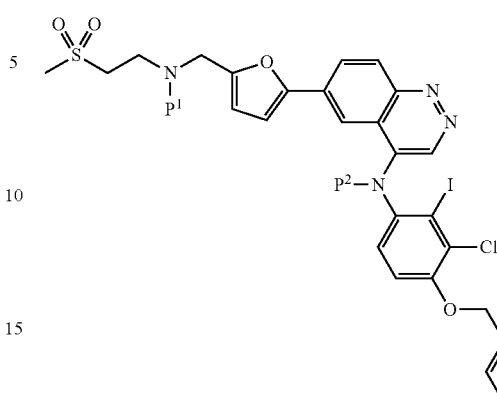
72
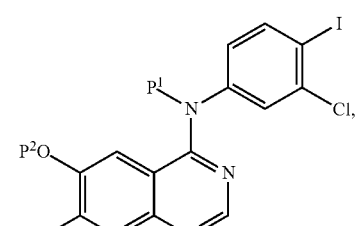
73
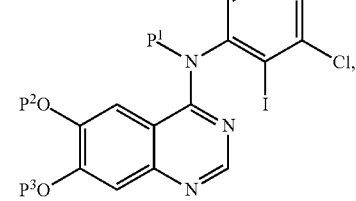
74
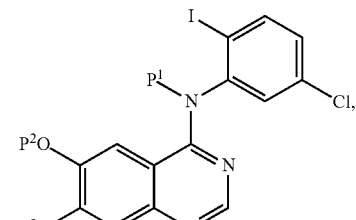
75
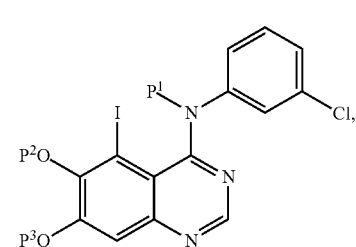

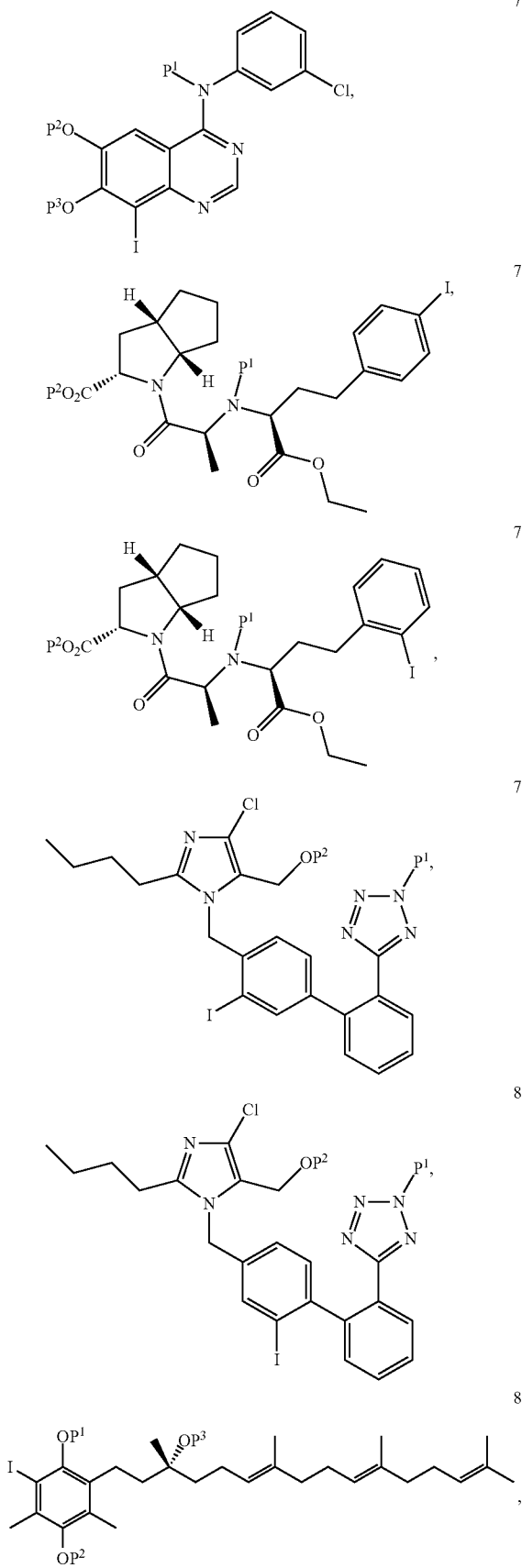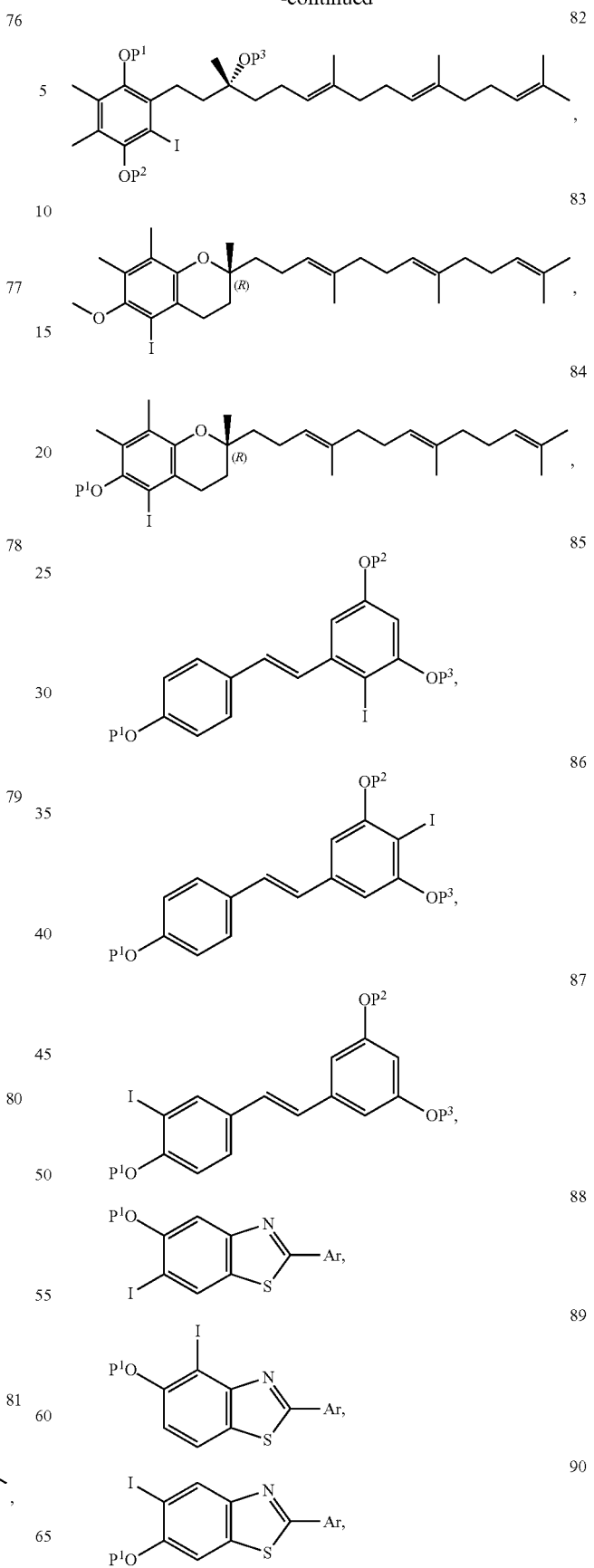

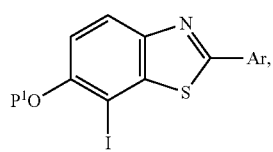
91
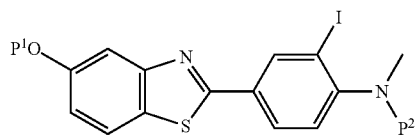
92
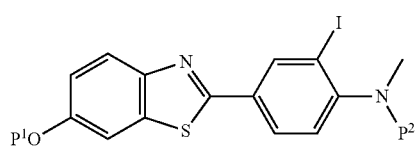
93
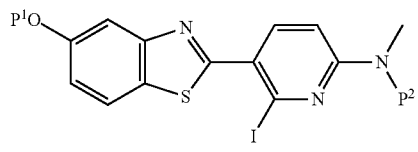
94
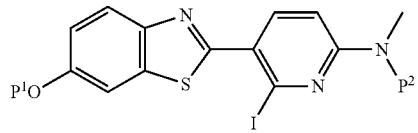
95
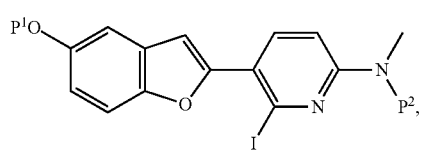
96
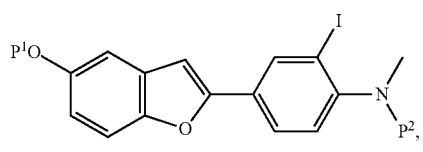
97
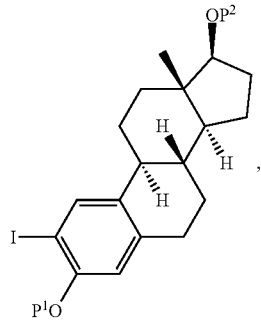
98
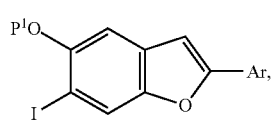
100
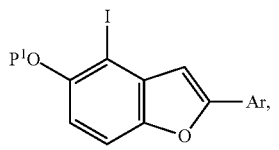
102
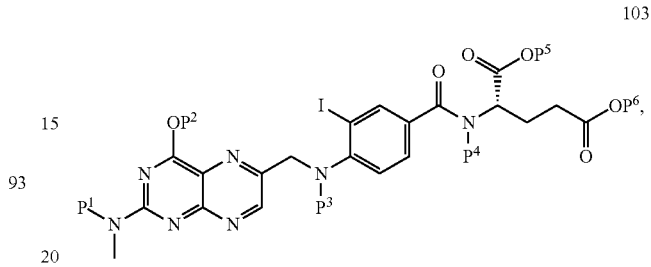
103
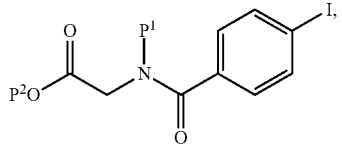
104
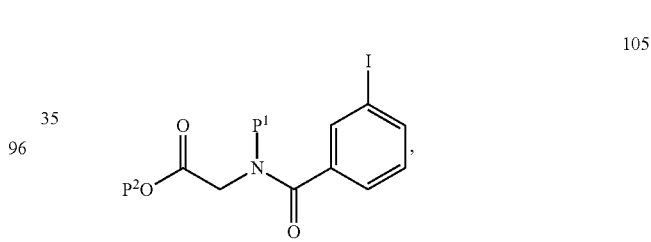
105
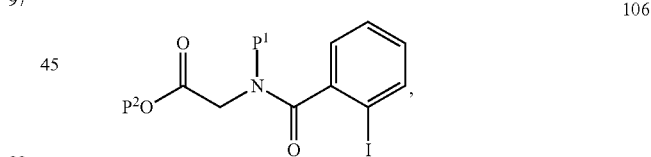
106
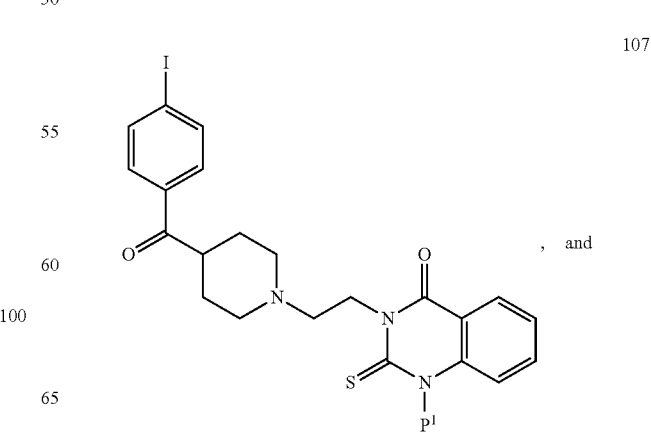
, and
107

-continued

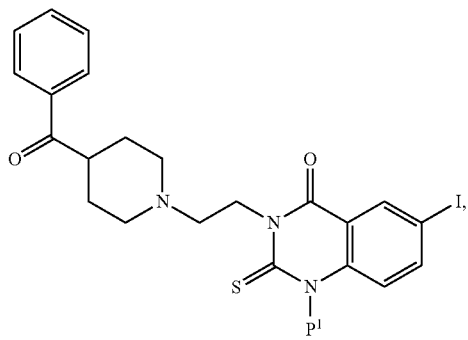
108 wherein Ar is an optionally substituted aryl or heteroaryl, wherein Ar does not have unprotected protic groups; and $P^1$, $P^2$, $P^3$, $P^4$, $P^5$, and $P^6$ are each, independently, protecting groups;
to prepare a compound of Formula I:

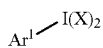 I and
converting the compound of Formula I into a compound of Formula III.

20. The process of claim 19, wherein said converting comprises reacting the compound of Formula I with a compound of Formula IV:

 IV wherein $M^1$ is a borate, stannane, silane, or zinc moiety.

21. The process of claim 20, wherein $M^1$ is $Sn(R^x)_3$, $Si(R^y)_3$, $B(OR^z)_2$, or $B(X^2)_3M^2$; wherein:
each $R^x$ is, independently, $C_{1-6}$ alkyl;
each $R^y$ is, independently, $C_{1-6}$ alkyl;
each $R^z$ is, independently, OH or $C_{1-6}$ alkoxy; or two $R^z$ groups, taken together with the oxygen atoms to which they are attached and the boron atom to which the oxygen atoms are attached, form a 5- to 6-membered heterocyclic ring, which is optionally substituted with 1, 2, 3, or 4 $C_{1-4}$ alkyl groups;
each $X^2$ is, independently, halo; and
$M^2$ is a counterion.

22. The process of claim 21, wherein the compound of Formula IV is $Ar^2BF_3M^2$.

23. The process of claim 21, wherein the compound of Formula IV is $Ar^2BF_3K$.

24. The process of claim 22, wherein the process is carried out in the presence of a catalyst.

25. The process of claim 24, wherein the catalyst is trimethylsilyl trifluoroacetate.

26. A process for making a compound of Formula V:

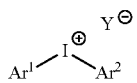 V wherein Y is a counterion that is different than X, the process comprising:

treating a compound of Formula II:

 II with (A) a tetravalent silicon moiety having at least one X group bound to Si, wherein each X is, independently, a ligand that is a conjugate base of an acid HX, wherein HX has a pKa of less than or equal to 12; and is selected from the group consisting of halide, aryl carboxylate, alkyl carboxylate, phosphate, phosphonate, phosphonite, azide, thiocyanate, cyanate, phenoxide, triflate, thiolates, and stabilized enolates; and (B) (1-chloromethyl-4-fluoro-1,4-diazoniabicyclo[2.2.2] octane) bis(tetrafluoroborate), (1-fluoro-4-methyl-1,4-diazoniabicyclo 2.2.2octane) bis(tetrafluoroborate), or an optionally substituted N-fluoropyridinium tetrafluoroborate;

wherein:
$Ar^1$ is selected from the group consisting of:

1
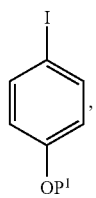

2
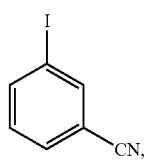

3
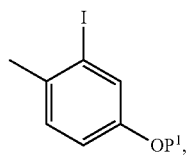

4
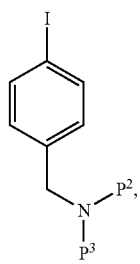

5
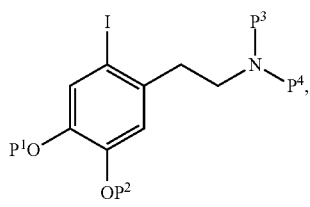

6
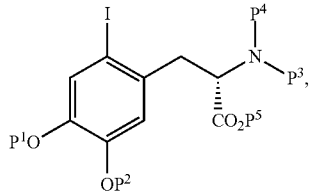

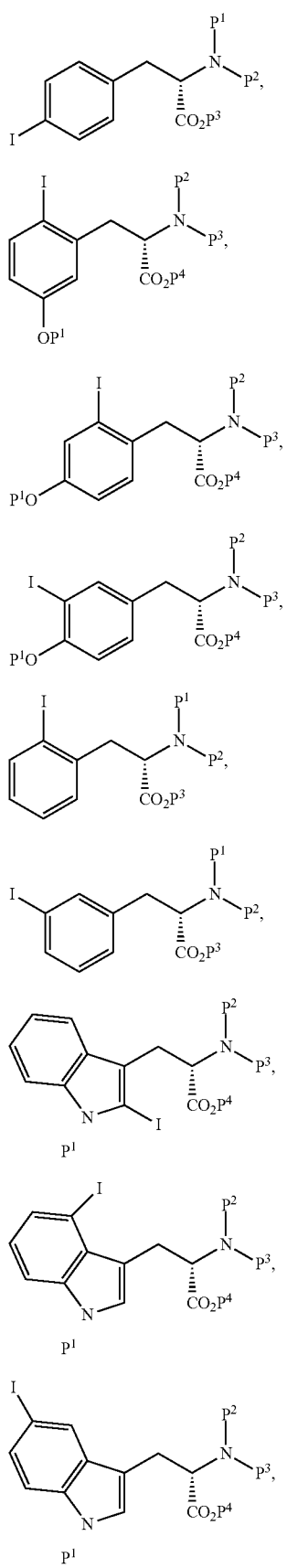
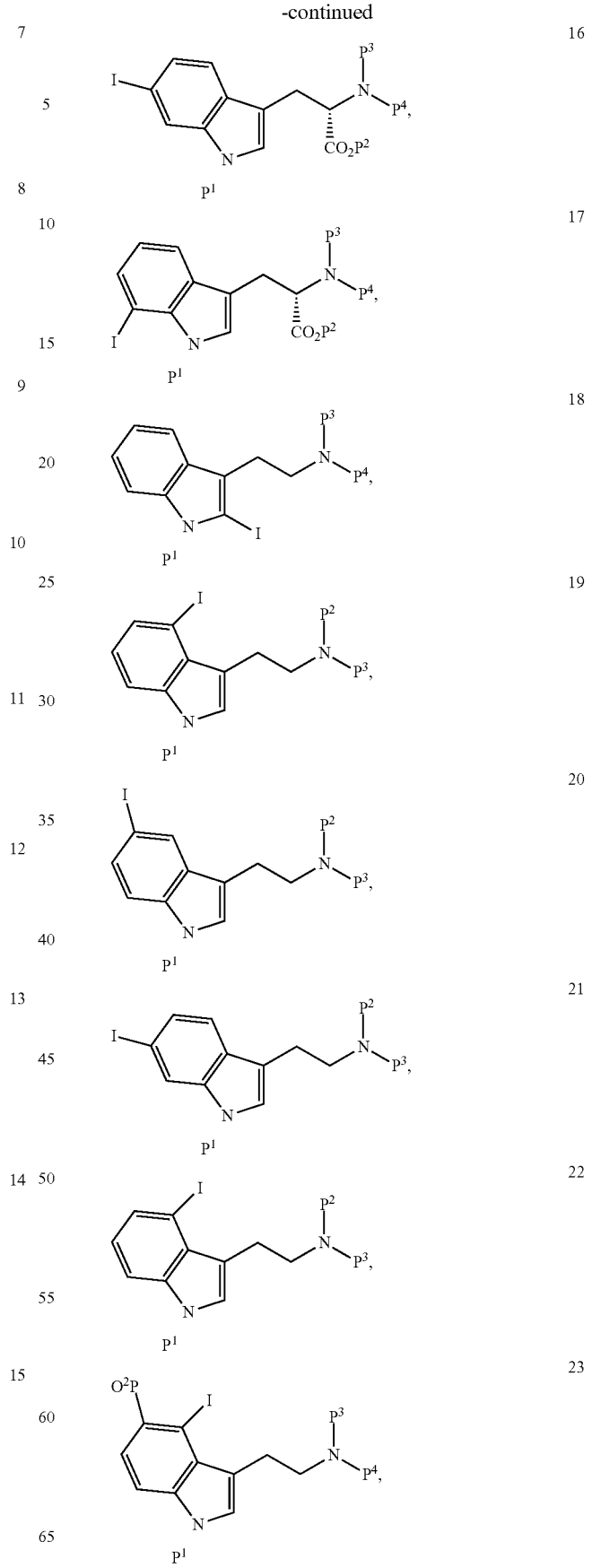

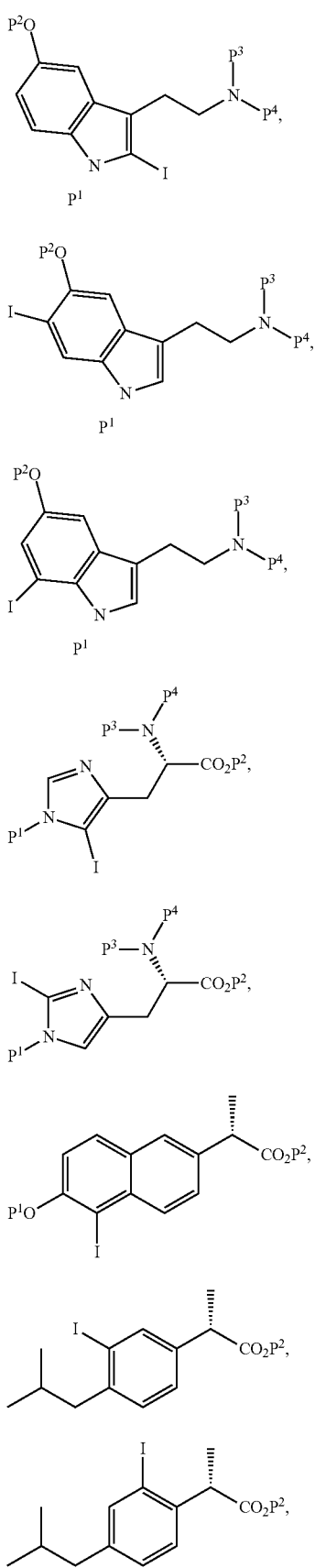
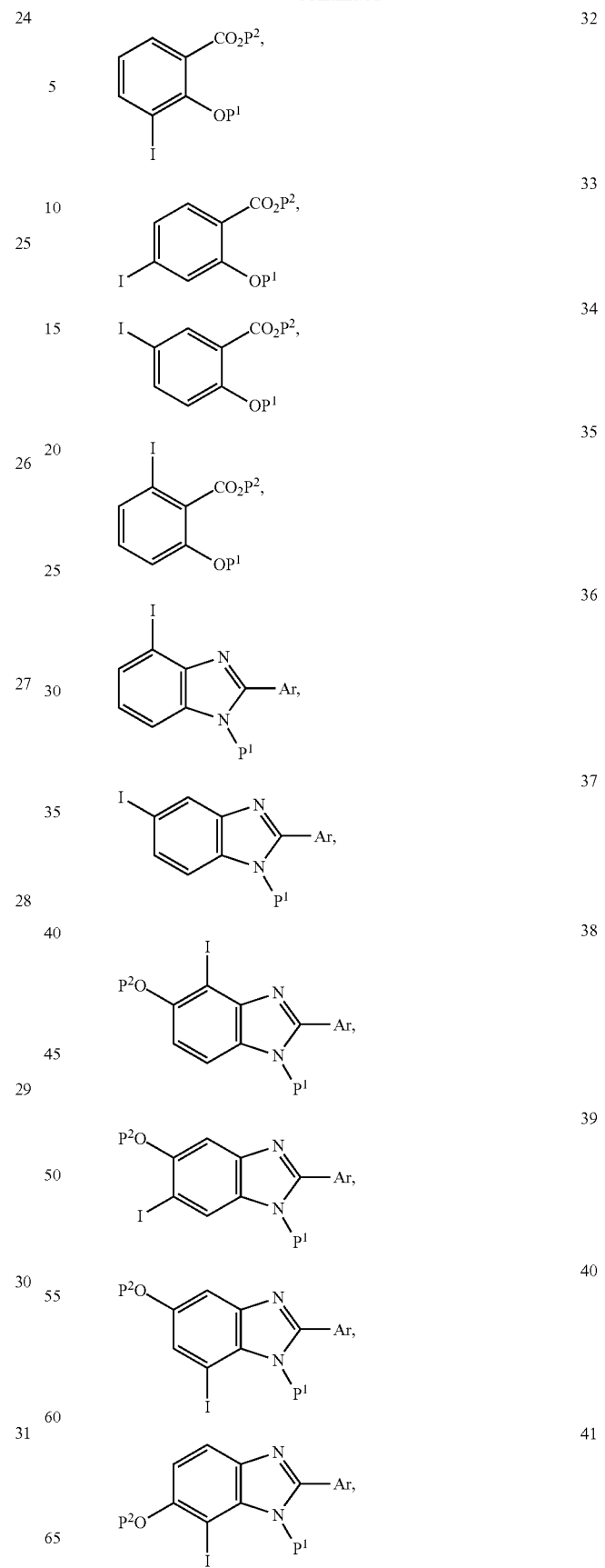

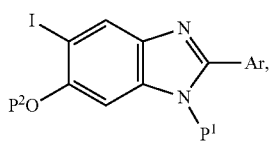
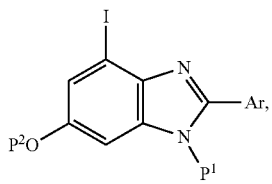
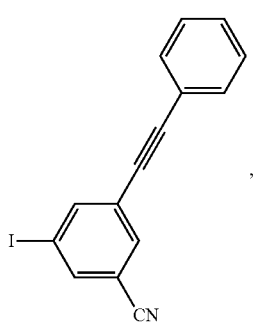
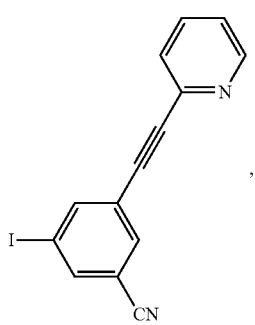
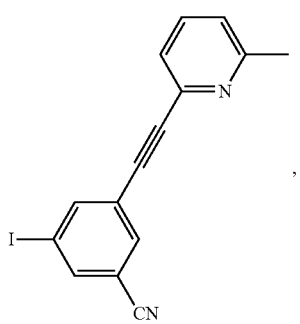
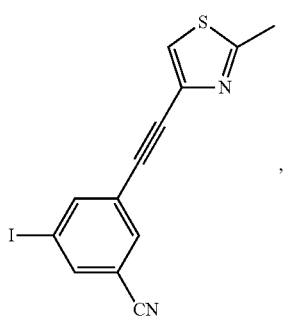
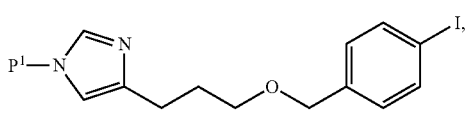
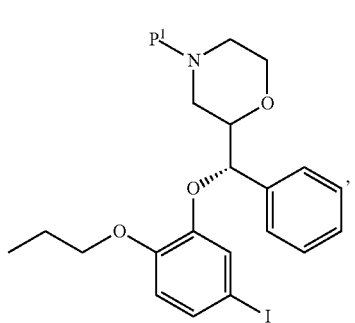
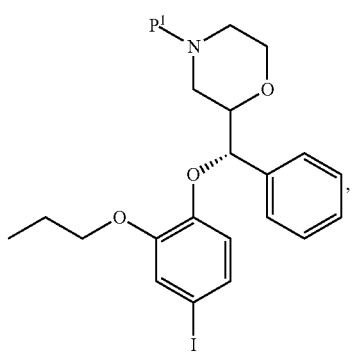
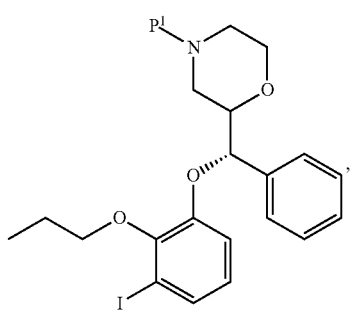
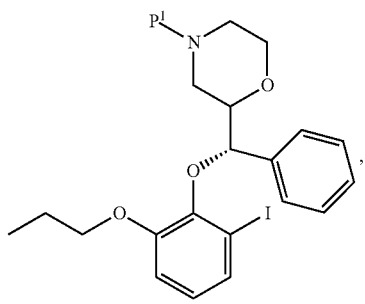
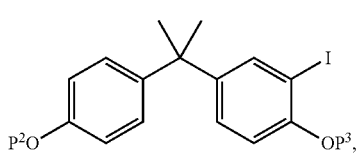

54
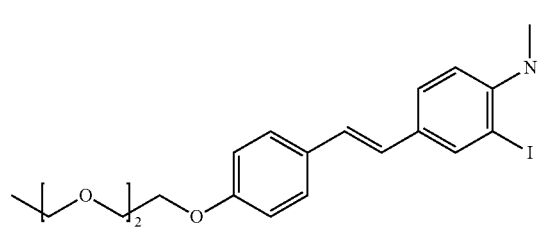
55
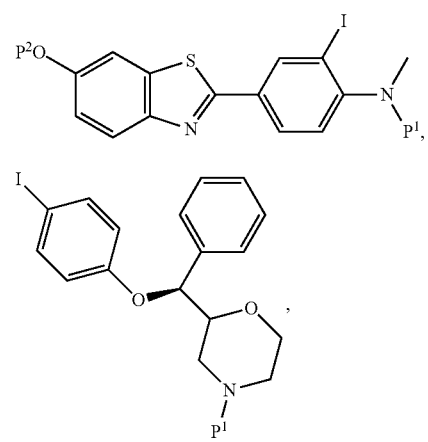
56
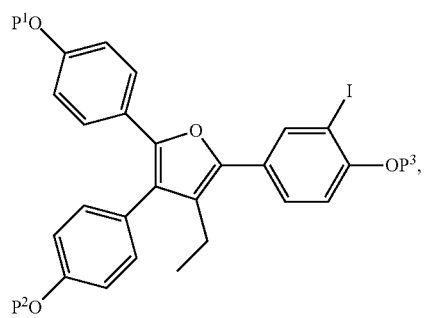
57
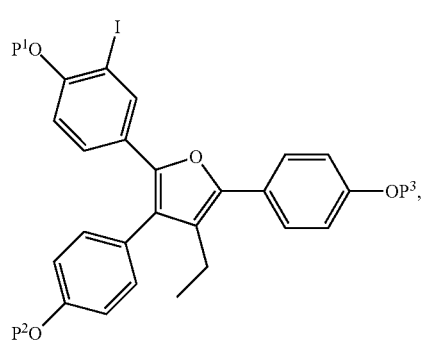
58
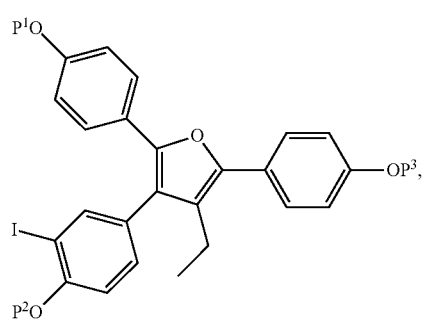
60
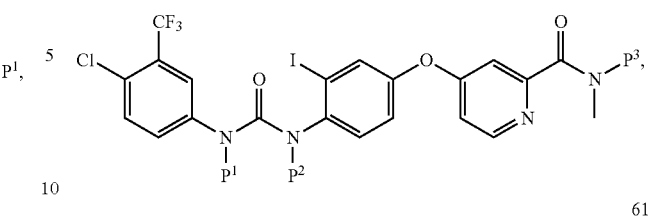
61
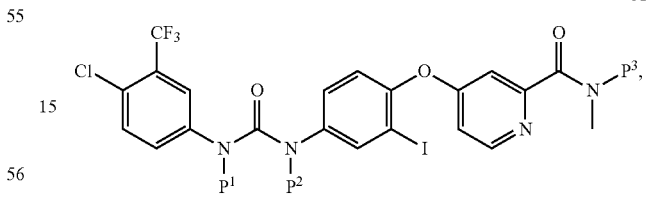
62
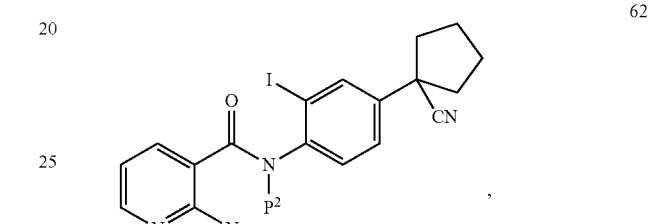
63
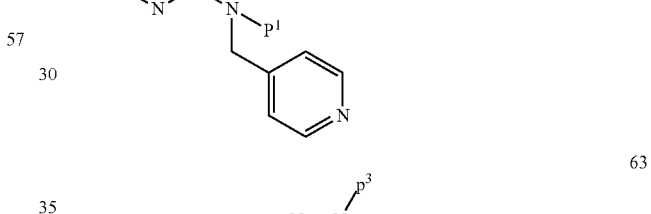
64
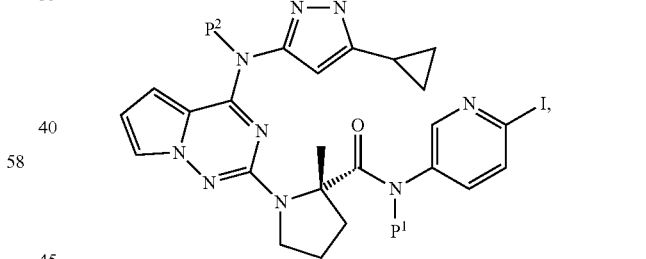
65
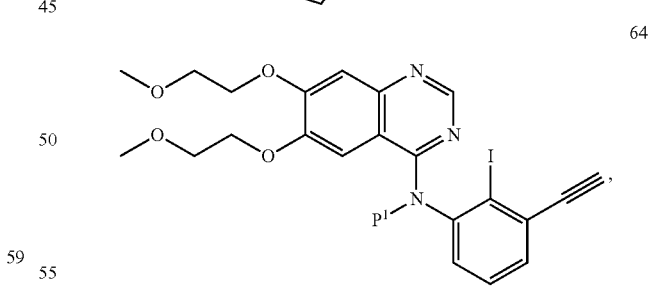
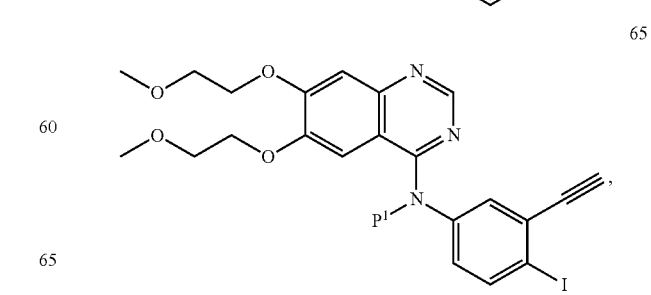

66
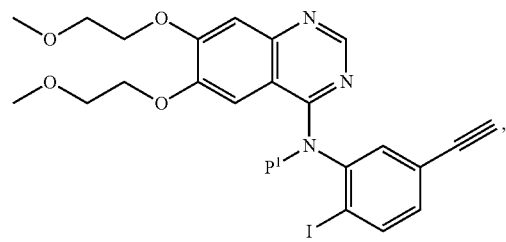
67
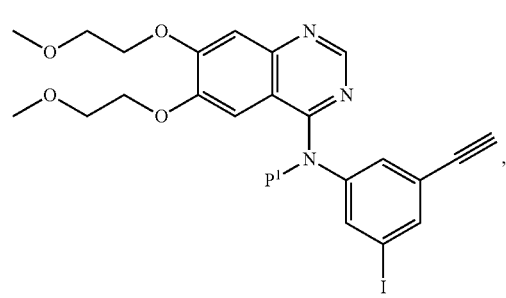
68
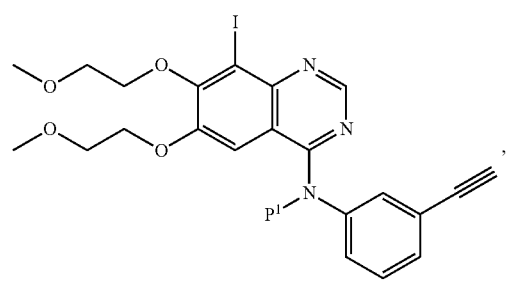
69
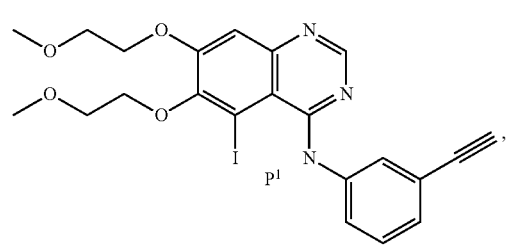
70
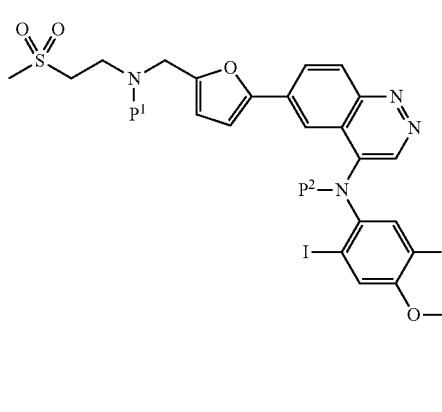
71
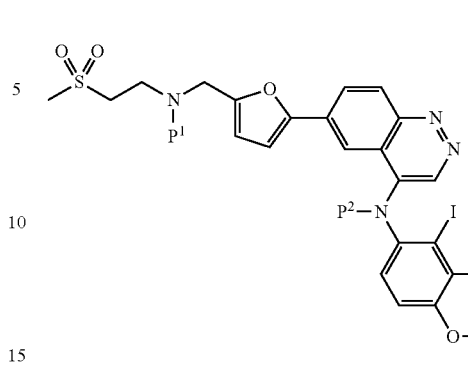
72
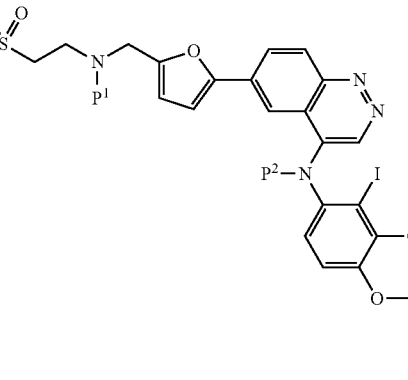
73
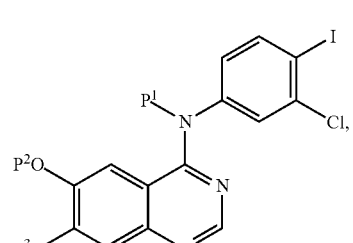
74
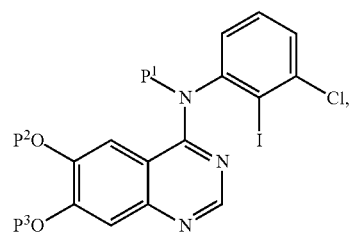
75
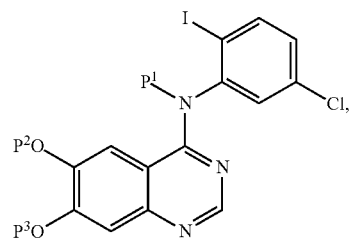

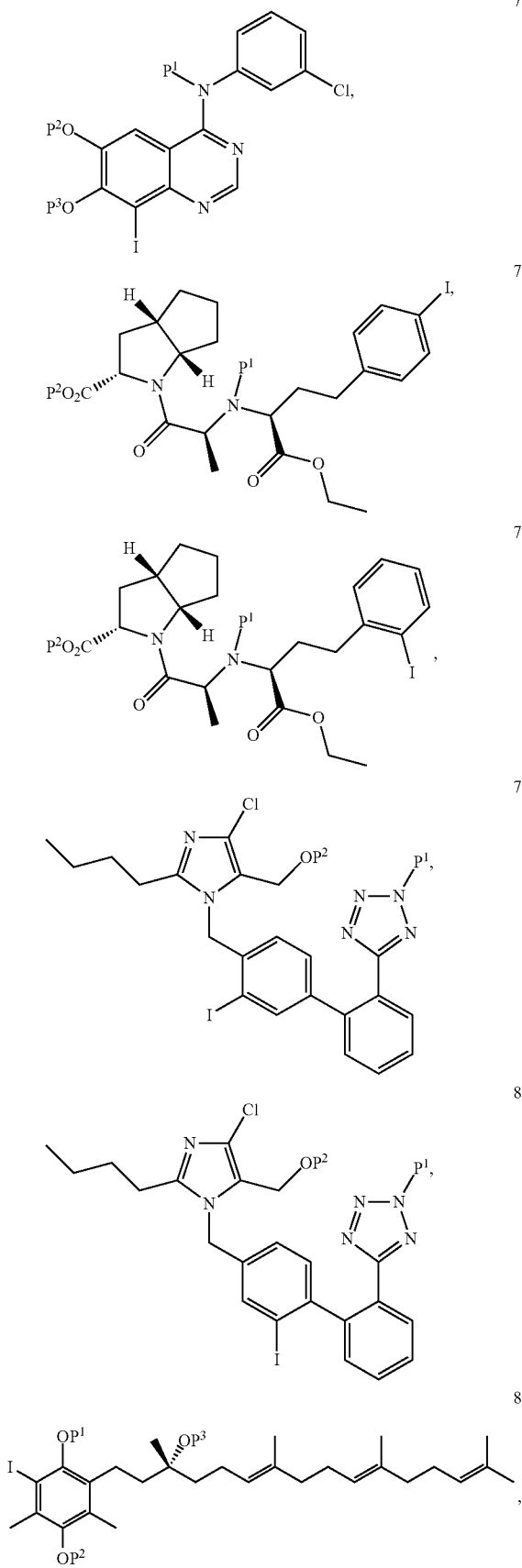
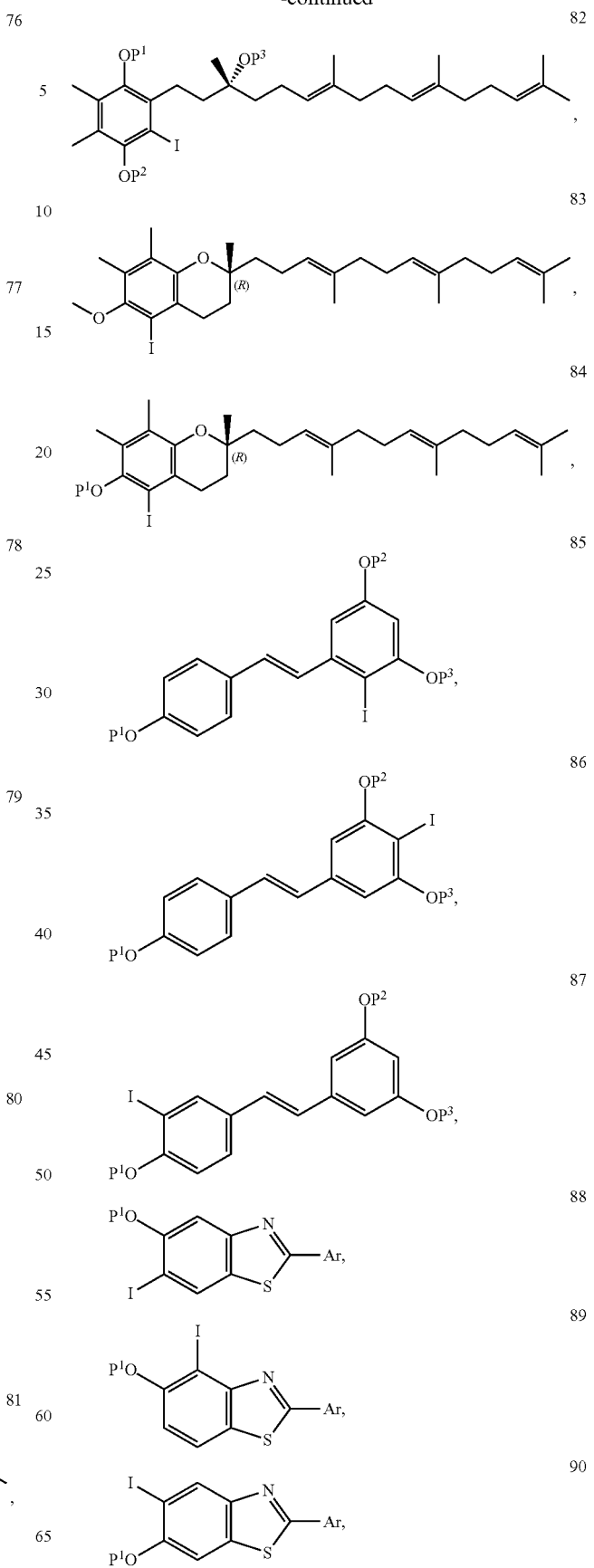

-continued

-continued

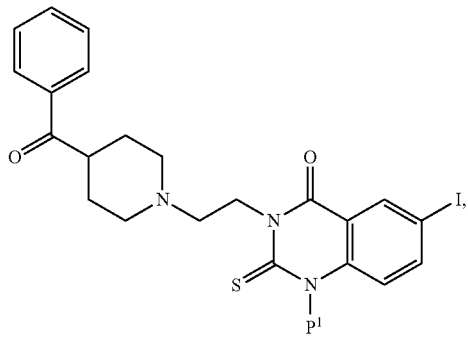

wherein Ar is an optionally substituted aryl or heteroaryl, wherein Ar does not have unprotected protic groups; and $P^1$, $P^2$, $P^3$, $P^4$, $P^5$, and $P^6$ are each, independently, protecting groups;

to prepare a compound of Formula I:

$$Ar^1\text{—}I(X)_2 \quad\quad I$$

converting the compound of Formula I into a compound of Formula III; and subjecting the compound of Formula III to ion-exchange in order to form a compound of Formula V.

27. The process of claim 26, wherein Y is $PF_6^-$ or triflate.

28. The process of claim 26, wherein said ion-exchange comprises treating the compound of Formula III with an aqueous solution of hexaflurophosphate ion, wherein Y is $PF_6^-$.

* * * * *